United States Patent
Tan et al.

(10) Patent No.: US 11,311,457 B2
(45) Date of Patent: Apr. 26, 2022

(54) AUTOMATED DETECTION OF CARDIOPULMONARY RESUSCITATION CHEST COMPRESSIONS

(71) Applicant: ZOLL Medical Corporation, Chelmsford, MA (US)

(72) Inventors: Qing Tan, Winchester, MA (US); Frederick J Geheb, Danvers, MA (US); Gary A Freeman, Waltham, MA (US); Frederick K Newey, Pelham, NH (US); Kristin A Spang, Nashua, NH (US)

(73) Assignee: ZOLL Medical Corporation, Chelmsford, MA (US)

( * ) Notice: Subject to any disclaimer, the term of this patent is extended or adjusted under 35 U.S.C. 154(b) by 381 days.

(21) Appl. No.: 15/911,600

(22) Filed: Mar. 5, 2018

(65) Prior Publication Data

US 2018/0256446 A1    Sep. 13, 2018

Related U.S. Application Data

(63) Continuation-in-part of application No. 15/454,320, filed on Mar. 9, 2017.

(51) Int. Cl.
*A61H 31/00* (2006.01)
*A61N 1/39* (2006.01)
(Continued)

(52) U.S. Cl.
CPC ......... *A61H 31/005* (2013.01); *A61B 5/0205* (2013.01); *A61B 5/0245* (2013.01);
(Continued)

(58) Field of Classification Search
CPC ............ A61H 31/005; A61H 2230/045; A61H 2201/501; A61H 31/00; A61H 31/007;
(Continued)

(56) References Cited

U.S. PATENT DOCUMENTS

| 4,770,164 A | 9/1988 | Lach et al. |
| 6,066,106 A | 5/2000 | Sherman et al. |

(Continued)

FOREIGN PATENT DOCUMENTS

EP    1491175 A1    12/2004

OTHER PUBLICATIONS

Gruben et al., Sternal Force Displacement Relationship During Cardiopulmonary Resuscitation, 115 Journal of Biochemical Engineering 195 (May 1993).
(Continued)

*Primary Examiner* — James B Hull
(74) *Attorney, Agent, or Firm* — ZOLL Medical Corporation

(57) ABSTRACT

A system for assisting a rescuer in providing resuscitative treatment to a victim is described. The system includes a motion sensor configured to generate motion sensor signals that are indicative of motion of the chest of the victim during chest compressions, an input device configured to receive user input indicative of a type of chest compressions, an output device, and a processor, a memory, and associated circuitry, the processor communicatively coupled to the motion sensor, the input device, and the output device and is configured to receive the motion sensor signals and the user input indicative of the type of chest compressions, determine chest compression feedback for the rescuer based on the motion sensor signals, and control the output device to selectively provide the chest compression feedback for the rescuer based at least in part on the type of chest compressions indicated by the user input.

24 Claims, 25 Drawing Sheets

(51) Int. Cl.
  *A61B 5/11* (2006.01)
  *A61B 5/0245* (2006.01)
  *A61B 5/0205* (2006.01)
  *A61B 5/361* (2021.01)
  *A61B 5/145* (2006.01)
  *A61B 5/316* (2021.01)

(52) U.S. Cl.
  CPC ............ *A61B 5/1114* (2013.01); *A61B 5/361* (2021.01); *A61H 31/00* (2013.01); *A61H 31/006* (2013.01); *A61H 31/007* (2013.01); *A61N 1/39* (2013.01); *A61N 1/39044* (2017.08); *A61B 5/1123* (2013.01); *A61B 5/145* (2013.01); *A61B 5/316* (2021.01); *A61B 2562/0219* (2013.01); *A61H 2031/002* (2013.01); *A61H 2201/0153* (2013.01); *A61H 2201/0188* (2013.01); *A61H 2201/10* (2013.01); *A61H 2201/1246* (2013.01); *A61H 2201/169* (2013.01); *A61H 2201/1619* (2013.01); *A61H 2201/501* (2013.01); *A61H 2201/5007* (2013.01); *A61H 2201/5023* (2013.01); *A61H 2201/5043* (2013.01); *A61H 2201/5046* (2013.01); *A61H 2201/5058* (2013.01); *A61H 2201/5061* (2013.01); *A61H 2201/5071* (2013.01); *A61H 2203/0456* (2013.01); *A61H 2230/00* (2013.01); *A61H 2230/045* (2013.01); *A61N 1/3993* (2013.01)

(58) Field of Classification Search
  CPC ...... A61H 2031/002; A61H 2201/0153; A61H 2201/0188; A61B 5/0205; A61B 5/046; A61B 5/1114; A61B 5/0245; A61B 5/04012; A61B 5/1123; A61B 5/145; A61B 2562/0219; A61N 1/39; G09B 23/288; G09B 23/285; G09B 23/286; G09B 23/30; G09B 23/303; G09B 23/32; G09B 23/34
  See application file for complete search history.

(56) References Cited

U.S. PATENT DOCUMENTS

| | | | |
|---|---|---|---|
| 6,129,743 A | 10/2000 | Hsia et al. | |
| 6,213,960 B1 | 4/2001 | Sherman et al. | |
| 6,600,421 B2 | 7/2003 | Freeman | |
| 6,707,476 B1 | 3/2004 | Hochstedler | |
| 6,827,695 B2 | 12/2004 | Palazzolo et al. | |
| 6,865,413 B2 | 3/2005 | Halperin et al. | |
| 7,220,235 B2 | 5/2007 | Geheb et al. | |
| 7,226,427 B2 | 6/2007 | Steen | |
| 7,410,470 B2 | 8/2008 | Escudero et al. | |
| 7,569,021 B2 | 8/2009 | Sebelius et al. | |
| 8,062,239 B2 | 11/2011 | Sherman et al. | |
| 8,465,292 B2 | 6/2013 | Nysaether et al. | |
| 8,478,401 B2 | 7/2013 | Freeman | |
| 8,657,764 B2 | 2/2014 | King | |
| 8,666,480 B2 | 3/2014 | Halperin et al. | |
| 8,690,804 B2 | 4/2014 | Nilsson et al. | |
| 8,700,147 B2 | 4/2014 | Freeman | |
| 8,725,253 B2 | 5/2014 | Johnson et al. | |
| 8,774,945 B2 | 7/2014 | Freeman | |
| 8,868,179 B2 | 10/2014 | Quan et al. | |
| 8,942,803 B1* | 1/2015 | Herken | A61N 1/3925 607/5 |
| 9,149,411 B2 | 10/2015 | Coleman et al. | |
| 9,173,807 B2 | 11/2015 | Freeman | |
| 9,283,140 B2 | 3/2016 | Freeman et al. | |
| 9,308,384 B2 | 4/2016 | Elghazzawi et al. | |
| 9,320,677 B2 | 4/2016 | Johnson et al. | |
| 9,387,147 B2 | 7/2016 | Elghazzawi et al. | |
| 9,486,390 B2 | 11/2016 | Centen et al. | |
| 9,521,977 B2 | 12/2016 | Silver et al. | |
| 9,522,285 B2 | 12/2016 | Herken | |
| 9,658,756 B2 | 5/2017 | Freeman et al. | |
| 9,788,734 B2 | 10/2017 | Tan et al. | |
| 9,844,487 B2 | 12/2017 | Nilsson et al. | |
| 2004/0064169 A1 | 4/2004 | Briscoe et al. | |
| 2005/0101889 A1 | 5/2005 | Freeman | |
| 2006/0270952 A1 | 11/2006 | Freeman et al. | |
| 2007/0232866 A1 | 10/2007 | Nephin | |
| 2007/0270669 A1* | 11/2007 | Parnagian | A61B 5/044 600/301 |
| 2008/0255482 A1* | 10/2008 | Lurie | A61H 31/007 601/43 |
| 2008/0281168 A1* | 11/2008 | Gibson | A61B 5/0205 600/301 |
| 2009/0204161 A1 | 8/2009 | Powers et al. | |
| 2009/0260637 A1 | 10/2009 | Sebelius et al. | |
| 2010/0298718 A1 | 11/2010 | Gilham et al. | |
| 2011/0040217 A1 | 2/2011 | Centen | |
| 2011/0166490 A1 | 7/2011 | Woerlee et al. | |
| 2011/0301513 A1 | 12/2011 | Freeman | |
| 2012/0330200 A1* | 12/2012 | Voss | A61H 31/004 601/41 |
| 2013/0023781 A1* | 1/2013 | Freeman | A61B 5/0535 600/529 |
| 2013/0060172 A1 | 3/2013 | Palazzolo | |
| 2013/0085425 A1 | 4/2013 | Monsiuers et al. | |
| 2014/0323928 A1 | 10/2014 | Johnson | |
| 2014/0342330 A1* | 11/2014 | Freeman | G09B 23/288 434/265 |
| 2015/0096559 A1* | 4/2015 | Duval-Arnould | A61M 16/0078 128/202.22 |
| 2016/0206504 A1* | 7/2016 | Giarracco | A61B 5/0261 |
| 2016/0338904 A1 | 11/2016 | Lurie | |
| 2017/0035650 A1 | 2/2017 | Taylor | |
| 2018/0161239 A1* | 6/2018 | Choi | A44C 5/00 |
| 2018/0271380 A1* | 9/2018 | Gregg | A61B 5/6831 |

OTHER PUBLICATIONS

EP Search Report dated Aug. 6, 2018, Application No. 18161003.1.

* cited by examiner

AUTOMATED DETECTION OF CARDIOPULMONARY RESUSCITATION CHEST COMPRESSIONS

CROSS-REFERENCE TO RELATED APPLICATIONS

This application is a continuation-in-part under 35 U.S.C. § 120 of U.S. patent application Ser. No. 15/454,320 filed on Mar. 9, 2017. All subject matter set forth in the above referenced application is hereby incorporated by reference in its entirety into the present application as if fully set forth herein.

BACKGROUND

For cardiac arrest victims, cardiopulmonary resuscitation (CPR) may include a variety of therapeutic interventions including chest compressions, defibrillation, and ventilation. Chest compressions during CPR may maintain blood circulation so that oxygen can be delivered to the body until the heart resumes an effective rhythm. The chest compressions may be performed by automated mechanical devices, such as, for example, the ZOLL® AutoPulse®. Alternatively, or additionally, the chest compressions may be performed manually, for example, by compressing the chest of a victim with the hands of a rescuer, or manually with mechanical assistance, for example, by compressing the chest of the victim with a hand-held device such as, for example, the ZOLL® ResQPump®. Feedback relating to characteristics of the chest compressions may be provided to the rescuer in real-time during the chest compressions. Such feedback may allow the rescuer to modify and, thereby, improve the efficacy of the chest compressions. The feedback may also allow the rescuer to more effectively combine and coordinate the chest compressions with other resuscitative therapies.

SUMMARY

An example of a system for assisting a rescuer in providing resuscitative treatment to a victim according to the disclosure includes at least one motion sensor configured to generate motion sensor signals that are indicative of motion of the chest of the victim during chest compressions, at least one input device configured to receive user input indicative of a type of chest compressions, at least one output device, and a processor, a memory, and associated circuitry, the processor communicatively coupled to the at least one motion sensor, the at least one input device, and the at least one output device and configured to receive the motion sensor signals and the user input indicative of the type of chest compressions, determine chest compression feedback for the rescuer based on the motion sensor signals, and control the at least one output device to selectively provide the chest compression feedback for the rescuer based at least in part on the type of chest compressions indicated by the user input.

Implementations of such a system may include one or more of the following features. The processor may be configured to control the at least one output device to suppress at least a portion of the chest compression feedback based at least in part on the type of chest compressions. The chest compression feedback may include first chest compression feedback and second chest compression feedback and the processor may be configured to control the at least one output device to provide the first chest compression feedback and suppress the second chest compression feedback based at least in part on the type of chest compressions indicated by the user input. The processor may be configured to control the at least one output device to provide the first chest compression feedback and suppress the second chest compression feedback in response to the user input that indicates that the type of chest compressions is mechanically assisted manual ACD chest compressions. The first chest compression feedback may be a chest compression timer or a chest compression pause timer. The at least one output device may be configured to provide the chest compression timer and the chest compression pause timer based on the motion sensor signals. The second chest compression feedback may include at least one of compression depth feedback and compression rate feedback. The second chest compression feedback may include an indicator of chest release. The second chest compression feedback may include an indicator of chest compression induced circulation. The second chest compression feedback may include a metronome. The processor may be configured to control the at least one output device to provide the chest compression feedback in a default feedback mode in an absence of user input indicative of the type of chest compressions. The default feedback mode may correspond to manual chest compressions. The processor may be configured to transition the at least one output device from the default feedback mode to a selected feedback mode in response to the processor receiving the user input indicative of the type of chest compressions. In the selected feedback mode, the at least one output device may be configured to suppress at least a portion of chest compression feedback provided in the default feedback mode. In the selected feedback mode, the at least one output device may be configured to provide an indication of the type of chest compressions associated with the selected feedback mode. The processor may be configured to operate the at least one output device in the default feedback mode upon initiation of a patient case. The at least one input device may include one or more soft-keys. The at least one output device may include one or more of a display and a speaker. The processor may be configured to store, in the memory, with data that indicates the type of chest compressions. The at least one input device, the at least one output device, the processor, the memory, and the associated circuitry may be disposed in a defibrillator.

BRIEF DESCRIPTION OF THE DRAWINGS

Various aspects of the disclosure are discussed below with reference to the accompanying figures, which are not intended to be drawn to scale. The figures are included to provide an illustration and a further understanding of various examples, and are incorporated in and constitute a part of this specification, but are not intended to limit the scope of the disclosure. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure. A quantity of each component in a particular figure is an example only and other quantities of each, or any, component could be used.

DETAILED DESCRIPTION

Figure 1A:
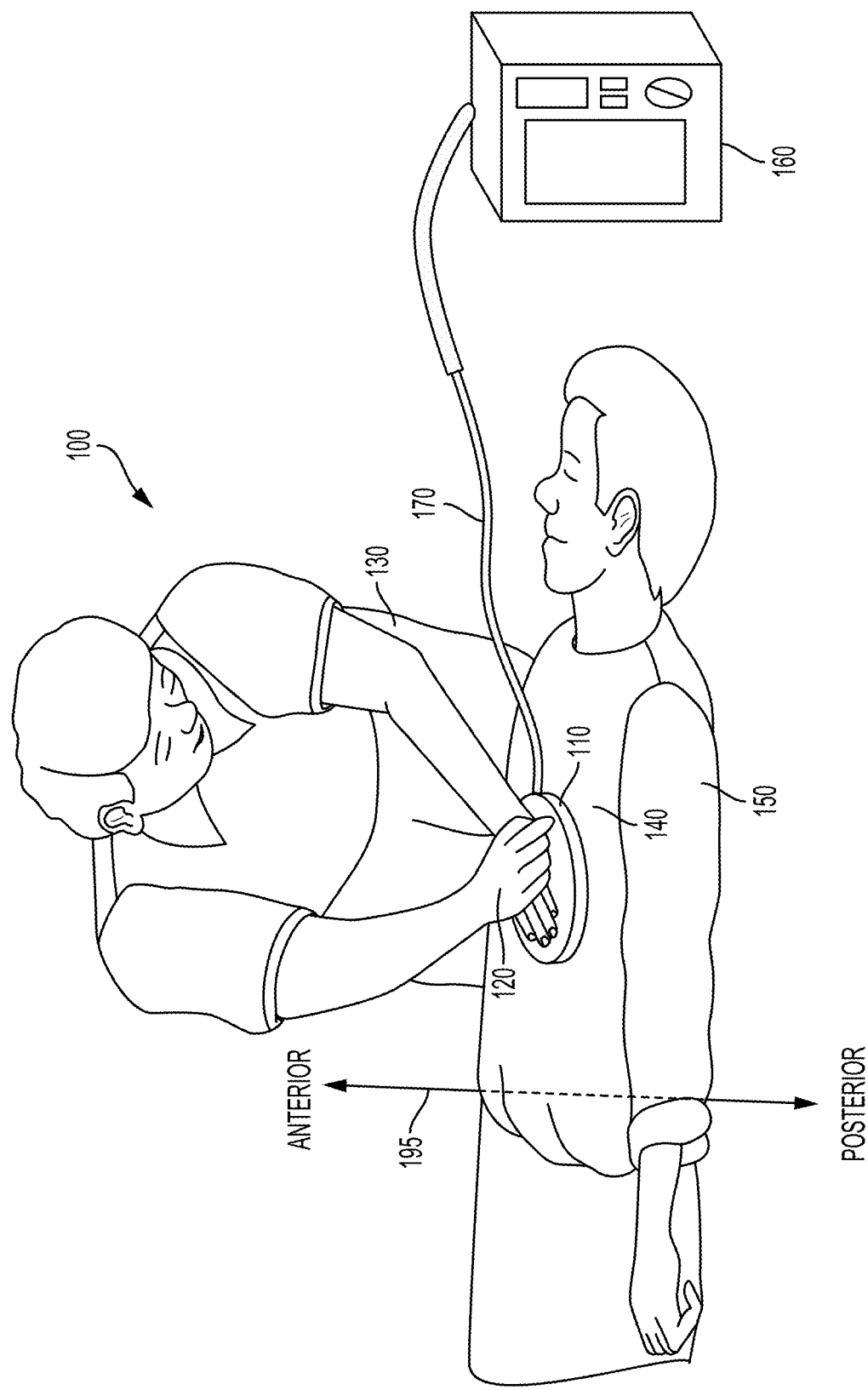
FIG. 1A is a schematic diagram of an example of a system for assisting a rescuer in providing manual chest compressions to a victim.

In order for a cardiac arrest victim to receive proper chest compressions with regard to maintaining sufficient blood flow, it may be beneficial to provide real-time chest compression feedback to a rescuer providing the chest compressions. The chest compression feedback may allow the rescuer to adjust various aspects of the chest compressions in order to improve patient care. Analyzed signals from a motion sensor may determine chest compression parameters and chest compression feedback based on the determined parameters. The motion sensor, when properly placed against the sternum of the chest during the delivery of chest compressions, is configured to detect chest wall motion and generate one or more signals indicative of the chest wall motion. Compressions are considered ongoing when one or more compression cycles are immediately followed by, or preceded by, one or more additional compression cycles performed at a resuscitative rate. The resuscitative rate is a compression rate considered effective to induce blood flow in a cardiac arrest victim, typically 60 to 120 compressions per minute.

The motion sensor may be disposed or otherwise incorporated within and/or communicatively coupled to a feedback device configured to analyze the signals from the motion sensor and provide the feedback to the rescuer. The chest compression parameters may include, for example, a compression rate, a compression depth, and/or a decompression velocity (e.g., a release velocity). The feedback may provide an indication of current values for chest compression parameters, target values for chest compression parameters, and/or recommended changes to chest compression parameters. For example, the feedback may include indications to increase or decrease compression depth, indications to compress at a faster or slower rate, and/or indications to quickly and completely release the chest of the patient after each compression. In general feedback may be corrective feedback (i.e., feedback configured to cause a rescuer to change an aspect of the resuscitative care) and/or may be reported measurements (i.e., feedback that indicates a value or status of an aspect of the resuscitative care without a suggested change).

Because the chest compression parameters for manual compressions are controllable by the rescuer delivering the compressions, the rescuer is able to respond to the feedback and effect a change in the chest compression parameters. Additionally, because it is common for manual chest compressions to deviate from recommended guidelines (e.g., ACLS guidelines) due to variations in human performance (e.g., due to rescuer inconsistencies, fatigue, etc.), feedback based on an analysis of manual chest compression waveforms generally leads to improvements in the quality of chest compressions. For at least this reason, rescuer feedback systems provided as stand-alone systems (e.g., a feedback system in a mobile device or other non-medical computing device) or as part of medical device systems (e.g., a feedback system in or otherwise provided with a defibrillator or other resuscitative care and/or medical device) generally include an algorithm designed to analyze a compression waveform and determine rescuer feedback therefrom.

Automated chest compression systems generally utilize pre-programmed values for various chest compression parameters. For example, the manufacturer may determine these pre-programmed values and/or a user may determine or adjust these pre-programmed values prior to usage of the system (i.e., compression parameter values are not determined or adjusted in real-time during chest compressions). These parameters may not be adjustable by the rescuer during delivery of the chest compressions. Providing rescuer feedback for non-adjustable parameters may confuse and/or cause anxiety for the rescuer, and may undesirably lead the rescuer to interfere with the delivery of the chest compressions in an unnecessary attempt to change these parameters. As timely and efficient delivery of resuscitative care is crucial for patient survival, such confusion and/or distraction on the part of the rescuer may be detrimental to the effective resuscitation of the patient. Further, a system designed to provide feedback for one type of compressions may generate irrelevant and/or inaccurate and misleading feedback when applied to another type of compressions.

Thus, in order to provide a feedback system that is user-friendly and compatible with multiple types of chest compression delivery systems, it may be beneficial for the system to automatically identify the type of chest compressions and automatically tailor the feedback provided to the rescuer based on the identified type of chest compressions. Additionally, the automated determination of the type of chest compressions by the feedback device enables the feedback device to quickly and efficiently provide relevant and accurate feedback without requiring rescuer input and/or reconfiguration of feedback settings and/or software and without causing rescuer confusion.

As a further benefit, automated determination of the type of chest compressions enables the system to recognize a transition in care and adjust provided feedback accordingly. For example, a single feedback device may provide feedback to improve manual compressions by a first responder and then automatically detect a change to automated or mechanically assisted compressions (e.g., mechanically assisted manual compressions). For example, secondary responders, such as medical personnel from an emergency response team or a hospital, may have equipment and training to provide the automated and/or mechanically assisted compressions. These secondary responders may switch the compression delivery for the patient to one of these systems. In various medical or emergency response situations, the compressions may change one or more times from one type of system to another. A feedback system configured to detect these changes (e.g., as described herein) can appropriately adjust feedback and maintain a continuity of patient records and/or resuscitative care therapies controlled and/or recorded by the system.

As described with regard to FIGS. 15A-18, a feedback system that is compatible with multiple types of chest compression delivery systems may additionally provide a capability of automatically tailoring the feedback provided to the rescuer based on a user-selected indication of the type of chest compression. The described system may not allow the user to select the specific feedback provided but rather the system selects the specific feedback based on the user indication of the type of chest compression. Thus the system simplifies operations for the user as the user may only need to select the type of chest compressions and then the system determines which feedback should or should not be provided. This preserves the ability of the system to select and provide relevant feedback and refrain from providing feedback which may be confusing and/or irrelevant. For example, feedback on parameters that are not under the control of the user may confuse the user. Efficient resuscitative care that is provided to the patient as quickly as possible after a medical event and with proper technique is crucial to a positive patient outcome. Therefore, the described system may provide the advantage of simplifying implementation of the resuscitative care for the user by limiting the choices that the user needs to make to the type of chest compression and by not requiring the user to select specific provided or suppressed feedback parameters. Additionally, configuration settings in control software and/or firmware for such a system may determine whether or not the system provides automatic identification of the type of compression and/or accepts user input indicative of the type of chest compression. As these configuration settings may be determined locally at the feedback system and/or via external computing devices communicatively coupled to the feedback system, the device (e.g., defibrillator, patient monitor, etc.) that includes the feedback system may be tailored to the needs and capabilities of the users. Further, if the user is limited to a particular type of chest compression delivery, then such a system may increase the confidence of the user in the system based on the knowledge that the user configured the system to the particular type of chest compression delivery. Such confidence may be beneficial since during a resuscitation event it may be important for the user to rely on the feedback from the system in order to provide effective care since improperly performed resuscitative care, such as CPR, may be detrimental to the patient outcome.

Table 1 lists examples of various types of chest compressions. These various types are discussed below in further detail in reference to FIGS. 1-3.

TABLE 1

| TYPE OF CHEST COMPRESSIONS | DELIVERY SYSTEM EXAMPLE |
|---|---|
| manual chest compressions | hands of rescuer |
| mechanically assisted manual ACD chest compressions | hand-held ACD device |
| automated chest compressions | belt-based system |
| automated chest compressions | piston-based system |
| automated ACD chest compressions | piston-based ACD system |

Manual chest compressions refer to classic two-hand CPR (e.g., compressions according to Advanced Cardiac Life Support (ACLS) guidelines) where the compression parameters (e.g., compression rate, periodicity, compression depth, release velocity, and other compression waveform characteristics) are controlled by and subject to variability due to physical actions of the CPR provider (e.g., the rescuer). Mechanically assisted manual ACD chest compressions (e.g., mechanically assisted ACD compressions delivered via manual operation of an ACD device) refer to compressions delivered using devices that, though mechanical in nature, depend on the physical activity of the CPR provider to control the compression parameters. Automated chest compressions refer to chest compressions delivered by devices that are controlled by computerized control systems, electro-mechanical systems, or the like, such that the compression parameters are predetermined by the programming or design of the device, and are not subject to variability due to the physical actions of a CPR provider (other than providing input to the control system or adjusting set points for an electromechanical system, as allowed by the system). For example, the automated chest compressions may be belt-based compressions, piston-based compressions, or piston-based ACD compressions.

Techniques are presented herein for assisting a rescuer in providing resuscitative treatment to a victim using the various types of chest compressions. A motion sensor placed on the sternum of the chest generates signals indicative of motion of the chest of the victim. A computing device (e.g., processor(s) provided within a defibrillator, medical monitor, mobile device for managing resuscitation-related activities, etc.) receives these signals and determines or renders one or more compression waveforms. The computing device detects features characteristic of various types of compressions in the one or more compression waveforms. Based on these detected features, the computing device identifies the compression waveforms as a particular type of compression waveform (e.g., a manual compression waveform, an automated compression waveform, an ACD waveform, etc.).

The computing device controls an output device to selectively provide feedback to the rescuer based on the identified compression waveform. A defibrillator that includes or is controlled by the computing device may utilize the compression waveforms to synchronize delivery of defibrillation shocks with the occurrence of specific features in the compression waveforms. Automatically detecting the type of chest compressions and selectively providing feedback may provide the capability of improving the effectiveness of the resuscitation in response to the feedback. Further, the automated detection and selective feedback may improve the versatility of the medical equipment providing the feedback without detrimentally affecting resuscitative care. Coordinating the timing of defibrillation shocks and phases in the chest compression cycles may further improve the efficacy of resuscitative care.

Other capabilities may be provided and not every implementation according to the disclosure must provide any, let alone all, of the capabilities discussed. Further, it may be possible for an effect noted above to be achieved by means other than that noted and a noted item/technique may not necessarily yield the noted effect.

Figure 1B:
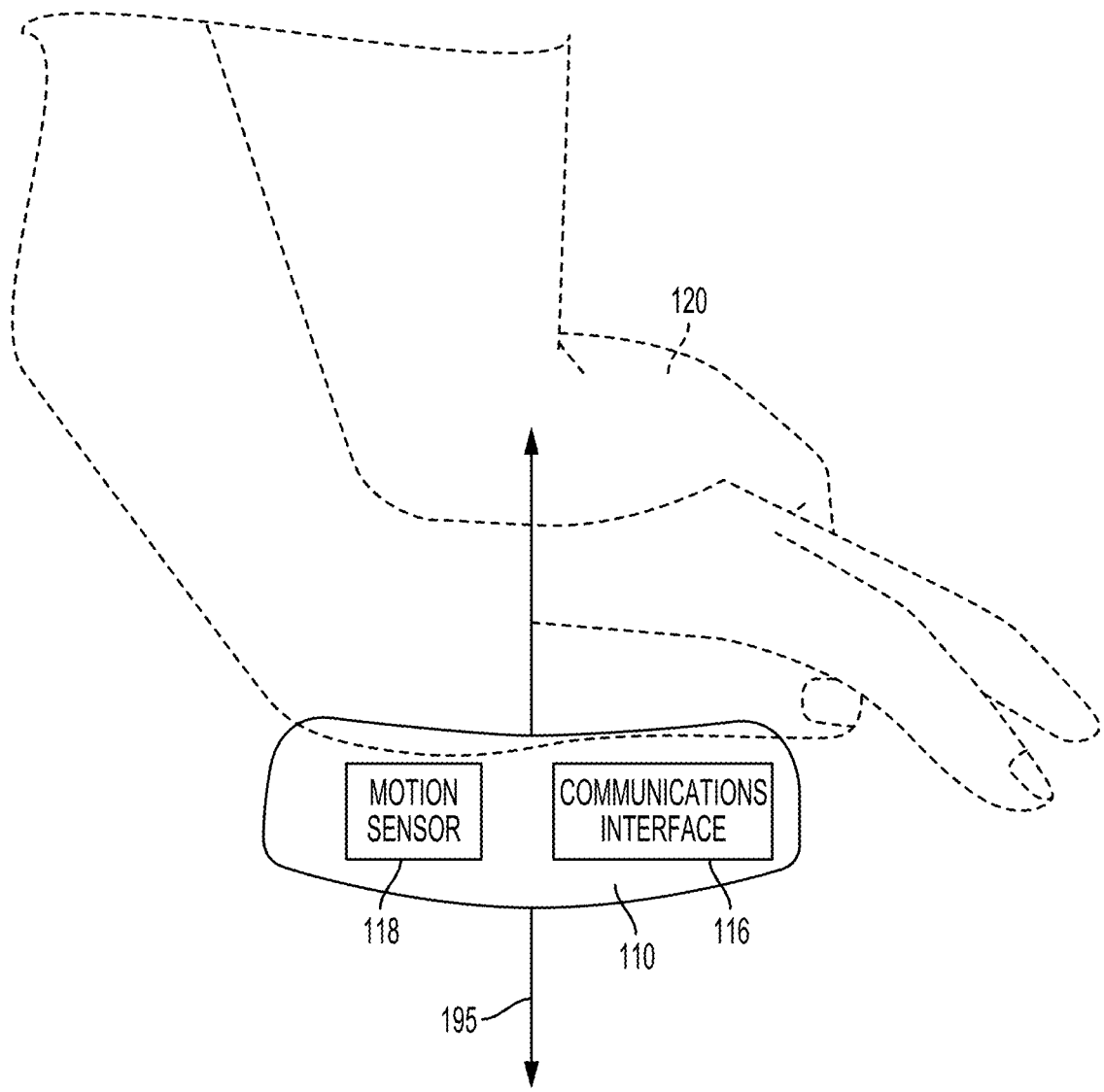
FIG. 1B is a schematic diagram of an example of the compression puck from FIG. 1A.

Referring to FIG. 1A, a schematic diagram of an example of a system for assisting a rescuer in providing manual chest compressions to a victim is shown. The manual CPR system 100 includes a chest compression puck 110 and a computing device 160. As shown in FIG. 1B, the chest compression puck 110 may include a motion sensor 118 and a communications interface 116.

The motion sensor 118 is a device configured to sense motion of the chest 140 of a victim 150 during chest compressions as applied by a rescuer 130. Although one rescuer 130 is shown in FIG. 1A, more than one rescuer may participate in resuscitation activities for the victim 150. During chest compressions, the rescuer 130 places his or her hands 120 on the compression puck 110 and compresses and releases the chest 140 of the victim 150 along a compression axis approximately parallel to an anterior-posterior axis 195 of the victim. As discussed in more detail below in reference to FIGS. 13A and 13B, the motion sensor 118 may be a component of a defibrillation electrode assembly and/or used in conjunction and/or coordination with a defibrillation electrode assembly.

The motion sensor 118 is configured to provide motion sensor signals to the computing device 160. The motion sensor signals are signals generated by the motion sensor 118 in response to movement of the motion sensor 118. The movement of the motion sensor 118 may occur during chest compressions and the motion sensor signals may be one or more signals indicative of the motion of the chest 140 of the victim 150. The movement of the motion sensor 118 may also occur when a caregiver is positioning the motion sensor 118 on the victim 150 and/or in response to motion of the victim other than chest compression motion (e.g., motion of the victim due to motion of a support structure such as a gurney and/or due to motion of a transport vehicle such as an ambulance). As described in detail below, the computing device 160 may include algorithms configured to identify motion sensor signals that correspond to repetitive chest compressions. The motion sensor 118 may provide the one or more signals to the computing device 160 via a connection 170 (e.g., a wired and/or wireless connection). This connection 170 is shown as a wired connection in FIG. 1A as an illustrative example only and not limiting of the disclosure. The motion sensor 118 and the computing device 160 are discussed in further detail below in reference to FIG. 4.

Figure 2A:
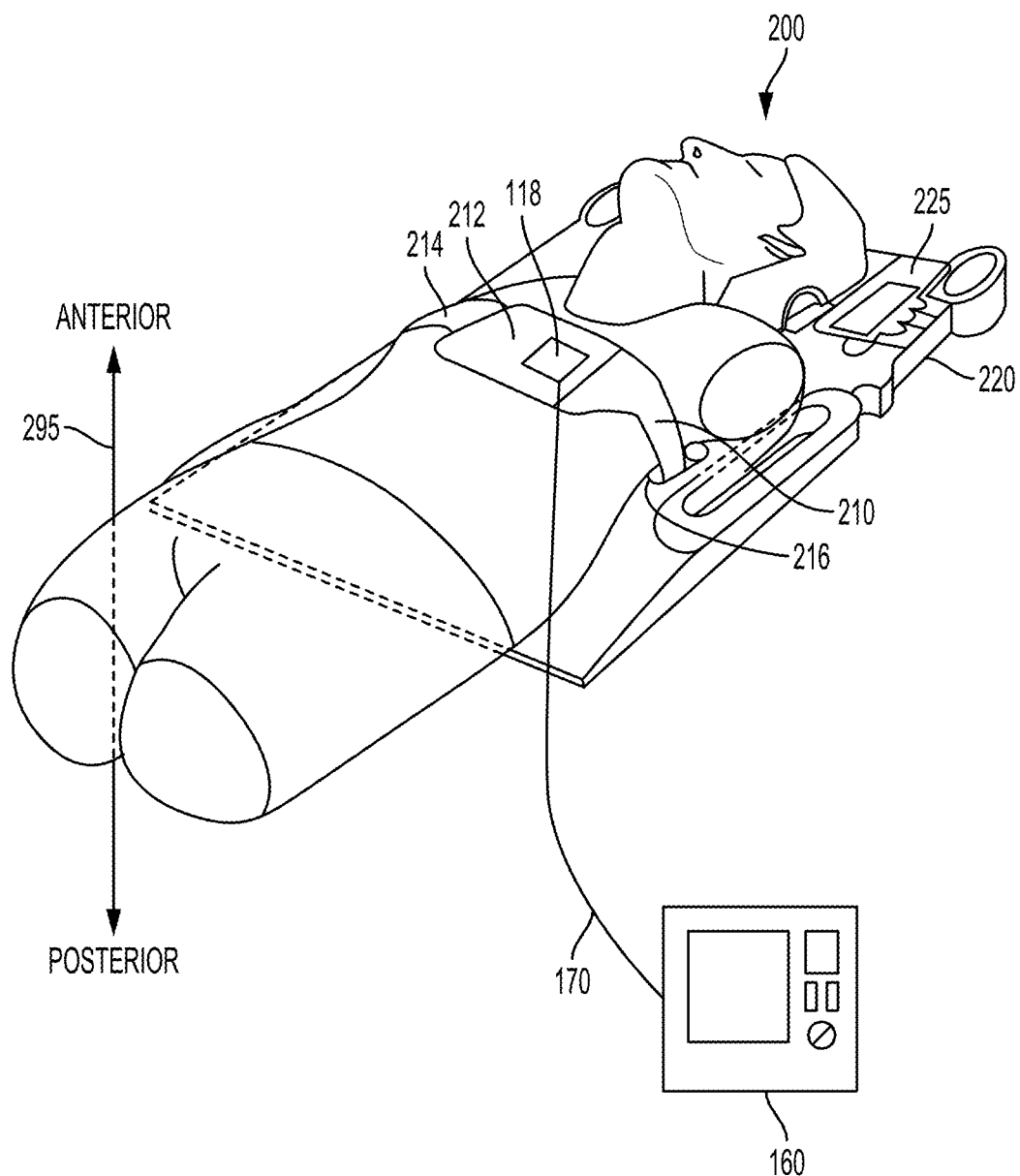
FIG. 2A is a schematic diagram of an example of a belt-based system for providing automated chest compressions to a victim.

Referring to FIG. 2A, a schematic diagram of an example of a belt-based system for providing automated mechanical chest compressions to a victim is shown. The belt-based system 200 in FIG. 2A (e.g., ZOLL® AutoPulse®) includes a belt drive platform 220, a compression belt 210, and a controller 225. The belt drive platform 220 supports a victim in a substantially supine position at least during the chest compressions. The compression belt 210 may include a load distribution panel 212 and pull straps 214. The pull straps 214 are configured to insert into openings 216 in the belt drive platform 220 on either side of the victim. A drive spool (not shown), a motor (not shown), and associated electrical and mechanical components are disposed within the belt drive platform 220. The pull straps 214 wrap around the drive spool. The motor moves the drive spool such that the pull straps 214 may wrap and unwrap from the drive spool in order for the compression belt 210 to provide and release the chest compressions. The controller 225 may include a processor, a memory, and a communications interface. The controller 225 controls the motor and the associated electrical and mechanical components to control the chest compressions delivered by the compression belt 210. The controller 225 may transmit and/or receive information to and/or from an external computing device via the communications interface.

The compression belt 210 may include the motion sensor 118. In an implementation, the motion sensor 118 may be coupled to the compression belt 210. The motion sensor 118 may send one or more signals indicative of the motion of the chest of the victim to the controller 225 via a wired and/or wireless connection. In various implementations, the motion sensor 118 and/or the controller 225 may send the one or more signals indicative of the motion of the chest of the victim to the computing device 160. The motion sensor 118 may provide the one or more signals to the computing device 160 via the connection 170 (e.g., a wired and/or wireless connection). This connection 170 is shown as a wired connection in FIG. 2A as an illustrative example not limiting of the disclosure. As discussed in more detail below in reference to FIGS. 13A and 13B, the motion sensor 118 may be a component of a defibrillation electrode assembly and/or used in conjunction and/or coordination with a defibrillation electrode assembly.

Figure 2B:
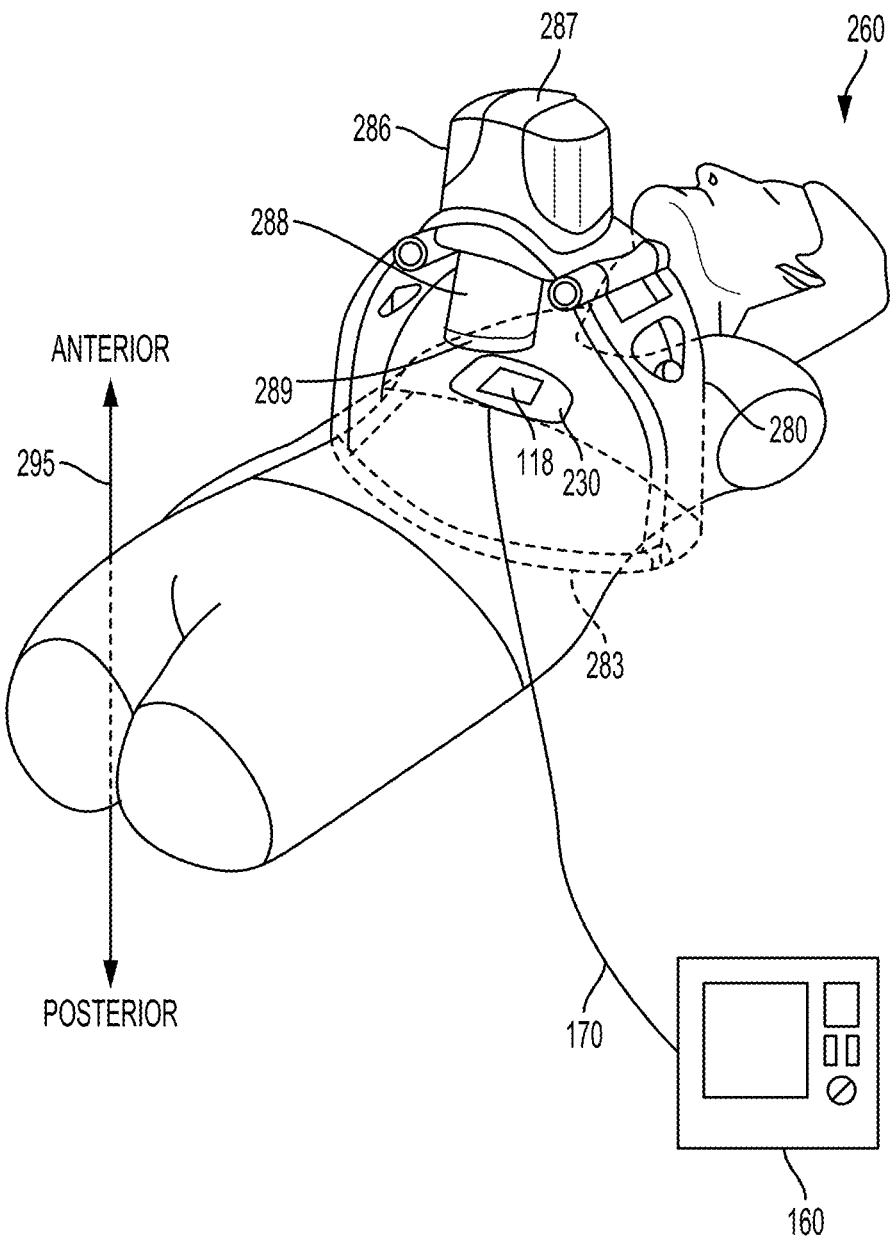
FIG. 2B is a schematic diagram of an example of a piston-based system for providing automated chest compressions to a victim.

Referring to FIG. 2B, a schematic diagram of an example of a piston-based system for providing automated mechanical chest compressions to a victim is shown. The automated piston-based CPR system 260 in FIG. 2B (e.g., the LUCAS® Chest Compression System) includes support arms 280, a backboard 283, a control unit 286, a motor housing 287, and a piston 288.

The control unit 286 is suspended above the chest of the victim by the support arms 280. The chest of the victim is supported by the backboard 283 and the victim is in a substantially supine position at least during the chest compressions. The control unit 286 may include a user input panel and/or status indicators for operations and/or components. One end of the piston 288 is coupled to a motor (not shown) within the motor housing 287. An opposite end of the piston 288 includes a compression pad 289. The compression pad 289 is in contact with the chest of the victim during chest compressions and decompressions. The control unit 286 sends a signal to the motor to control operations of the motor. The motor functions to drive the piston 288 towards the chest of the victim during downstroke of the chest compressions. The motor further functions to retract the piston 288 away from the chest of the victim during upstrokes of the chest compressions. The piston 288 moves along a compression axis substantially parallel to the anterior-posterior axis 295.

During operation, the compression pad 289 may contact an adhesive pad 230 releasably adhered to the skin of the victim. The adhesive pad 230 may include a liner and an adhesive face. The liner is configured to be removed or peeled away from the adhesive face by the rescuer in order to attach the adhesive pad 230 to the chest of the victim. The rescuer may remove the adhesive pad 230, for example, by applying a solvent to the adhesive pad 230 and/or peeling the adhesive pad 230 away from the patient's chest. The motion sensor 118 may be disposed within the adhesive pad 230. The motion sensor 118 may be coupled to the computing device 160 via a wired and/or wireless connection. As discussed in more detail below in reference to FIGS. 13A and 13B, the motion sensor 118 may be a component of a defibrillation electrode assembly and/or used in conjunction and/or coordination with a defibrillation electrode assembly.

Figure 3A:
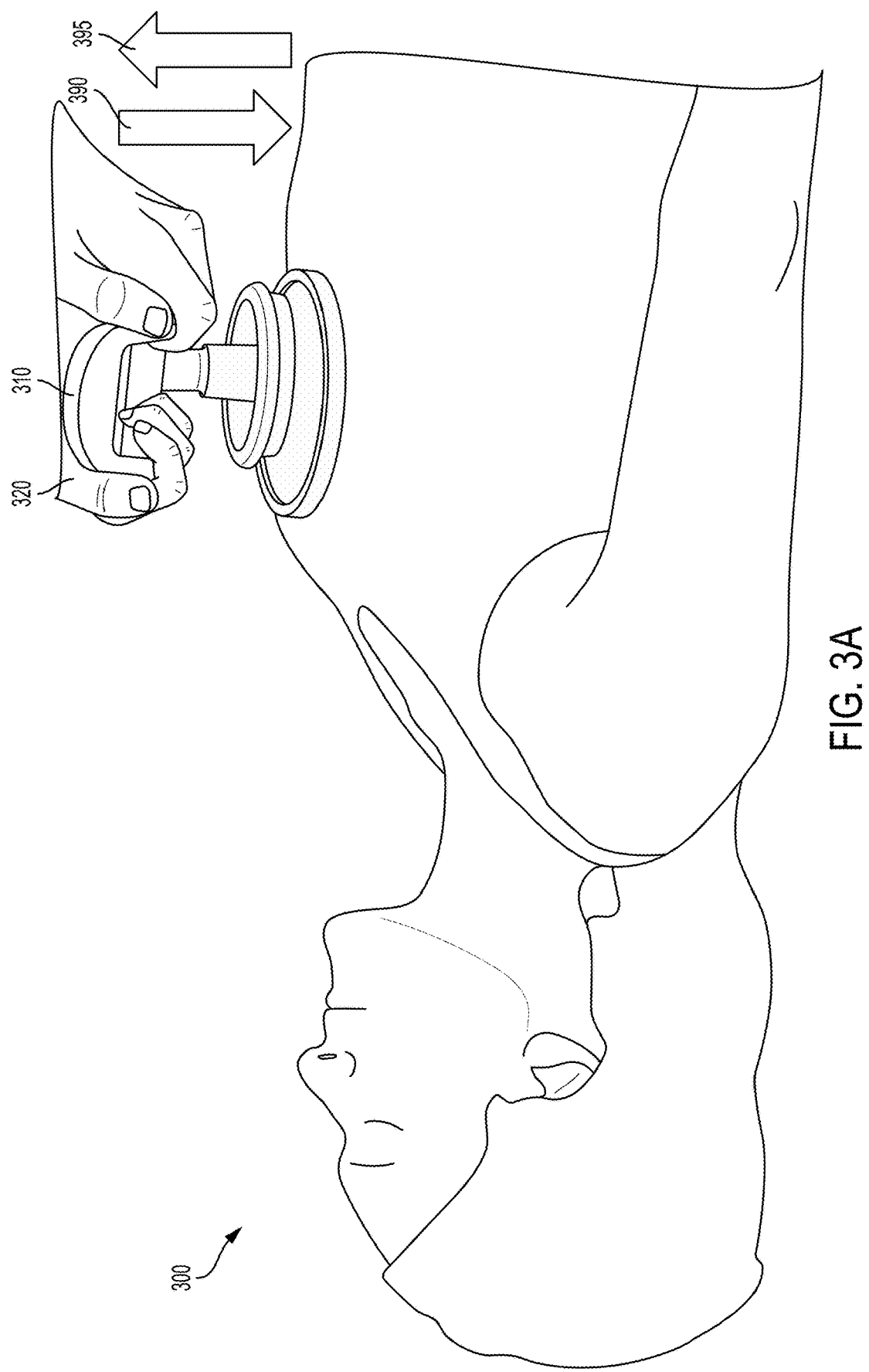
FIG. 3A is a schematic diagram of an example of a hand-held plunger system for providing mechanically assisted manual active chest compression decompression (ACD) to a victim.

Referring to FIG. 3A, a schematic diagram of an example of a hand-held plunger system for providing mechanically assisted manual ACD chest compressions to a victim is shown. The system 300 includes a hand-held ACD device 310 in the hands 320 of a rescuer (not shown). The hand-held ACD device 310 is shown held against the chest of the victim, interposed between the rescuer's hands and the victim's chest. The configuration and geometry of the hand-held ACD device 310 may enable the rescuer to use a similar body position and compression technique as in manual chest compressions. As illustrated in FIG. 3A, the hand-held ACD device 310 exerts a downward force (e.g., a force in the downward direction 390) on the chest to actively compress the chest. The hand-held ACD device 310 exerts an upward force (e.g., a force in the upward direction 395) to actively decompress the chest. Suction cups, adhesive pads, and/or other components configured to removably attach the hand-held ACD device 310 to the chest may enable the exertion of the upward force by the hand-held ACD device 310.

The hand-held ACD device 310 is configured to provide active compression and active decompression of the chest, to further enhance circulation throughout the body. For instance, active compression results in the application of positive intrathoracic pressure, leading to the ejection of blood out of the ventricles and away from the heart. Active decompression, on the other hand, results in the application of negative intrathoracic pressure, which enhances venous return back to the heart. In the absence of active decompression, the chest passively returns to its neutral position during the release phase (i.e., the decompression phase) of the chest compression cycle. The neutral position is defined as a position of the sternum when no force, either upward or downward, is applied to the chest. The exertion of the upward force (i.e., the active decompression) may increase the release velocity associated with the decompression as compared to the release velocity without active decompression. Such an increase in the release velocity may increase the negative intrathoracic pressure and thereby enhance venous flow into the heart and lungs from the peripheral venous vasculature of the patient. In other words, the active decompression may enhance venous return of blood to the heart to refill the cardiac chambers. The active decompression may also enhance ventilation in the patient's lungs.

Figure 3B:
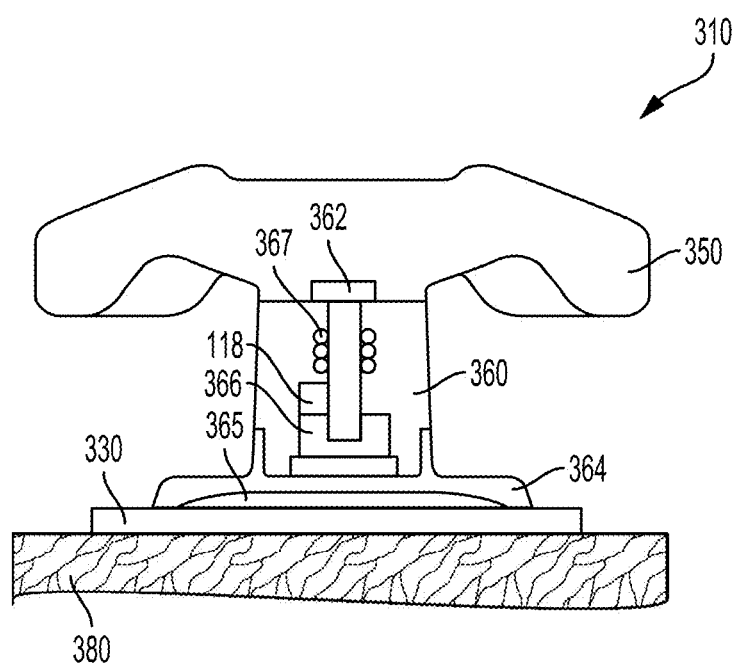
FIG. 3B is a schematic diagram of an example of a cross-section of the hand-held ACD device of FIG. 3A.

Referring to FIG. 3B, a schematic diagram of an example of a cross-section of the hand-held ACD device of FIG. 3A is shown. The hand-held ACD device 310 includes a handle 350, an applicator body 360, and a coupling surface 364. The coupling surface 364 may include one or more suction cups 365. The coupling surface 364 may contact a compression target pad 330 releasably affixed to the skin 380 of the patient. The applicator body 360 is configured to releasably attach to the coupling surface 364. For example, a coupling assembly 366 may releasably attach the applicator body 360 to the coupling surface 364. The coupling assembly 366 may include, for example, but not limited to, a magnetic coupling assembly, a ball and socket joint, a cantilevered arm, or a detent mechanism. The coupling assembly may be configured to provide a consistent release force over a range of operating conditions. Further, the coupling assembly may enable the applicator body 360 to separate from the coupling surface 364 if the upward force exceeds a desired force (e.g., the desired force may be a maximum force to reduce damage to the patient's skin). The hand-held ACD device 310 may further include one or more force sensors 362 and/or one or more pressure sensors and a battery and associated circuitry (not shown). The spring 367 may function as a component of a pressure gauge and/or as a shock absorber to help prevent the rescuer from applying an excessive force to the chest of the patient.

During a compression phase of a CPR chest compression cycle, the rescuer may push on the handle 350 of the hand-held ACD device 310 in the downward direction 390. The downward force exerted by the hand-held ACD device 310 on the chest may be sufficient to compress the chest and induce arterial blood circulation by ejecting blood from cardiac chambers. During the active decompression, the rescuer may pull on the handle 350 of the hand-held ACD device 310 in the upward direction 395. The downward and upward strokes may be repeated (i.e., multiple CPR chest compression cycles with each cycle including a downward stroke and an upward stroke) at a rate determined to optimally enhance blood circulation and ventilation.

The motion sensor 118 may be disposed within the hand-held ACD device 310 and/or the rescuer's hands 320 may hold the motion sensor 118. For example, the rescuer may hold the motion sensor 118 against the handle 350 during use of the hand-held ACD device 310. Additionally or alternatively, the motion sensor 118 may be disposed on the chest of the patient as described below with regard to FIGS. 3C and 3D.

Figure 3C:
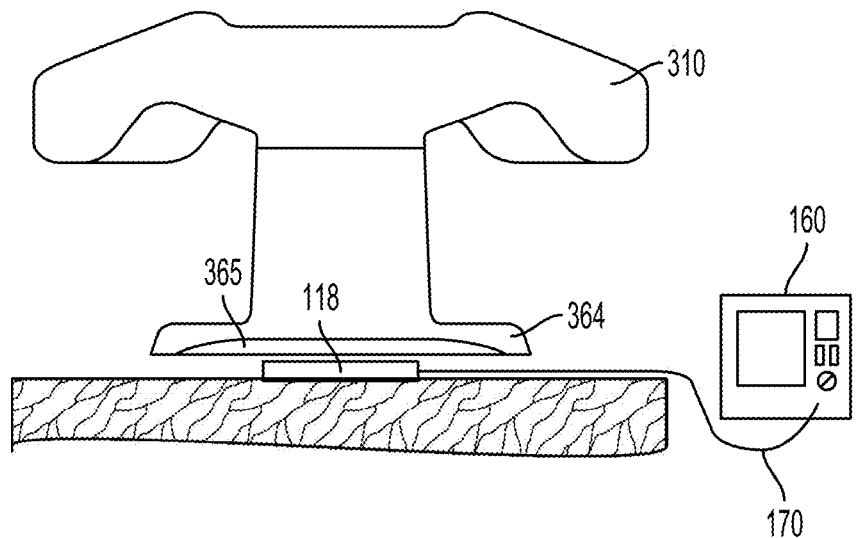
FIGS. 3C and 3D are schematic diagrams of examples of motion sensor configurations for the hand-held ACD device of FIG. 3A.
Figure 3D:
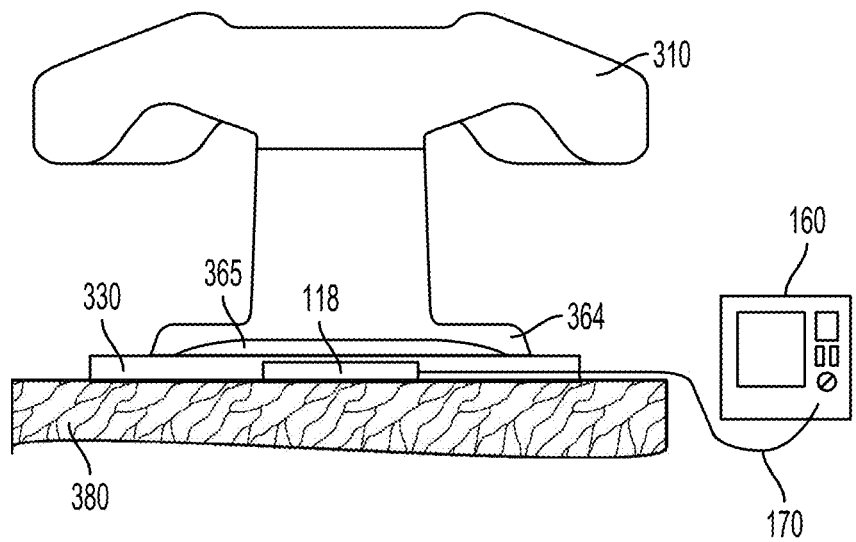

Referring to FIGS. 3C and 3D, schematic diagrams of examples of motion sensor configurations for the hand-held ACD device of FIG. 3A are shown. As shown in FIG. 3C, during operation, the coupling surface 364 may cover and surround the motion sensor 118 disposed on the chest of the victim. The motion sensor 118 may be coupled to the computing device 160 via the connection 170 (e.g., a wired and/or wireless connection). Alternatively, as shown in FIG. 3D, the motion sensor 118 may be disposed within the compression target pad 330. The compression target pad 330 may be an adhesive pad, for example, the adhesive pad 230 as described above. The compression target pad 330 may be releasably adhered to the skin 380 of the victim. During operation, the coupling surface 364 may contact the compression target pad 330. The configuration of FIG. 3D provides an advantage of eliminating interference of any wires from the motion sensor 118 with the operation of the one or more suction cups 365. As discussed in more detail below in reference to FIGS. 13A and 13B, the motion sensor 118 may be a component of a defibrillation electrode assembly and/or used in conjunction and/or coordination with a defibrillation electrode assembly.

In an implementation, the hand-held ACD device may include multiple motion sensors configured to measure upward and downward motion of the chest. For example, a first motion sensor (e.g., the motion sensor disposed in the hand-held device and/or in the rescuer's hands) may measure the downward acceleration of the chest during compression. A second motion sensor (e.g., the disposed on the chest) may be positioned near the suction cup of the hand-held ACD device and may measure the upward acceleration of the chest during active decompression.

A surface of the compression target pad 330 may include a layer of high-traction or anti-slip material to enable the compression target pad 330 to remain attached to the patient's skin 380 during CPR treatment. The dimensions of compression target pad 330 may be based on a desired contact area with the patient's chest. For example, a larger area of the compression target pad 330 may increase an amount of chest expansion as compared to a smaller area of the compression target pad 330. As another example, a pediatric adhesive pad may be smaller than an adult adhesive pad. The thickness of the compression target pad 330 may depend on a resiliency of materials that form the compression target pad 330. The shape of the compression target pad 330 may vary based on expected chest contours for potential victims.

The hand-held ACD device 310 described above is an example of a mechanically assisted manual compression device. An automated system may also provide ACD chest compressions. For example, referring again to FIG. 2B, the compression pad 289 of the piston-based compression device may include one or more suction cups or other mechanical devices configured to pull up on the chest of the victim during the release phase of the CPR cycle. In this case, the piston-based compression device may provide automated ACD chest compressions.

Figure 4:
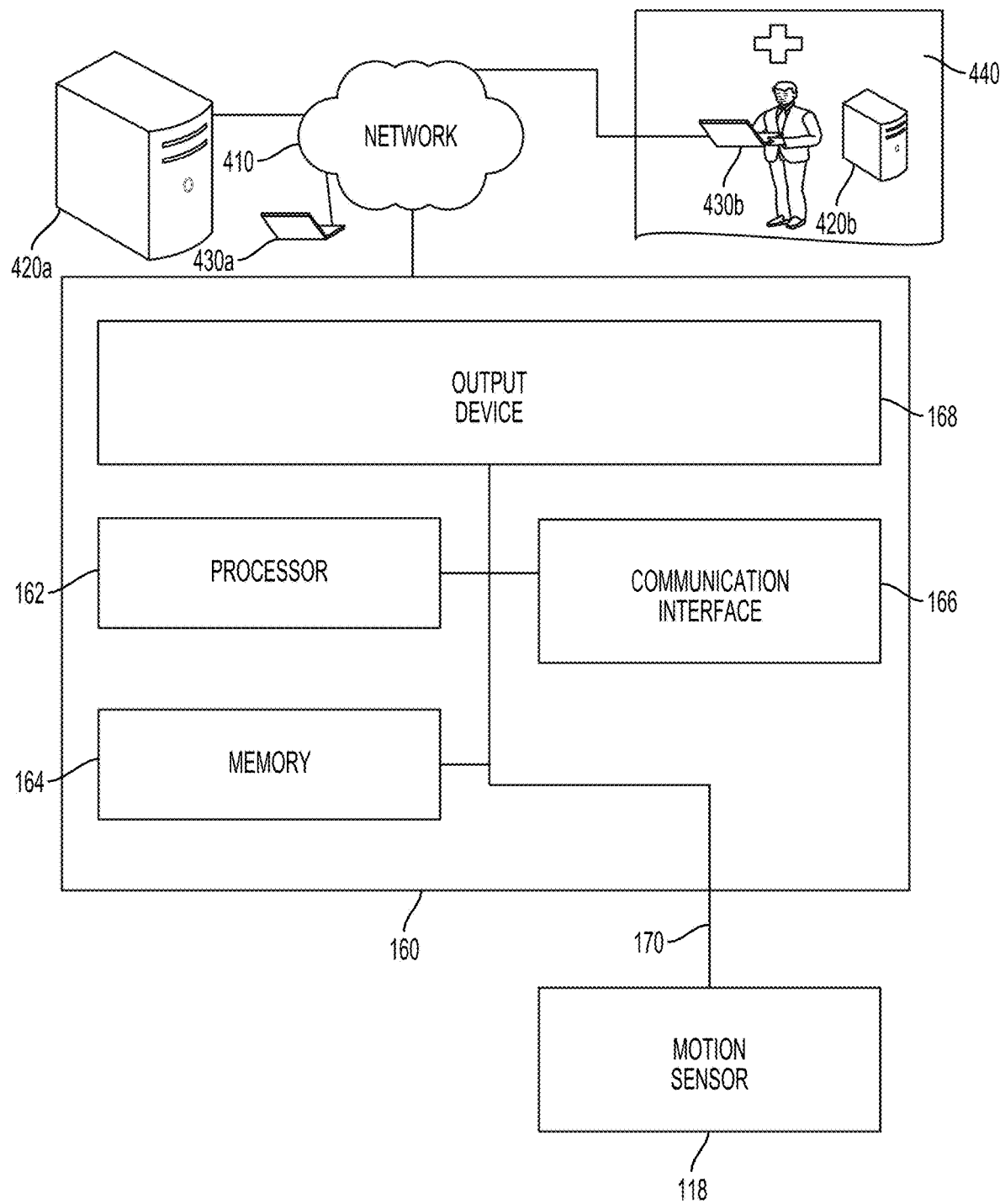
FIG. 4 is a block diagram of hardware components of the computing device from FIGS. 1, 2A, 2B, and 3A.

Referring to FIG. 4, a block diagram of hardware components of the computing device from FIGS. 1-3 is shown. The computing device 160 may be for example, but not limited to, a personal computer, a laptop computer, a mobile device, a hand-held device, a wireless device, a tablet, a medical device, a defibrillator (e.g., the defibrillator 1210 discussed with regard to FIG. 12, the defibrillator 1400 discussed with regard to FIG. 14, or the defibrillator 1500 discussed with regard to FIG. 15), a patient monitor, a wearable device (e.g., a wrist-worn device, a head-worn device, etc.), or combinations thereof. The computing device 160 may be a group of communicatively coupled devices. Claimed subject matter is not limited to a particular type, category, size, etc. of computing device. The computing device 160 may include a processor 162, a memory 164, an output device 168, and a communications interface 166. As described in further detail below, with regard to FIGS. 13A and 13B, in an implementation, the computing device 160 may be a defibrillator. The computing device 160 may include a user input device (e.g., a touch screen, a keyboard, a mouse, joystick, trackball, or other pointing device, a microphone, a camera, etc.).

The processor 162 is a physical processor (i.e., an integrated circuit configured to execute operations on the computing device 160 as specified by software and/or firmware). The processor 162 may be an intelligent hardware device, e.g., a central processing unit (CPU), one or more microprocessors, a controller or microcontroller, an application specific integrated circuit (ASIC), a general-purpose processor, a digital signal processor (DSP), or other programmable logic device, a state machine, discrete gate or transistor logic, discrete hardware components, or any combination thereof designed to perform the functions described herein and operable to carry out instructions on the computing device 160. The processor 162 utilize various architectures including but not limited to a complex instruction set computer (CISC) processor, a reduced instruction set computer (RISC) processor, or a minimal instruction set computer (MISC). In various implementations, the processor 162 may be a single-threaded or a multi-threaded processor. The processor 162 may be one or more processors and may be implemented as a combination of computing devices (e.g., a combination of DSP and a microprocessor, a plurality of microprocessors, one or more microprocessors in conjunction with a DSP core, or any other such configuration). The processor 162 may include multiple separate physical entities that may be distributed in the computing device 160. The processor 162 is configured to execute processor-readable, processor-executable software code containing one or more instructions or code for controlling the processor 162 to perform the functions as described herein.

The processor 162 is operably coupled to the memory 164. The memory 164 refers generally to any type of computer storage medium, including but not limited to RAM, ROM, FLASH, disc drives, fuse devices, and portable storage media, such as Universal Serial Bus (USB) flash drives, etc. The USB flash drives can store operating systems and other applications. The USB flash drives can include input/output components, such as a wireless transmitter and/or USB connector that can be inserted into a USB port of another computing device. The memory 164 may be long term, short term, or other memory associated with the computing device 160 and is not to be limited to any particular type of memory or number of memories, or type of media upon which memory is stored. The memory 164 includes a non-transitory processor-readable storage medium (or media) that stores the processor-readable, processor-executable software code.

The communications interface 166 may transmit and/or receive information from and/or to one or more computing devices external to the computing device 160. The communications interface 166 may transmit and/or receive the information via a wired and/or a wireless communicative connection to the one or more external computing devices via a network 410. The information may include information stored in the memory 164 of the computing device 160. The information may include, for example, but not limited to, resuscitative treatment information, patient information, rescuer information, location information, rescue and/or medical treatment center information, etc. The resuscitative treatment information may include an indication of the identification of the compression waveform. The network 410 may be, for example, but not limited to, a local area network, a cellular network, and/or a computer network (e.g., an Internet Protocol network). The communications interface 166 may provide Wi-Fi, Bluetooth®, satellite, and/or cellular communications capabilities. The one or more external computing devices may include a server 420a and/or another computing device 430a (e.g., a personal computer, a laptop computer, a mobile device, a hand-held device, a wireless device, a tablet, a medical device, a defibrillator, a patient monitor, a wearable device (e.g., a wrist-worn device, a head-worn device, etc.), or combinations thereof. The server 420a may be a cloud server or central facility server. The one or more external computing devices may additionally and/or alternatively include a server 420b and/or a computing device 430b associated with a medical provider 440 (e.g., a hospital, a physician's office, a medical records office, an emergency services office, an emergency services vehicle, a dispatch center, etc.).

The output device 168 may be a one or more of a display, a speaker, and a haptic device. The display may provide a graphical user interface (GUI). The display may be, for example, but not limited to, a liquid crystal display (LCD) and/or a light emitting diode (LED) display. In an implementation the output device 168 may be an input/output device capable of capturing user input (e.g., a touch screen). The processor 162 may control the output device 168 to provide one or more of visible feedback, audible feedback, haptic feedback, numerical feedback, and graphical feedback. The feedback may include chest compression parameter feedback and/or resuscitative care feedback. Alternatively, or additionally, the processor 162 may control the output device 168 to provide instructions, alarms, treatment event reminders, treatment event timing information, and/or combinations thereof. The processor 162 may further control the output device 168 to provide resuscitative care prompts and/or instructions for the rescuer. For example, the resuscitative care prompts may include one or more of a prompt to start resuscitative treatment, a prompt to determine if the victim requires CPR, a prompt to start the manual chest compressions, a prompt to determine if the rescuer wants to provide the automated chest compressions, a prompt to attach an automated chest compression device to the victim, and a prompt to determine if the rescuer wants to continue CPR.

The output device 168 may be a component of the computing device 160. Alternatively, or additionally, the output device 168 may be a discrete component communicatively coupled to the computing device 160. The communicative coupling between the output device 168 and the computing device 160 may be include wired and/or wireless connections.

The components 162, 164, 166, and 168 are communicatively coupled (directly and/or indirectly) to each other for bi-directional communication. Although shown as separate entities in FIG. 4, the components 162, 164, 166, and 168 may be combined into one or more discrete components and/or may be part of the processor 162. The processor 162 and the memory 164 may include and/or be coupled to associated circuitry in order to perform the functions described herein.

The motion sensor 118 may be an accelerometer and the one or more signals indicative of the motion of the chest 140 of the victim 150 may be acceleration signals. The accelerometer may be a single accelerometer configured to detect and measure acceleration of the compression puck 110 along the compression axis approximately parallel to the anterior-posterior axis 195 of the victim 150. Alternatively, the motion sensor 118 may include two or three accelerometers. The two or three accelerometers may form a multi-accelerometer assembly or may be separate accelerometers. The two or three accelerometers may be configured to detect and measure acceleration of the compression puck 110 along two or three orthogonal axes with at least one of the orthogonal axes approximately parallel to the compression axis. The acceleration signals correspond to acceleration of the chest 140, at least along the compression axis, during the chest compressions. In various implementations, the motion sensor 118 may be one or more of a velocity sensor, a displacement sensor, and a force sensor.

The connection 170 between the motion sensor 118 and the computing device 160 is shown as a wired connection in FIG. 4. However, this is an illustrative example only and not limiting of the disclosure. The motion sensor 118 may provide the one or more signals indicative of the chest motion to the computing device 160 via a wired and/or wireless connection. The motion sensor 118 may be disposed, for example, in the compression puck 110, the compression belt 210, the adhesive pad 230, the compression target pad 330, or the hand-held ACD device 310. As a further example, and as discussed in more detail below in reference to FIGS. 13A and 13B, the motion sensor 118 may be a component of a defibrillation electrode assembly.

In the above examples, the motion sensor 118 is physically separate from the computing device 160. However, in various implementations, the computing device 160 may be a compression monitor, a smart-phone or other hand-held device, and/or a wearable device. In these cases, the computing device 160 may include the motion sensor 118 (e.g., the motion sensor 118 may be a component of or physically attached to the computing device 160). For example, the computing device 160 may be a cell phone that includes the motion sensor 118, configured to be held in between the hands of the rescuer during manual CPR compressions.

Figure 5:
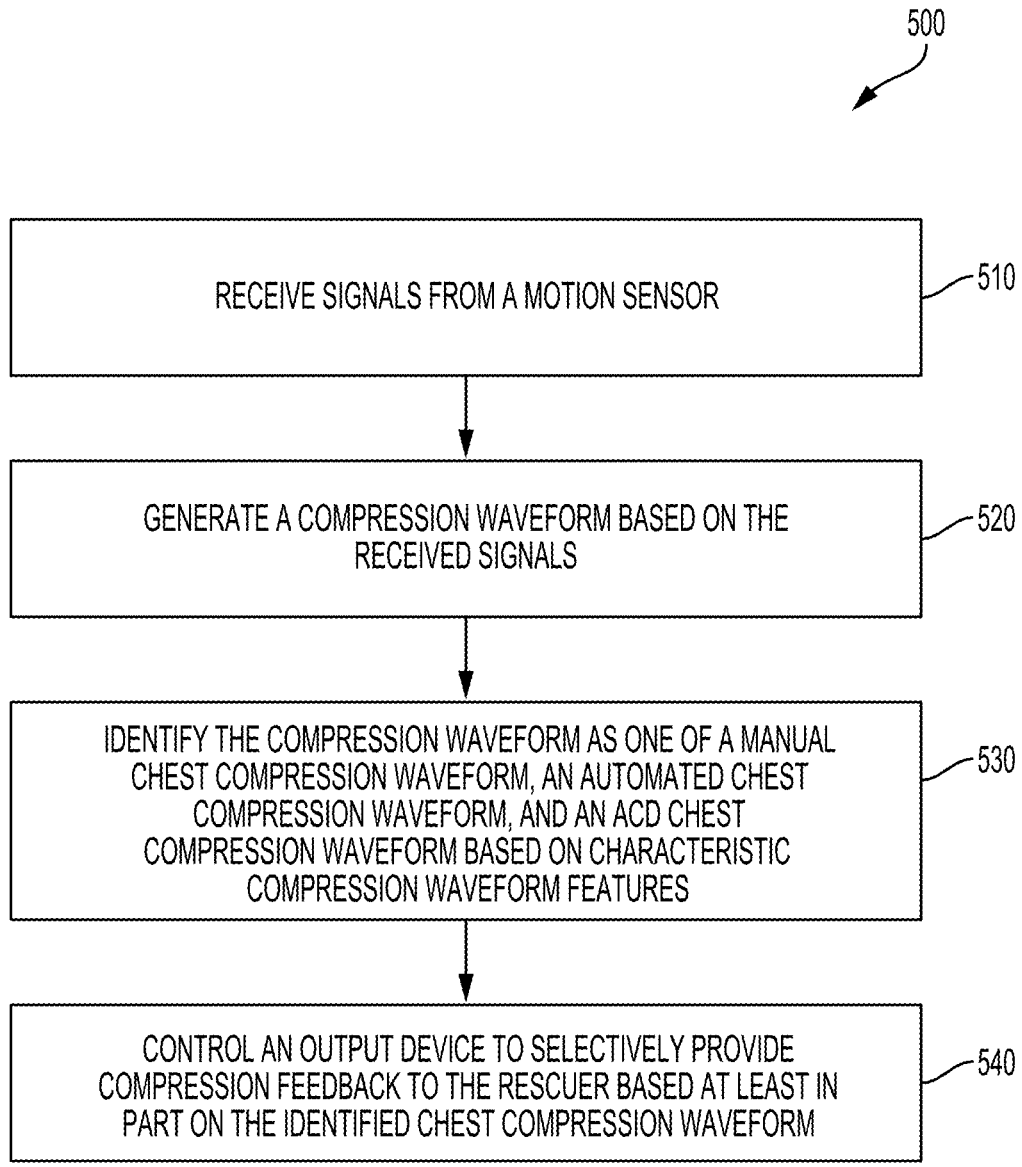
FIG. 5 is a block diagram of a method of assisting a rescuer in providing resuscitative treatment to a victim.

Referring to FIG. 5, a method of assisting a rescuer in providing resuscitative treatment to a victim is shown. The method 500 is, however, an example only and not limiting. The method 500 can be altered, e.g., by having stages added, removed, rearranged, combined, and/or performed concurrently.

Figure 6A:
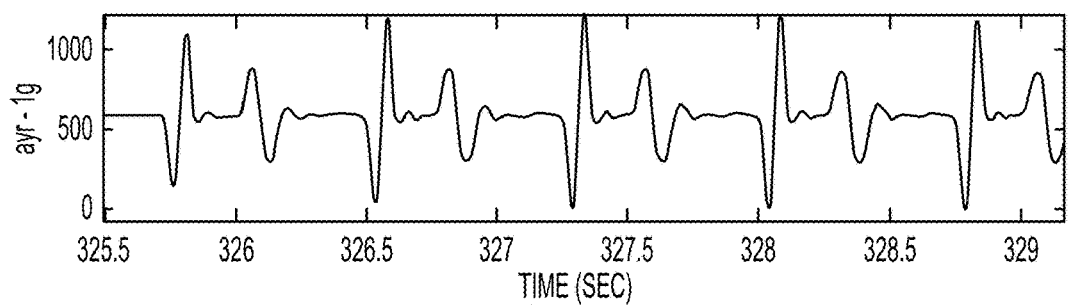
FIGS. 6A-6E are examples of received and processed motion sensor signals representative of automated chest compressions.
Figure 7A:
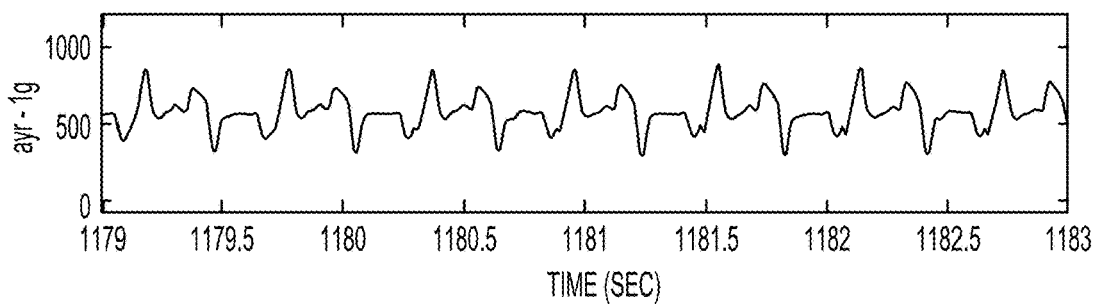
FIGS. 7A-7E are examples of received and processed motion sensor signals representative of the hand-held ACD device chest compressions.
Figure 8A:
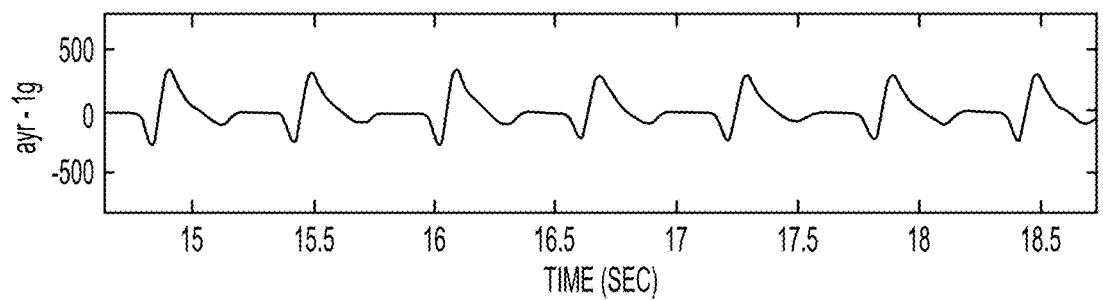
FIGS. 8A-8E are examples of received and processed motion sensor signals representative of the manual chest compressions.

At stage 510, the method 500 includes receiving signals from a motion sensor. For example, the processor 162 is configured to receive the one or more signals indicative of the motion of the chest from the motion sensor 118. In an implementation, the motion sensor 118 may be an accelerometer and the one or more signals may be acceleration signals. The processor 162 may receive the acceleration signals as shown, for example, in FIG. 6A for automated chest compressions, FIG. 7A for hand-held ACD device chest compressions, and FIG. 8A for manual chest compressions. In all of these figures, the x-axis corresponds to time and the y-axis corresponds to a signal magnitude.

Figure 6B:
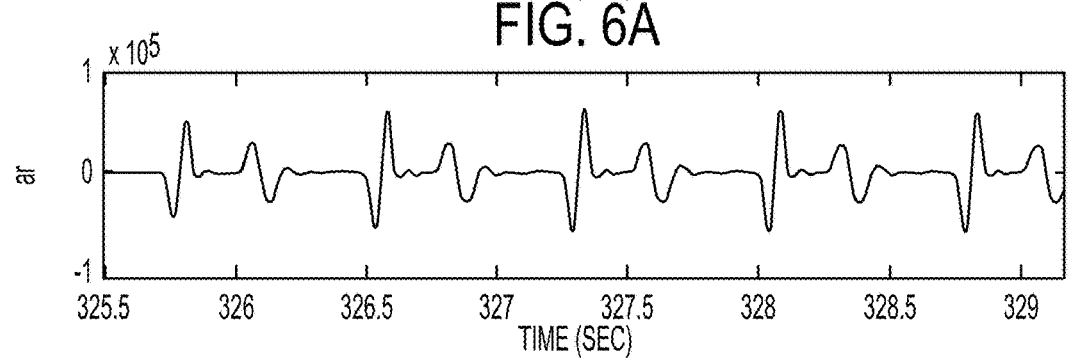
Figure 6C:
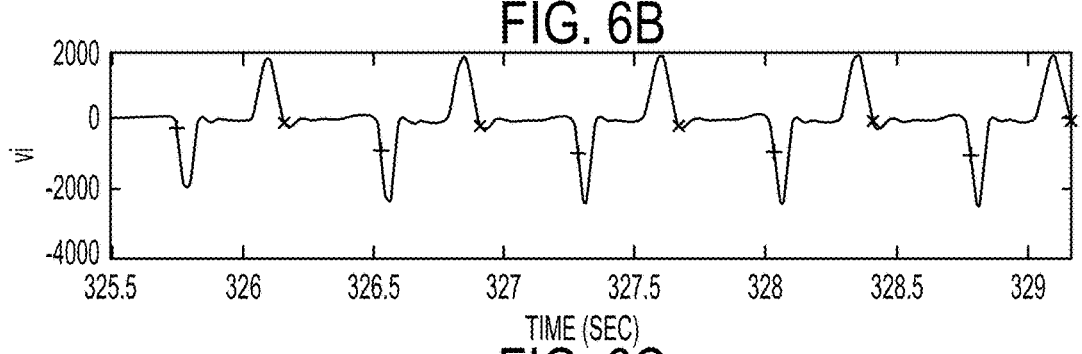
Figure 6D:
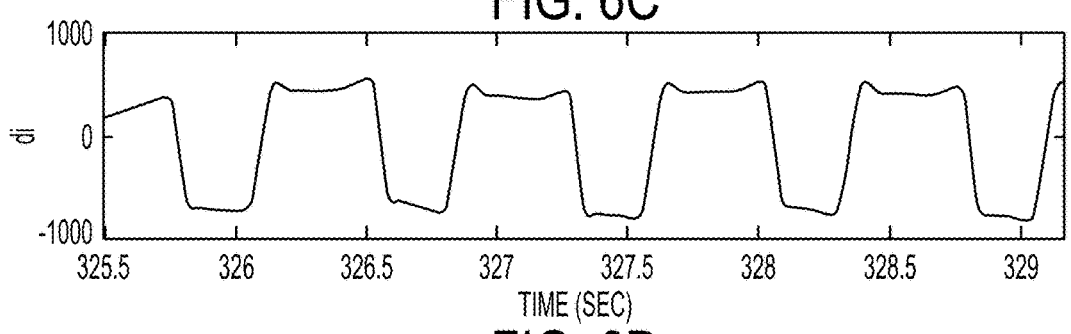
Figure 7B:
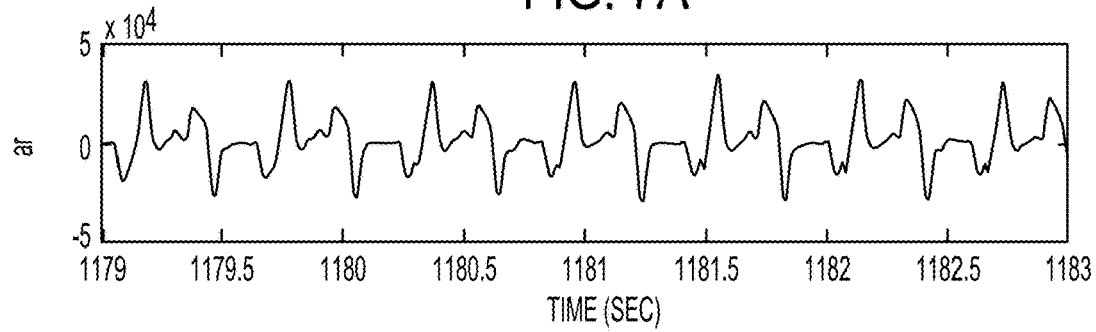
Figure 7C:
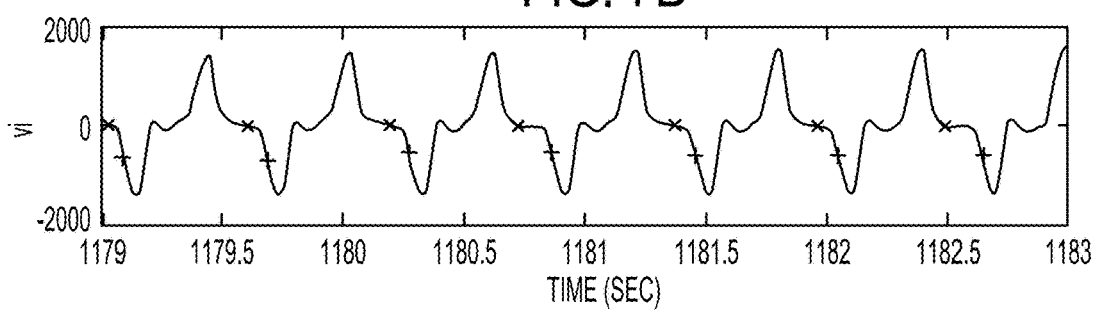
Figure 7D:
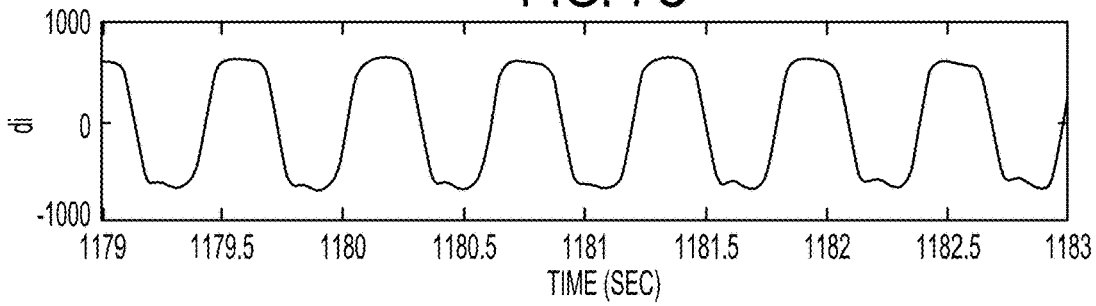
Figure 8B:
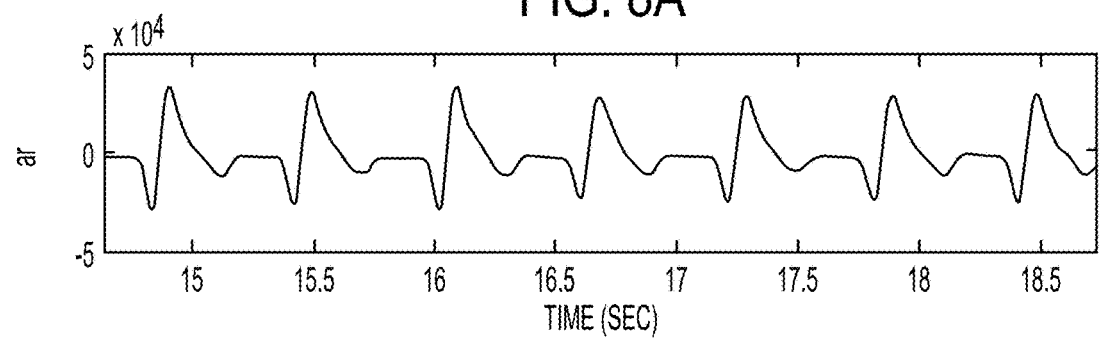
Figure 8C:
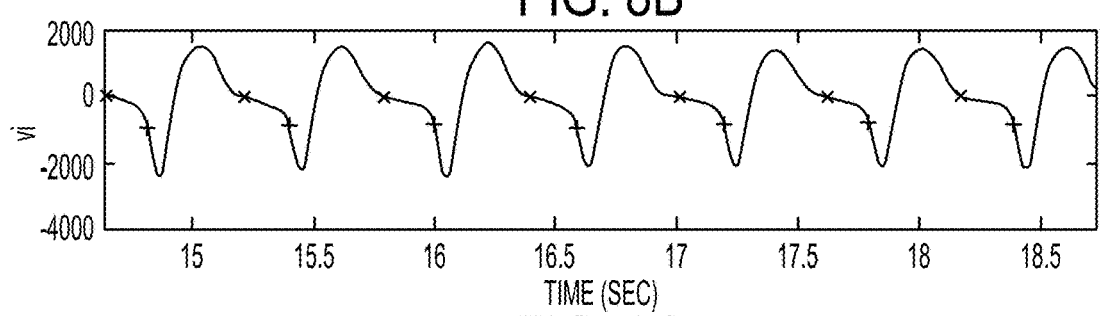
Figure 8D:
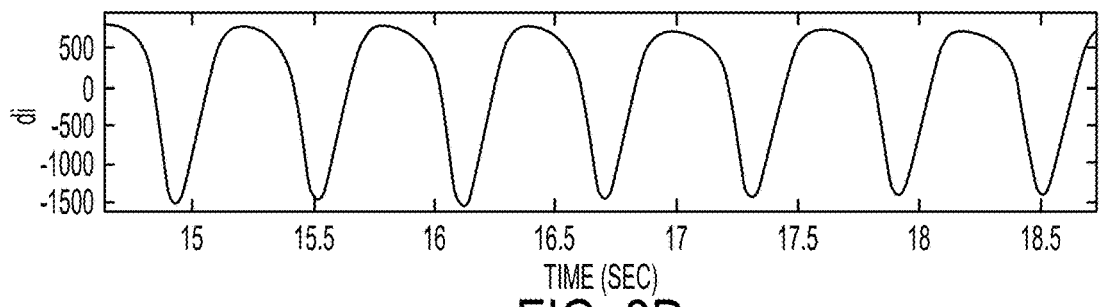

Referring again to FIG. 5, at stage 520, the method 500 includes generating a compression waveform based on the received signals. For example, the processor is configured to generate one or more compression waveforms based on the one or more signals indicative of the motion of the chest as received from the motion sensor 118. The processor 162 may apply a filter (e.g., a high-pass filter configured to remove a baseline) to the acceleration signals to determine a filtered acceleration waveform as shown, for example, in FIG. 6B for automated chest compressions, FIG. 7B for hand-held ACD device chest compressions, and FIG. 8B for manual chest compressions. In these examples, the filter is a high pass filter however other filters are within the scope of the disclosure. The processor 162 may integrate the acceleration waveform once to determine a velocity waveform. Examples of velocity waveforms are shown in FIG. 6C for automated chest compressions, FIG. 7C for hand-held ACD device chest compressions, and FIG. 8C for manual chest compressions. The processor 162 may integrate the acceleration waveform twice to determine a displacement waveform. Examples of displacement waveforms are shown in FIG. 6D for automated chest compressions, FIG. 7D for hand-held ACD device chest compressions, and FIG. 8D for manual chest compressions.

At stage 530, the method 500 includes identifying the compression waveform as one of a manual chest compression waveform, an automated chest compression waveform, and an ACD chest compression waveform. For example, the processor 162 may evaluate the compression waveform for quantitative and/or qualitative features characteristic of a particular compression delivery system. The processor 162 is configured (e.g., based on instructions stored in the memory 164 and/or the hardware topology of the processor and associated circuitry) to detect waveform features characteristic of one or more of a manual chest compression waveform, an automated chest compression waveform, an automated ACD chest compression waveform, and an ACD chest compression waveform. Based on the detected features, the processor 162 may identify the type of compression waveform (e.g., a manual chest compression waveform, an automated chest compression waveform, an ACD chest compression waveform, etc.).

Figure 6E:
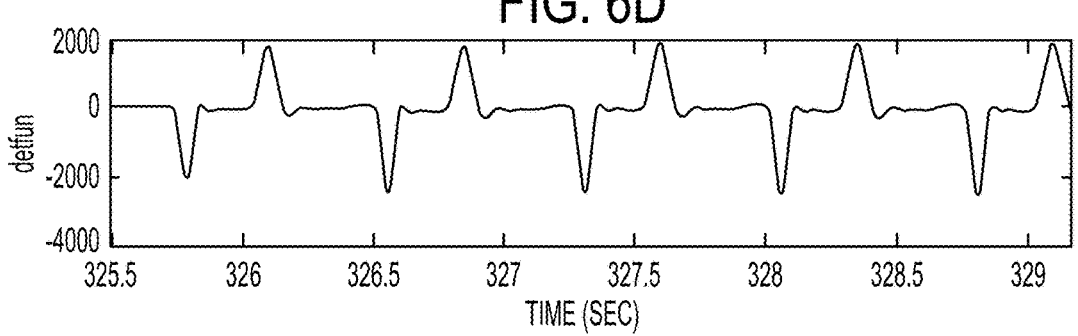
Figure 7E:
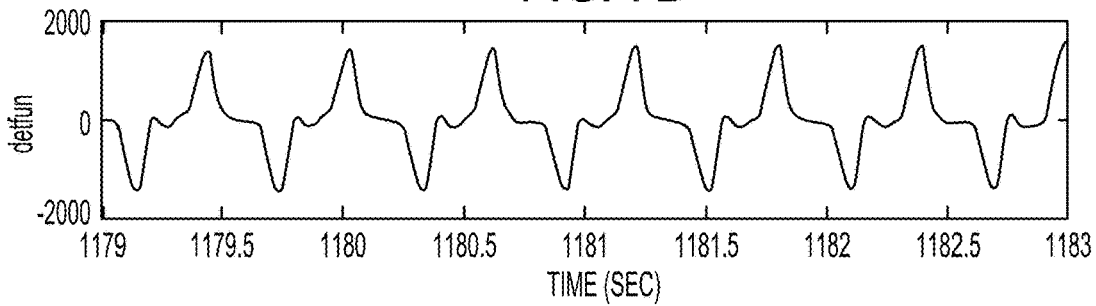
Figure 8E:
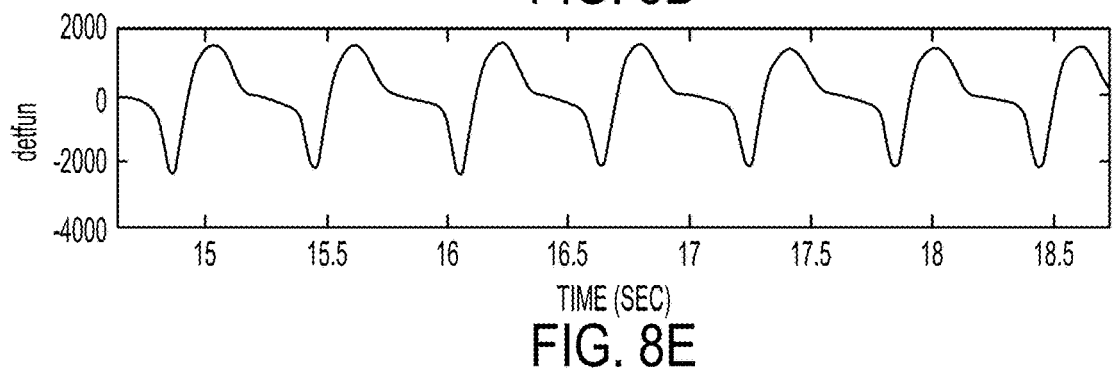

The processor 162 may detect the characteristic features based on identified compression cycles in the compression waveform. In order to identify the compression cycles, the processor 162 may apply signal analysis methods to the compression waveform. The processor 162 may apply the signal analysis to identify the beginning and end of each compression cycle within the compression waveform. The processor 162 may further apply the signal analysis to identify various portions of one or more of the compression cycles (e.g., various phases of the compression cycle such as the downstroke, the upstroke, etc.). The processor 162 may apply the signal analysis to the acceleration waveform, the velocity waveform, the displacement waveform, and/or combinations thereof. As an example, the signal analysis may include one or more of band pass filtering, rectification, and/or threshold analysis. The threshold analysis may distinguish features in the compression waveforms due to compressions from features in the compression waveforms due to noise and/or motion of the patient and/or the motion sensor not caused by compressions (e.g., vibrations of a gurney and/or an ambulance). The threshold analysis may compare peaks in a signal to a threshold amplitude. Peaks in the measured signal that are below the threshold amplitude may correspond to the noise and/or the motion of the patient and/or the motion sensor not caused by compressions. Examples of compression detection waveforms from the velocity waveforms are shown in FIG. 6E for automated chest compressions, FIG. 7E for hand-held ACD device chest compressions, and FIG. 8E for manual chest compressions. Using the threshold analysis, the processor 162 may identify individual compression cycles within a series of compression cycles from the velocity waveform. The threshold analysis determines differences between a waveform magnitude sampled over a sample time interval and a threshold magnitude. Additionally, the threshold analysis determines differences in the waveform magnitude sampled between sample time intervals. In this manner, the threshold analysis may identify the beginning and the end of each compression cycle in the series of compression cycles. As discussed herein, a single chest compression cycle includes a downstroke and an upstroke. The downstroke may also be referred to as a compression phase of the CPR cycle. The upstroke may also be referred to as a release phase and/or a decompression phase of the CPR cycle.

Once the processor 162 identifies the compression cycles within the waveforms, the processor 162 may detect waveform features characteristic of various types of chest compressions. For example, the various types of chest compressions may include those listed above in Table 1.

Figure 9A:
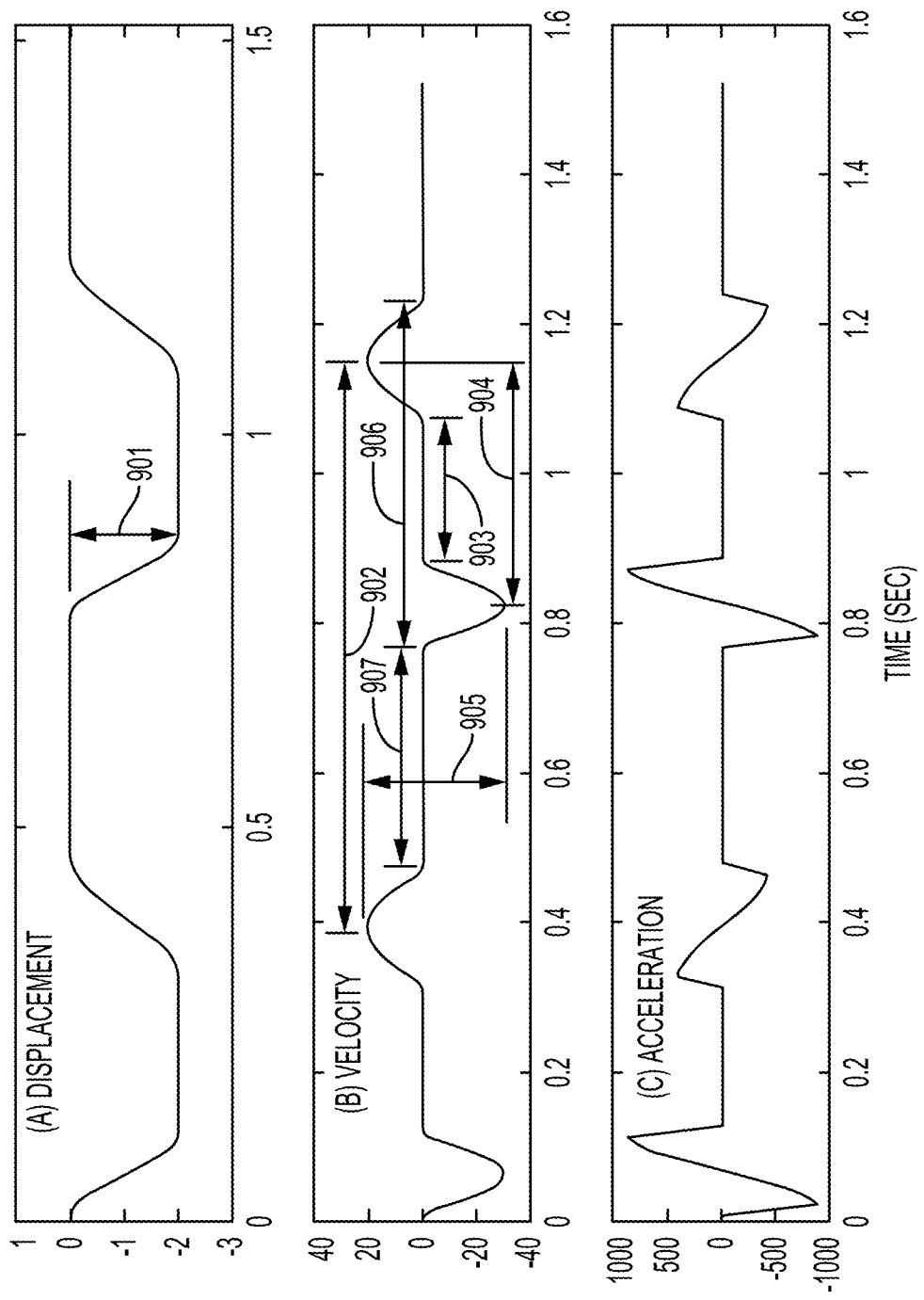
FIG. 9A is an example of waveform features characteristic of automated chest compressions.
Figure 9B:
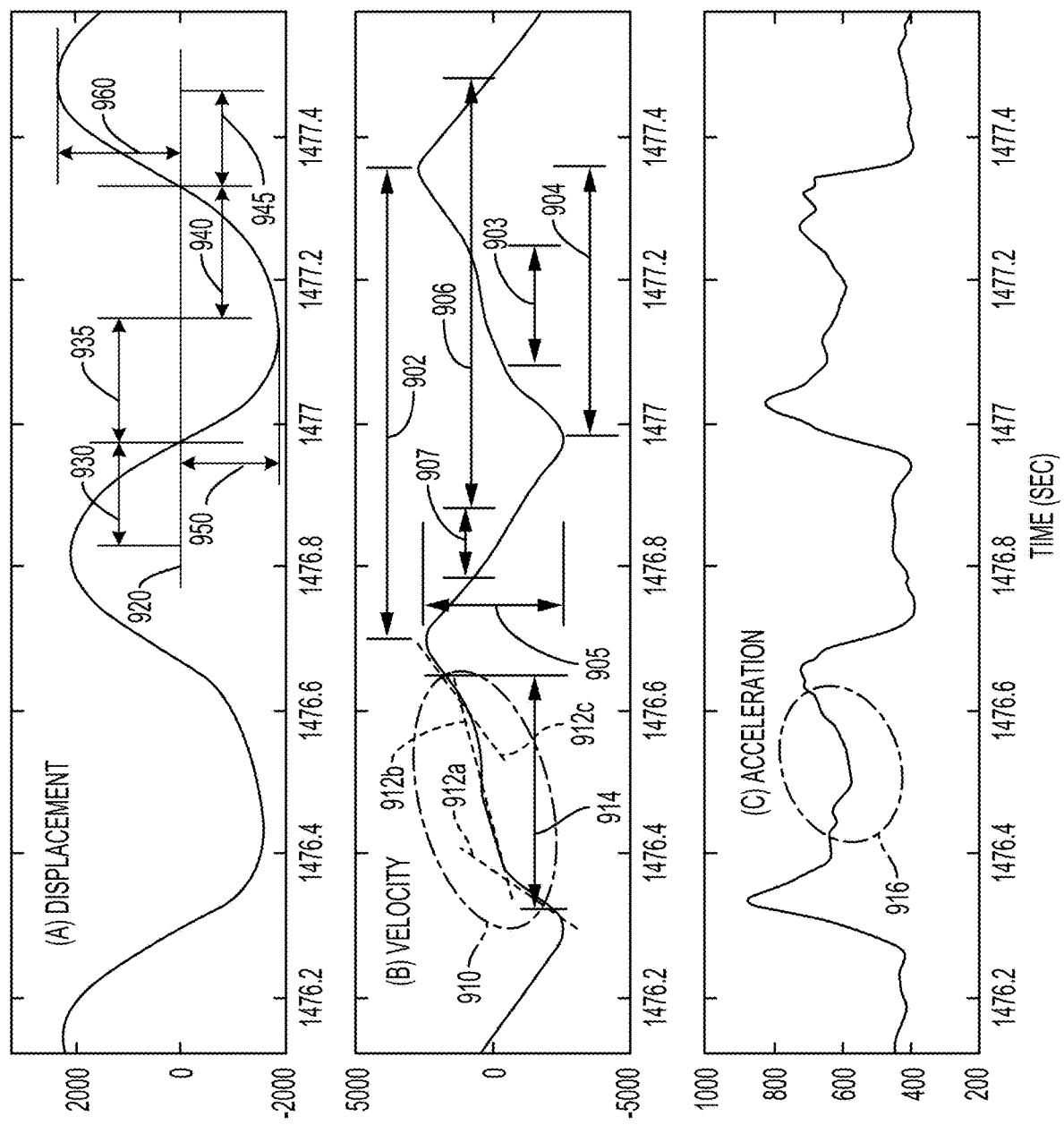
FIG. 9B is an example of waveform features characteristic of hand-held ACD device chest compressions.
Figure 9C:
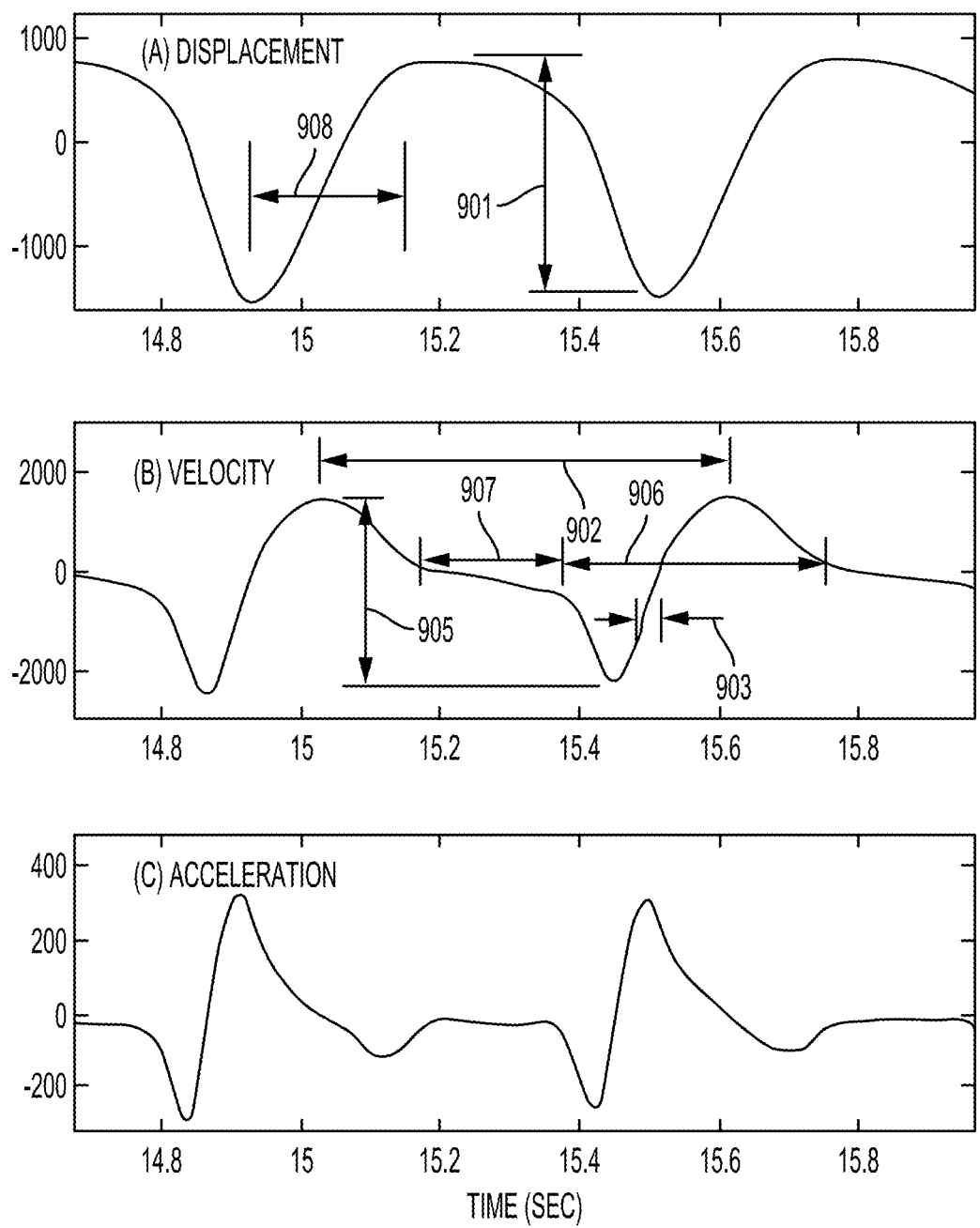
FIG. 9C is an example of waveform features characteristic of manual chest compressions.

Referring to FIGS. 9A, 9B, and 9C, examples of waveform features characteristic of automated chest compressions, manual chest compressions, and hand-held ACD device chest compressions, respectively, are shown. The compression depth (feature 901) is a measure of chest displacement as indicated by the peak to trough amplitude difference on a displacement waveform within a compression cycle. The compression rate (feature 902) is a number of compression cycles per unit time. The hold time (feature 903) is a time interval within the compression cycle between the downstroke and the successive upstroke. The velocity minimum-to-maximum time (feature 904) is the time interval on the velocity waveform from a velocity waveform trough to a successive velocity waveform peak within the compression cycle. The velocity amplitude (feature 905) is the difference on the velocity waveform between the amplitude of a velocity waveform peak and the amplitude of a successive velocity waveform trough. The compression width (feature 906) is the time interval between the onset of a compression and the end of a compression (i.e., the time interval between the start of the downstroke and the end of the upstroke for the compression cycle). The relaxation time (feature 907) is the time interval between compression cycles (i.e., the time interval between the end of the upstroke of a first compression cycle and the start of the downstroke for a second, successive compression cycle). The release time (i.e., the decompression time) (feature 908) is the time interval from the beginning to the end of an upstroke. Features 901, 902, 903, 906, 907, and 908 are indicated on the velocity waveforms in FIGS. 9A-9C as illustrative examples. The processor 162 may evaluate these features on one or more of the displacement waveform, the velocity waveform, and the acceleration waveform. The processor 162 may select the particular waveform for evaluation based on the clarity of the features in the selected waveform as compared to the other waveforms and/or as compared to signal noise.

For each of the features discussed in FIGS. 9A-9C, expected values or ranges of values for these features may be associated with the particular types of the chest compressions. Examples, not limiting of the disclosure, of values and value ranges for the features discussed above are shown below in Table 2 for automated belt-based compressions and for manual compressions. Other values are consistent with the disclosure and the examples given below are not limiting.

TABLE 2

COMPRESSION WAVEFORM FEATURES

| Compression Type | Belt-based | Manual |
|---|---|---|
| Compression Rate (901) | 77-83 cpm | <206 cpm |
| Compression Depth (902) | 1-6 inches (2.5-15 cm) | 0.33-7 inches (0.84-17.7 cm) |
| Hold Time (903) | ≥120 msec | ≤600 msec |
| Velocity Minimum-to-Maximum Time (904) | 120-480 msec | Not evaluated |
| Velocity Amplitude (905) | >295 | 250-10000 |
| Compression Width (906) | <562.5 msec | 30-1300 msec |
| Relaxation Time (907) | >300 msec | Not evaluated |
| Release Time (908) | Not evaluated | ≤800 msec |

In an implementation, one or more of the values or ranges shown above in Table 2 may serve as threshold values or ranges for identification of the type of compression waveform. For example, if the measured compression rate on the waveform is less than 77 cpm or greater than 83 cpm, then the measured waveform does not correspond to the belt-based compressions. Conversely, if the measured compression rate is greater than or equal to 77 cpm and less than or equal to 83 cpm, then the measured waveform does correspond to the belt-based compressions. As a further example, if the measured hold time is less than 120 msec, then the measured waveform does not correspond to the belt-based compressions. Conversely, if the measured hold time waveform is greater than or equal to 120 msec, then the measured waveform corresponds to the belt-based compressions. The processor 162 may evaluate the features according to Table 2 to distinguish the belt-based compression waveform from the manual compression waveform and to distinguish the manual compression waveform from signal noise. Some of the listed features may not provide a detectable difference between types of waveforms. Thus the processor 162 is configured to determine a subset of features (e.g., one or more of the listed features) to evaluate in order to identify the compression waveform. In the example above, the release time 908 is not evaluated to distinguish belt-based compressions from manual compressions. Similarly, the velocity minimum-to-maximum time 904 and the relaxation time 907 are not evaluated to distinguish the manual compression waveform from noise. Other subsets of evaluated features are consistent with the disclosure as Table 2 provides an example only of evaluated features.

Referring again to FIG. 9B, in an implementation, the processor 162 may evaluate a waveform shape to detect shape features characteristic of a type of chest compression waveform. As shown in FIG. 9B, the velocity waveform may exhibit a shoulder feature 910. This shoulder feature 910 may be characteristic of the hand-held ACD device waveform and an automated ACD device waveform. For example, the spring and/or the suctions cups in ACD devices may introduce fluctuations in the acceleration signal (e.g., as indicated by feature 916 in FIG. 9B) on top of variations in the acceleration signal due to the chest compressions. In this example, the shoulder feature 910 precede a peak in the velocity waveform. In an implementation, the processor 162 may identify the shoulder feature 910 based on a change in slope of the waveform. The change in slope is shown schematically as a first slope 912*a* that changes to a second slope 912*b* and then changes again to a third slope 912*c*. The second slope 912*b* may be less than the first slope 912*a* and the third slope 912*c*. The processor 162 may quantify the shoulder feature 910, for example, according to the values of the slopes 912*a*, 912*b*, and 912*c*, the differences in these slopes, and/or the width 914 of the shoulder feature 910. In this manner, the processor 162 may distinguish the shoulder region characteristic of the hand-held ACD device from a shoulder in a waveform for a different type of chest compression due to noise in the waveform. Similarly, the processor 162 may distinguish the shoulder region characteristic of the hand-held ACD device from a monotonic change in amplitude associated with another type of chest compression.

In further reference to FIG. 9B, during ACD chest compressions (e.g., mechanical ACD and mechanically assisted manual ACD), the patient's sternum is typically pulled upward beyond the neutral position of the sternum. Thus, the compression phase and decompression phase will both have a portion of motion during which the sternum is pulled upward beyond the neutral position. This portion of motion corresponds to an elevated phase. As shown in FIG. 9B, the ACD displacement waveform includes four phases in reference to the neutral position (NP) 920, e.g., compression elevated (CE) phase 930, compression non-elevated (CN) phase 935, decompression elevated (DE) phase 940, and decompression non-elevated (DN) phase 945. As a result, in order to determine chest compression depth during ACD compressions, a waveform analysis algorithm implemented by the processor 162 includes an identification of the compression neutral point 920. In an implementation, the algorithm may set a pre-compression neutral point as the initial position of the chest prior to an initiation of chest compressions. However, due to chest remodeling that typically occurs during chest compressions, the pre-compression neutral point may change over the course of applied chest compressions. Chest remodeling generally refers to changes in the anterior/posterior diameter of the patient's chest based on a combination of an applied force during the chest compressions and a compliance of the patient's chest. Chest compliance is the mathematical description of the tendency of the chest to change shape as a result of the applied force. Thus, compression depth feedback based on the pre-compression neutral point is likely to be inaccurate.

In order to provide accurate compression depth feedback, the processor 162 may be configured to dynamically determine the compression neutral point 920 to account for changes in the compression neutral point 920 over the course of chest compressions. To this end, the waveform analysis algorithm may need additional information such as compression force information (e.g., as provided by the one or more force sensors 362 in the ACD device), motion information for the elevated and non-elevated phases, and chest compliance information. The chest compliance information may be a mathematical relationship between displacement, force, and chest compliance. The processor 162 may determine accurate compression depth feedback for ACD compressions based on the dynamically determined compression neutral point 920. The compression depth feedback based on the dynamically determined compression neutral point 920 may include the compression non-elevated depth 950 (e.g., the CN depth) and the decompression elevated height 960 (e.g., the DE height).

Figure 10:
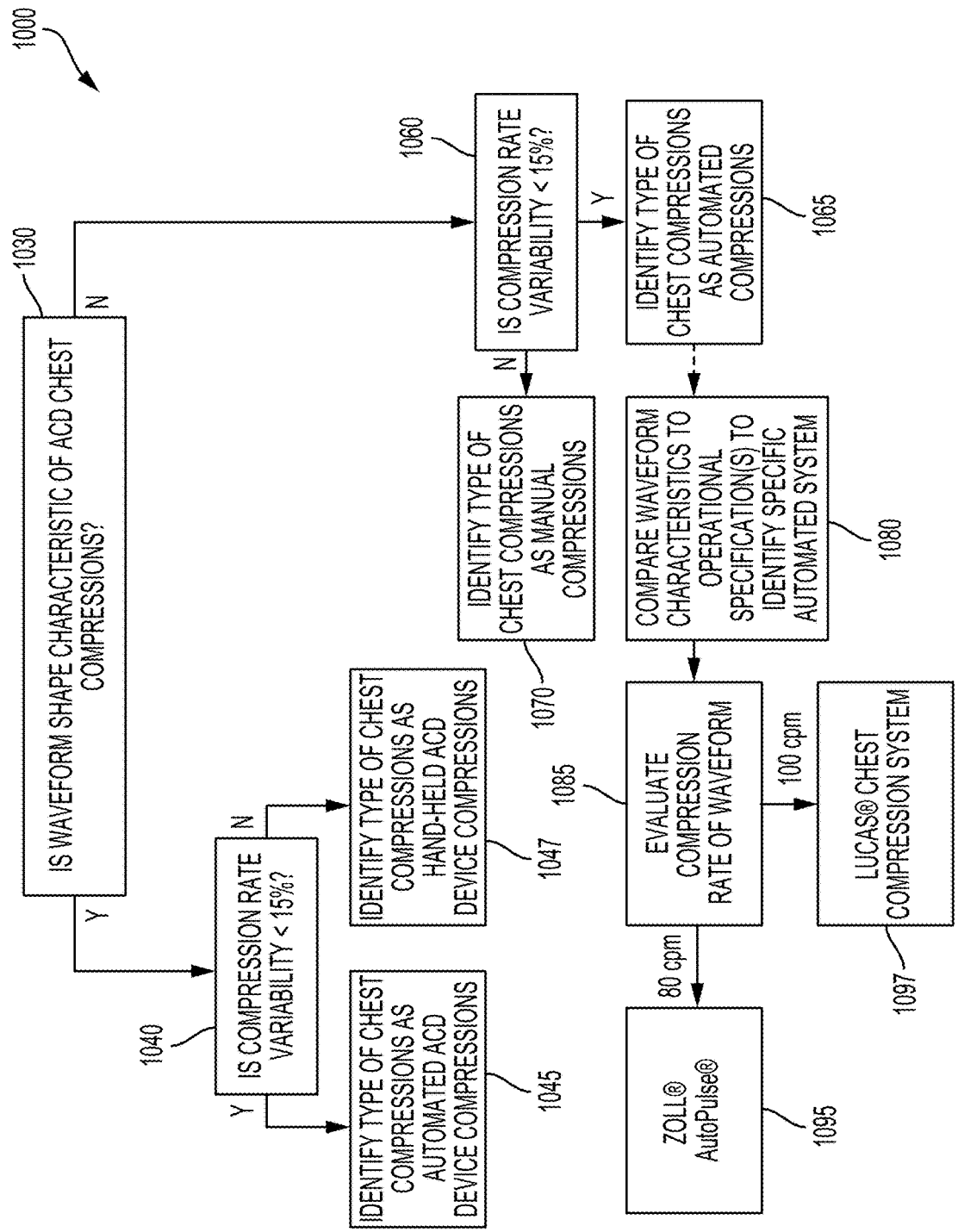
FIG. 10 is a block diagram of an example of a decision tree to detect features characteristic of a type of compression waveform

Referring to FIG. 10, a block diagram of an example of a decision tree to detect features characteristic of a type of compression waveform is shown. In this example, at stage 1030 of the decision tree 1000, the processor 162 evaluates the waveform shape for features characteristic of ACD chest compressions (e.g., automated ACD compressions and hand-held device ACD compressions). As discussed above, the waveform for ACD chest compressions may include the shoulder feature 910. If the processor 162 determines that the waveform includes the shape characteristic of ACD chest compressions (e.g., the shoulder feature 910), then the decision tree branches to the stage 1040, otherwise the decision tree branches to the stage 1060.

At the stages 1040 and 1060, the processor 162 may evaluate a compression rate variability. In an implementation, the processor 162 may measure a variability of one or more of the features 901, 902, 903, 904, 905, 906, 907, and 908 over a multiple compression cycles. The measured variability may be, for example, a range, a standard deviation, or another measure of the variation associated with a feature value over multiple compression cycles. The processor 162 may compare the variation of a feature over a number of compression cycles to a pre-determined threshold criterion. The processor 162 may identify the compression type based on the comparison or may eliminate a candidate compression type based on the criterion. For example, if the variation is below the threshold criterion, the processor 162 may identify a first compression delivery system and if the variation is above the threshold criterion, the processor 162 may identify a second compression system. As another example, if the variation is below the threshold criterion, the processor 162 may identify a first type of compression and if the variation is above the threshold criterion, the processor 162 may rule out the first type of compression without identifying a second type of compression. The processor 162 may utilize an additional criterion to identify the second type of compression. For example, the belt-based system in FIG. 2A may be configured (e.g., according to a chest compression rate specification for the system) to deliver a compression rate of 80 cpm. In practice, the belt-based system may deliver a compression rate is in a range from 77-83 cpm over two or more compression cycles. Thus, in this example, the variability of the compression rate is approximately 4% (e.g., the compression rate is 80 cpm +/−4%). As another example, the piston-based system in FIG. 2B may be configured to deliver a compression rate of 100 cpm. In practice, the piston-based compression device may deliver a compression rate is in a range from 95-105 cpm over two or more compression cycles. Thus, in this example, the variability of the compression rate is approximately 5% (e.g., the compression rate is 100 cpm +/−5%). In contrast, the waveform from manual compressions may exhibit a compression rate that varies by 15%-50%. In general, automated chest compression devices deliver a more consistent compression rate (i.e., lower variability) than manual chest compressions. Therefore, a threshold value for variability (e.g., a threshold variability as determined based on an operation specification for the automated chest compression devices) may serve to distinguish the automated chest compression waveform (e.g., automated ACD or automated non-ACD) from the manual chest compression waveform.

Referring again to FIG. 10, at the stage 1040, the processor 162 may evaluate the compression rate variability to distinguish between the mechanically assisted manual ACD compression waveform and the automated ACD compression waveform. At the stage 1060, the processor 162 may evaluate the compression rate variability to distinguish between the automated compression waveform and the manual compression waveform.

In this example, if the variability is low (e.g., <15%), then, at the stage 1045 the processor 162 may identify the chest compressions as automated ACD device chest compressions. If the variability is high (e.g., ≥15%), then, at the stage 1047, the processor 162 may identify the chest compressions as hand-held ACD device compressions. Similarly, if the variability is low (e.g., <15%), then, at the stage 1065, the processor 162 may identify the chest compressions as automated chest compressions. If the variability is high (e.g., ≥15%), then, at the stage 1070, the processor 162 may identify the chest compressions as manual chest compressions.

Optionally, at the stage 1080, the processor 162 may further identify the compression waveform as corresponding to a particular type of automated compression device based, for example, on an operational specification of the automated system. Thus, at the stage 1085, the processor 162 may compare the characteristics of the compression waveform to operational specifications of one or more automated chest compression systems to identify the automated chest compression system delivering the chest compressions to the patient. For example, the ZOLL® AutoPulse® is configured to deliver chest compressions at 80 cpm whereas the LUCAS® chest compression system is configured to deliver chest compressions at 100 cpm. Thus, at the stage 1095, the processor 162 may identify the compression waveform as a ZOLL® AutoPulse® compression waveform based on the compression rate (e.g., feature 902 as discussed above) of 80 cpm. At the stage 1097, the processor 162 may identify the compression waveform as a LUCAS® chest compression system waveform based on the compression rate (e.g., feature 902 as discussed above) of 100 cpm. The ZOLL® AutoPulse® and LUCAS® chest compression system are examples only of particular types of automated compression devices and are not limiting of the disclosure. Similarly, the values of 80 cpm and 100 cpm are examples only of specific operational specifications and are not limiting of the disclosure.

In addition to the waveform features and shapes discussed above, the processor 162 may evaluate other waveform parameters to identify the type of compression waveform and the type of chest compressions. For example, the processor 162 may evaluate a consistency of waveform shapes by applying an autocorrelation function to the waveform peaks. For example, the waveform peaks for automated chest compressions may produce a high degree of autocorrelation as compared to the waveform peaks for manual chest compressions. As a further example, the processor 162 may compare waveform peak amplitudes with a threshold value to distinguish peaks due to chest compressions from peaks due to noise in the motion sensor signal. In general, peak amplitudes due to chest compressions are higher than those found in a noise signal.

Referring again to FIG. 5, at stage 540, the method 500 includes controlling an output device to selectively provide compression feedback to the rescuer based at least in part on the identified chest compression waveform. In various implementations, selectively providing feedback may include changing displayed values of compression parameters, altering a configuration of a display screen, changing tones or other parameters of audible feedback, adding or deleting parameters to or from a set of feedback parameters, and/or changing colors or other parameters of the display screen. The processor 162 may implement these changes based on the identified type of compressions.

The compression feedback may include an indication of a measured compression parameter. Further, the compression feedback may include an indication of a comparison of the measured compression parameter to a target and/or an indication of a suggested change to the measured compression to reach the target. For example, the processor 162 may control the output device 168 so that one or more compression parameter values are not displayed or otherwise provided to the rescuer. As a further example, the processor 162 may control the output device 168 to stop delivery of voice prompts, text prompts (i.e., written messages on the display screen), metronome prompts, and/or visual display color change prompts. Additionally, or alternatively, the processor 162 may control the output device 168 to not provide graphic indications of the measured parameters and/or graphic indications of a comparison between the measured parameter and the target. For example, a geometric shape such as a rectangle, circle, or diamond that fills to indicate a comparison of the measured parameter to the target may remain filled or unfilled but not display any changes or may not be displayed. As another example, a pulsating graphic may remain still or may not be displayed. In this manner, the processor 162 may withhold compression feedback. (i.e., the processor 162 does not display or otherwise provide indications of the feedback to the rescuer). However, the processor 162 may or may not determine the feedback when the processor 162 does not provide the feedback. Thus withholding feedback does not imply that the feedback exists in and/or is known to the memory 164 and/or the processor 162.

In an implementation, the processor 162 may control the output device 168 to provide values of the measured parameters along with an indication of the identified type of compression waveform. The processor 162 may control the output device 168 to change one or more output characteristics of the provided parameters based on the identified type of compression waveform. The output characteristics may include, for example, but not limited to, the color, the font, the size, the brightness, the location, the audible frequency, and/or the audible volume. For example, the output device 168 may display the compression rate and depth in a dimmer manner for automated chest compressions than for manual chest compressions in order to de-emphasize these numbers. Additionally, the output device 168 may display, for example, "automated compression device-do not adjust" or other indication of the identified type of compression waveform in proximity to the dimmed compression rate and depth.

In general, selectively providing the rescuer feedback includes modifying the compression information that the output device 168 presents as feedback. For example, the feedback may indicate to the rescuer that the compression depth and/or the compression rate conforms to a desired compression depth and/or compression rate. In other words, the feedback indicates to the rescuer that the compression depth is a "good" compression depth if the compression depth is greater than or equal to a target depth. Similarly, the feedback indicates to the rescuer that the compression rate is a "good" compression rate if the compression rate is greater than or equal to a target rate. The processor 162 may use the target depth and the target rate as thresholds for determining if the measured compression depth and/or the measured compression rate are satisfactory or in need of modification. The targets and thresholds may be single numbers or may be a range of values. The provided feedback then indicates to the rescuer if the chest compression parameters are satisfactory or in need of modification. In determining the feedback, the processor 162 may modify the threshold or threshold range based on the type of chest compression detected. For example, if the processor 162 detects mechanical chest compressions, the compression rate threshold range corresponding to a satisfactory compression rate may be 73-82 compressions per minute (cpm). However, for mechanically assisted manual ACD compressions, the compression rate threshold range may be 70-80 cpm and for manual compressions the compression rate threshold range may be 100-120 cpm. The narrower range for the mechanical compressions (e.g., a range of 9 cpm) is due to more controlled tolerance of a mechanical system as compared to a manual system (e.g. a range of 20 cpm). The range for the mechanically assisted manual ACD compressions may account for improved efficiency of compressions with mechanical assistance as opposed to manual compressions. As another example, if the processor 162 detects mechanical compressions without ACD, the compression depth threshold range may be 1.25-2.5 inches (e.g., 3-7 cm) whereas the compression depth threshold range for ACD may include separate ranges for the downstroke and the upstroke. Compression depth and compression rate are examples only of parameters evaluated for feedback and not limiting of the disclosure. The processor 162 may evaluate other measured compression parameters and determine appropriate feedback.

Figure 11:
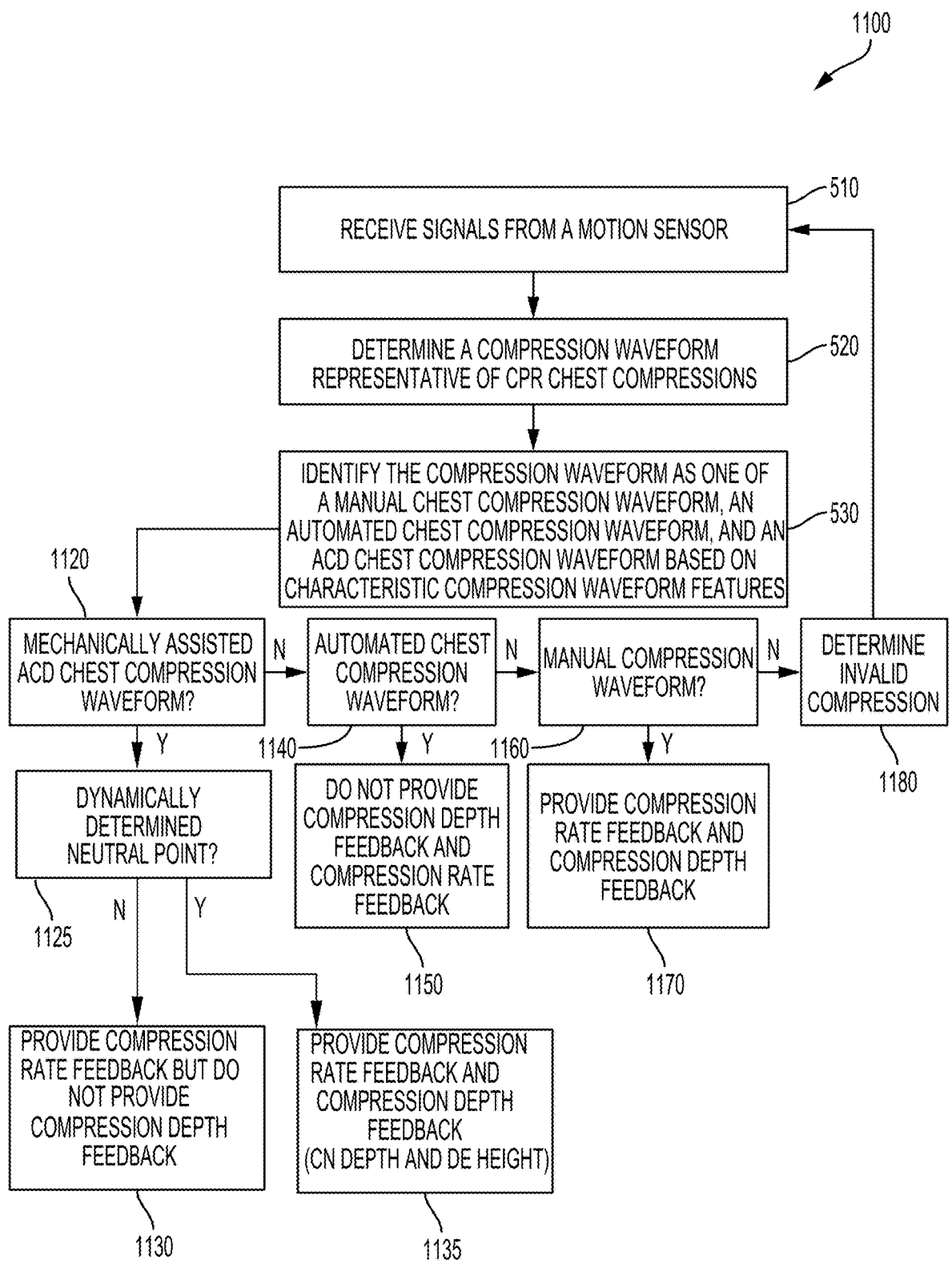
FIG. 11 is a block diagram of a method of selectively providing rescuer feedback.

Referring to FIG. 11, a method of selectively providing rescuer feedback is shown. The method 1100 is, however, an example only and not limiting. The method 1100 can be altered, e.g., by having stages added, removed, rearranged, combined, and/or performed concurrently. The stages 510, 520, and 530 of the method 1100 are described above in reference to FIG. 5.

At stages 1120, the processor 162 may identify the compression waveform as the mechanically assisted manual ACD chest compression waveform. The selectively provided feedback for the mechanically assisted manual ACD chest compression waveform depends on the use of the dynamically determined compression neutral point 920, as determined at stage 1125. If the waveform analysis algorithm is based on the pre-compression neutral point, then, at stage 1130 the processor 162 may control the output device 168 such that the output device 168 does not provide compression depth feedback but does provide compression rate feedback. However, if the waveform analysis algorithm is based on the dynamically determined compression neutral point 920, then, at stage 1135, the processor 162 may provide compression rate and compression depth feedback. The compression depth feedback may include chest displacement feedback for the compression non-elevated (CN) phase (e.g., the CN depth 950 as illustrated in FIG. 9B) and for the decompression elevated (DE) phase (e.g., the DE height 960 as illustrated in FIG. 9B).

At stage 1140, the processor 162 may identify the compression waveform as the automated chest compression waveform. In this case, at the stage 1150, the processor 162 may control the output device 168 such that the output device 168 may withhold compression depth feedback and withhold compression rate feedback. As compression depth and compression rate are predetermined parameters for the automated belt-based device, the rescuer cannot adjust these parameters at least during operation of the automated device. Also, the predetermined parameters for automated compressions may differ from ACLS guidelines for manual compressions (e.g., the compression rate for the belt-based compression device may be 80 cpm while the ACLS recommended rate may be 100 cpm). Feedback may confuse and/or distract the rescuer to the detriment of the resuscitative care provided by the rescuer. Further, the feedback may cause the rescuer to attempt to change compression parameters of the automated compression device to the detriment of patient care.

At stage 1160, the processor may identify the compression waveform as the manual compression waveform. In this case, at the stage 1170, the processor 162 may control the output device 168 such that the output device 168 provides compression depth feedback and compression rate feedback. Both compression rate and compression depth are controllable and adjustable by the rescuer for manual compressions.

At stage 1180, the processor 162 may determine that the compression identification is invalid. This determination may indicate that the compression type was incorrectly identified at the stage 530. In other words, the threshold analysis and detection function may erroneously identify waveform features as corresponding to an individual compression. For example, the amplitudes of the waveforms may vary due to noise contributions to the motion sensor signals. The noise contributions may be due to vibrations due to road conditions for a patient in a vehicle, patient motion, gurney motion, vehicle suspension vibrations, etc. In this case, the method 1100 returns to the stage 510 to receive and analyze additional signals received from the motion sensor 118.

The specific feedback provided and/or withheld as discussed above with regard to the stages 1130, 1150, and 1170 is by way of example only. The systems described herein may automatically determine the type of chest compressions and selectively provide the feedback in a manner other than the examples provided.

At one or more of the stages of the methods 500 and/or 1100, the processor 162 may store CPR parameter information in the memory 164. The processor 162 may store the CPR parameter information during manual compressions, automated compressions and/or mechanically assisted manual compressions. The CPR parameter information may include one or more of the signals received from the motion sensor 118 and the processed waveforms (e.g., as shown, for example, in FIGS. 6A-8E) and/or the compression parameters determined from the waveforms. The processor 162 may store the information as an event log with time stamps associated with various portions of the information. The stored information may include an indication of the identified type of CPR compressions.

Figure 12:
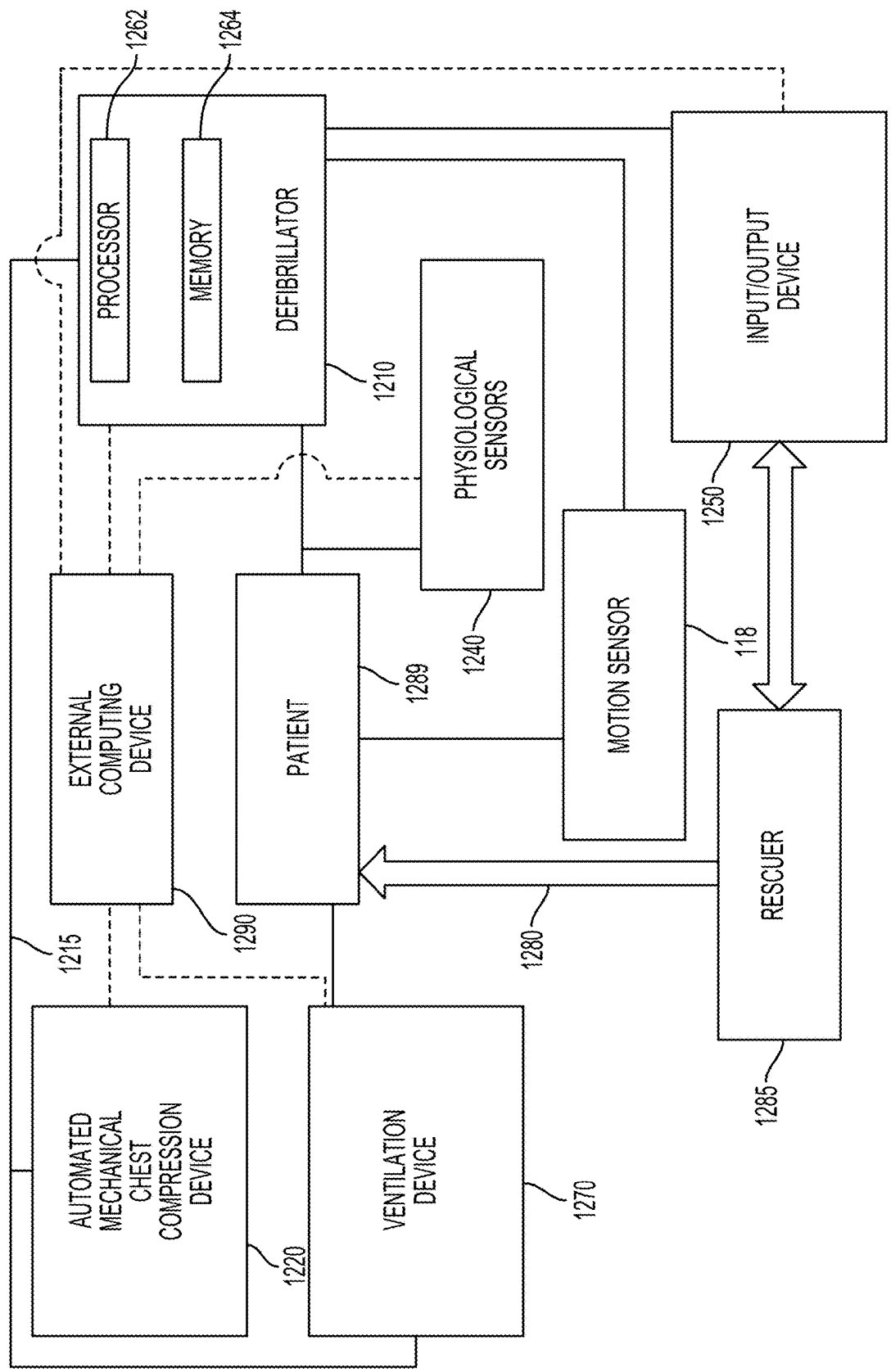
FIG. 12 is a block diagram of an example of a system configured to synchronize delivery of a defibrillation shock with chest compressions.

Referring to FIG. 12, an example of a system configured to synchronize delivery of a defibrillation shock with chest compressions is shown. In an implementation, the computing device 160 is a defibrillator 1210. The defibrillator 1210 includes a processor 1262 and a memory 1264. The defibrillator processor 1262 and the memory 1264 are configured with the capabilities, structure, and functionality as described herein with regard to the processor 162 and the memory 164, respectively. For example, the defibrillator processor 1262 may use the chest compression parameters, for example, as measured by the motion sensor 118 disposed in the electrode assembly, to identify the type of chest compressions. The defibrillator processor 1262 may tailor resuscitation feedback provided by the defibrillator 1210 to the identified type of chest compressions as described herein with regard to the methods 500 and 1000. Additionally, the defibrillator processor 1262 is configured to synchronize delivery of chest compressions with delivery of the defibrillation shock by the defibrillator 1210. The efficacy of the defibrillation shock may depend on the timing of the shock with respect to the chest compressions, for example. The defibrillator processor 1262 may analyze the motion sensor signal to detect various phases and timing points in the compression cycle. The phases include, for example, the decompression phase and the compression phase. The timing points may include, for example, a start of the decompression phase and a maximum positive slope (e.g., dV/dt) in the velocity waveform. Based on this analysis, the defibrillator processor 1262 may select a timing point in the compression cycle at which to deliver the defibrillation shock. The defibrillator processor 1262 may further determine a time interval, or delay, relative to the timing point at which to deliver the defibrillation shock. For example, the defibrillator processor 1262 may determine the time interval from a detection of the start of the decompression phase to initiation of delivery of the defibrillation shock. This time interval may be a number of milliseconds (e.g., 1-400 msec). In an implementation, the defibrillator processor 1262 may further synchronize the delivery of the defibrillation shock with a combination of the chest compression cycle and measured ECG activity.

In order to synchronize defibrillation with manual chest compressions and/or mechanically assisted manual chest compressions, the defibrillator 1210 may provide synchronization instructions to the rescuer 1285 via an input/output device 1250. The input/output device 1250 may be substantially as described above with regard to the output device 168.

For manual chest compressions (e.g., manual compressions 1280 delivered by the rescuer 1285 to the patient 1289), the therapeutic benefits of defibrillation shock during the compressions may improve when combined with a shorter duration of the upstroke phase. For example, the duration of the upstroke phase may be shorter during a synchronized defibrillation/compression treatment than in compressions delivered without defibrillation synchronization. An increased upstroke velocity (e.g., the release velocity) may reduce the duration of the upstroke phase. Rescuer feedback that includes prompting (e.g., visual prompting and/or audible prompting) directed at the upstroke velocity may help the rescuer to achieve the desired shorter duration of the upstroke phase.

A consideration with the synchronization of defibrillation to manual compressions is that the defibrillation shock generates approximately 2000 volts. Touching the patient directly during a defibrillation shock will not harm the rescuer, but it may generate a significant amount of discomfort. In an implementation, the rescuer may place an electrically insulating protection layer that extends over the surface of the patient so that manual compressions may continue safely and unabated during the defibrillation shock delivery. Alternatively, for identified manual chest compressions, the defibrillator 1210 may provide instructions to the rescuer to stop chest compressions prior to delivery of the shock.

In order to synchronize defibrillation with the automated chest compressions, the defibrillator 1210 may communicate, via a wired and/or wireless connection 1215, with an automated chest compression device 1220 (e.g., the belt-based system 200 or the piston-based system 260). For example, the defibrillator 1210 may communicate via an analog signal, a serial Universal Serial Bus (USB) interface, or via a low-latency wireless protocol such as the IEEE 802.15.4 protocol standard (e.g., ZigBee®). The defibrillator processor 1262 may control the defibrillator 1210 to deliver the defibrillation shock at a particular point during the CPR chest compression cycle to synchronize the defibrillation shock with the chest compressions. The synchronization may increase the efficacy of the defibrillation shock. As an example, the defibrillator 1210 may deliver the shock at or near the deepest point of compression.

In an implementation, the defibrillator processor 1262 is configured to control the input/output device 1250 to provide an instruction to the rescuer to use the defibrillator to deliver the defibrillation shock to the victim. For example, the input/output device 1250 may provide one or more of a displayed, an audible, and/or a vibration based command for the rescuer to push a shock button on the defibrillator. The defibrillator processor 1262 may control the input/output device 1250 to provide defibrillation parameter feedback to the rescuer 1285. The input/output device 1250 may be a component of the defibrillator 1210 and/or may be a separate device communicatively coupled to the defibrillator 1210. For example, the defibrillation parameter feedback may include one or more of shock energy information, ECG information, defibrillator equipment status information, defibrillator data analysis status information, shock timing information, pacer information, and chest impedance information.

The defibrillator processor 1262 may further synchronize the delivery of defibrillation shock with compressions based at least in part on signals from the physiological sensors 1240. In an implementation, the defibrillator processor 1262 may receive input from one or more physiological sensors 1240 configured to generate signals indicative of physiological parameter information for the victim. The defibrillator processor 1262 may determine the physiological parameter information from the sensor signals. The physiological sensors 1240 may include one or more of a blood pressure sensor, a blood flow sensor, a ventilation sensor, an oxygenation sensor, and an end tidal carbon dioxide sensor. The physiological sensors 1240 may further include the defibrillation electrodes which may function as chest impedance sensors and/or ECG sensors. These sensors may be individual or combined sensors. The defibrillator may provide physiological information to the rescuer via the input/output device 1250. Alternatively, or additionally, the defibrillator may store the physiological information and/or transmit the physiological information to another device. The physiological information may include blood pressure information, ECG information, blood flow information, chest impedance information, ventilation information, oxygenation information, and end tidal carbon dioxide information. In an implementation, the processor 162 may determine the chest compression feedback based at least in part on the physiological parameter information. For example, chest impedance information and/or blood flow information may indicate a sufficient or insufficient chest release.

In an implementation, the defibrillator processor 1262 may analyze the ECG of the patient. Based on this analysis, the defibrillator processor 1262 may determine the time for delivery of the defibrillation shock. The efficacy of the defibrillation shock may depend on the timing of the shock with respect to a varying state of the heart during ventricular fibrillation (VF), for example. During VF, variations in the state of excitability of the heart cells results in a cyclic period of increased susceptibility to defibrillation. The susceptible period occurs when the number of excitable cells is low, i.e., a higher state of depolarization. The ECG waveform may be indicative of these susceptible periods and provide a basis for shock synchronization with the ECG. The defibrillator processor 1262 may filter the ECG signal from the patient in order to reduce compression signal artifacts in the ECG signal to improve the accuracy of the ECG signal. In an implementation, the defibrillator processor 1262 is configured to send a signal to a controller of the automated compression device (e.g., the controller 225 of the automated belt-based device or the control unit 286 of the automated piston-based device) to stop compressions prior to and/or during the ECG analysis. Stopping the compressions during the ECG analysis may reduce or eliminate signal artifacts from the chest compressions in the ECG signal.

In an implementation, the defibrillator processor 1262 may synchronize pacing with compressions in order to augment the compressions with the electrically-induced contractions of the myocardium. During a resuscitation, the heart is in a state of profound ischemia resulting in a flaccidity and loss of tone as lactate builds up in the myocardium and the tissue pH drops. As a result of the loss of tone, the heart becomes a less-effective pump structure for generating blood flow during manual chest compressions. Drugs such as epinephrine act to improve tone, but because they are delivered venously, their action may take 2-3 minutes during cardiac arrest, when the only blood flow is that induced by the chest compressions. Pacing may improve the tone of the myocardium without the therapeutic delay experienced with drugs such as epinephrine. This improvement in myocardial tone may substantially improve the hemodynamic effectiveness of the compressions.

In an implementation, the defibrillator processor 1262 may synchronize compressions and shock with delivery of ventilations by a ventilation device 1270. At the time of defibrillation shock, it is desirable that there not be a ventilation in progress. Preferable sequencing is for ventilation expiratory cycle to complete in the decompression phase of the compression cycle immediately preceding the compression cycle during which the synchronized shock takes place. The defibrillator 1210 may communicate with the ventilation device 1270 to synchronize the delivery of ventilations with the compressions and defibrillation shock. Alternatively, or additionally, the defibrillator 1210 may provide ventilation prompts for a rescuer controlling the ventilation device 1270.

In an implementation, an external computing device 1290 may control the defibrillator 1210. For example, a processor of the external computing device 1290 may provide all or a portion of the functions and capabilities of the processor 162 in lieu of and/or in combination with the defibrillator processor 1262. In an implementation, the external computing device 1290 may work in coordination with the defibrillator 1210. For example, the external computing device 1290 may receive and/or transmit data to and/or from the defibrillator and/or coordinate communications between the defibrillator 1210 and other external devices. The other external devices may include compression devices, ventilation devices, physiological sensors, and/or input/output devices. The data may include patient medical data, resuscitative care events, data, and/or feedback, CPR parameters and/or feedback, timing information, location information, defibrillation parameters, physiological information, etc. The defibrillator 1210 may communicate with the external computing device 1290 via a short range wireless connection (e.g., Bluetooth®, Wi-Fi, etc.), a cellular network and/or a computer network (e.g., an Internet Protocol network).

Although shown as separate units in FIG. 12, in an implementation, the automated chest compression device 1220 may include some or all of the defibrillator electronics. A power supply for the chest compression device may provide power for compressions as well as defibrillation. This configuration may provide a benefit of reducing the amount of equipment that the rescuer needs to carry to the scene of a cardiac arrest.

Figure 13A:
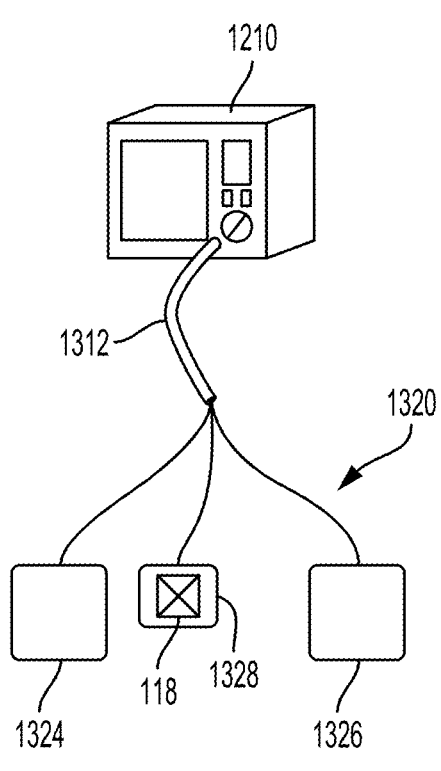
FIGS. 13A and 13B are schematic diagrams of examples of defibrillation assemblies.
Figure 13B:
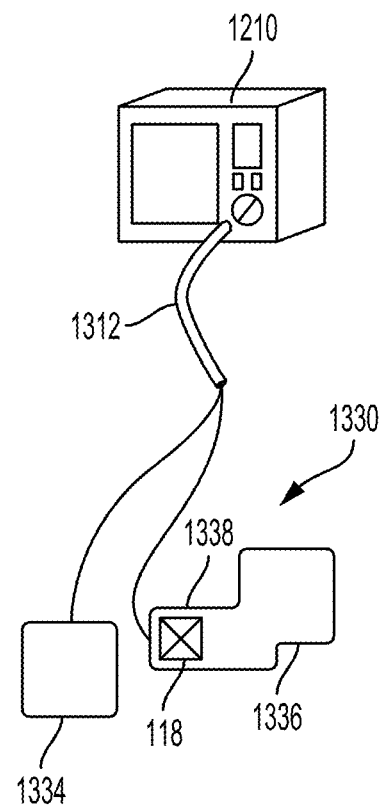

Referring to FIGS. 13A and 13B, schematic diagrams of examples of defibrillation assemblies are shown. During the course of resuscitation, it may be desirable for the rescuer to apply an electrode assembly to the patient's chest. The rescuer may utilize the electrode assembly in conjunction and coordination with various types of chest compressions. The various types of chest compressions include, for example but not limited to, the types of compressions listed in Table 1. The electrode assembly may remain in place on the chest of the patient when chest compressions are delivered.

Referring to FIG. 13A, the electrode assembly 1320 includes a first electrode 1324, a second electrode 1326, and a chest compression assembly 1328. The rescuer may place the first electrode 1324 and the second electrode 1326 in an anterior-anterior position or an anterior-posterior position such that a therapeutic current may travel through the patient's heart. As an example, in operation, the rescuer may place the first electrode 1324 above the patient's right breast and may place the second electrode 1326 below the patient's left breast. The electrode assembly 1320 further includes a chest compression assembly 1328. The chest compression assembly 1328 includes the motion sensor 118, as described above. The assembly 1328 may include the motion sensor 118 disposed within a plastic housing (not shown). The motion sensor 118 moves with the assembly as the rescuer performs chest compressions and decompressions on the patient so that the motion of the motion sensor 118 substantially matches the motion of the patient's chest. The chest compression assembly 1328 is shown in FIG. 13A as having an "X" printed on its top surface to indicate to the rescuer where to place his or her hands when delivering chest compressions and decompressions to a patient. The chest compression assembly 1328 is configured to transmit signals from the motion sensor 118 to the defibrillator (e.g., defibrillator 1210, defibrillator 1400, defibrillator 1500) through the wired leads 1312. Although shown as a wired connection in FIG. 13A, in an implementation, chest compression assembly 1328 may transmit signals wirelessly from the motion sensor 118 to the defibrillator (e.g., defibrillator 1210, defibrillator 1400, defibrillator 1500) and/or to another computing device (not shown), for example, a mobile device, a portable computer, a medical device, a desktop computer, etc.

Referring to FIG. 13B, the electrode assembly 1330 includes a first electrode 1334, a second electrode 1336, and a chest compression assembly 1338. The first electrode 1334 may be a single electrode, as similarly described above with regard to the first electrode 1324. The second electrode 1336 may include the chest compression assembly 1338. The chest compression assembly 1338 includes the motion sensor 118 and is substantially similar to the chest compression assembly 1328 as described above. Aside from differing in geometry and in the inclusion of the chest compression assembly 1338, the second electrode 1336 is substantially similar to the second electrode 1326 as described above. Similarly to the electrodes 1324 and 1326, the rescuer may place the first electrode 1334 and the second electrode 1336 in an anterior-anterior position or an anterior-posterior position such that a therapeutic current may travel through the patient's heart.

As discussed above, the motion sensor 118 is disposed in (i.e., is a component of) the electrode assemblies 1320 and 1330. However, in an implementation, defibrillation electrode assemblies may not include the motion sensor 118 (i.e., the motion sensor may be a component of an assembly physically separate from the electrode assembly). For example, as described above (with regard to FIGS. 1, 2A, 2B, 3C, and 3D) the compression puck 110, the compression belt 210, the compression pad 289, the compression target pad 330, and/or the hand-held ACD device 310 may include the motion sensor 118. The rescuer may use these described compression components inclusive of the motion sensor 118 in conjunction and/or coordination with defibrillation electrode assemblies. The defibrillator may include a first connection to the motion sensor 118 and a second connection to the defibrillation electrodes. The first connection to the motion sensor 118 may be a wired and/or wireless connection. In a further implementation, the defibrillator and/or other computing device may receive signals from the motion sensor 118 disposed in the electrode assembly and receive signal from the motion sensor 118 disposed in another component or assembly.

The electrode assembly 1320 and/or the electrode assembly 1330 are configured to connect to the computing device 160 and/or the defibrillator (e.g., defibrillator 1210, defibrillator 1400, defibrillator 1500) by way of a wired leads 1312 connected to the defibrillator by way of a plug (not shown). For example, the defibrillator may include a female or male connection, and the plug may include a corresponding connection in a manner that is well known in the art. The wired leads 1312 may transmit power to and/or from the defibrillator. For example, current to provide a therapeutic shock to a patient may flow from the defibrillator to the electrode assembly 1320 and/or 1330. As another example, electrical signals for corresponding to electrocardiogram (ECG) information, motion sensor information, and/or measurements of chest impedance information may flow from the electrode assembly 1320 and/or 1330 to the defibrillator.

The electrodes 1324, 1326, 1334, and 1336 may include a flexible foam layer that includes a gel layer on the bottom of the electrode configured to conduct the defibrillation shock to the patient. Before they are deployed, the various electrodes and assemblies, as described for example herein, may be stored in a sealed packet to keep the gel layer moist, and the wires may be coiled to reduce needed space. A rescuer may open the packet, plug the wires into the defibrillator, and if necessary, read instructions on the back sides of the electrodes and/or the packet regarding the proper manner to apply the electrodes (e.g., with graphics that show the peeling off of covers over the electrode gels and also show images of the proper placement of the electrodes on a line-drawn patient). In some instances, the wires may already be plugged into the defibrillator. For example, the wires may extend through a sealed hole out of the sealed packet. For the electrode 1336, the gel layer may exclude (i.e., may not extend under) the attached chest compression assembly 1338. The chest compression assembly 1328 and/or 1338 may include an adhesive layer on a surface configured to removably attach to the patient. This may prevent the motion sensor from moving relative to the patient's chest and/or separating from the patient's chest during chest compressions and decompressions. Such an adhesive layer may improve the accuracy of the chest motion determined from the motion sensor signals.

In an implementation, one or more of the electrodes 1324, 1326, 1334, and 1336 may include indicia (e.g., textual and/or graphical instructions) on a surface of the electrode(s) that may indicate how to deploy the electrode(s) and/or how to place the electrode(s) on the patient. Alternatively, or additionally, the defibrillator may display instructions and/or provide verbal instructions. The instructions may indicate procedures for using the electrode(s) and/or the defibrillator. The electrodes 1324, 1326, 1334, and/or 1336 may be configured to sense an ECG reading from the patient and/or to measure the chest impedance of the patient. These electrodes may transmit signals indicative of these sensed parameters to the defibrillator.

In various implementations, one or more of the chest compression assemblies 1328 and/or 1338 may include a chest compression assembly display (not shown). The chest compression assembly display is disposed on the chest compression assembly and may provide feedback that is directed to the rescuer who is performing the chest compressions and decompressions. The feedback may be similar to feedback provided by the display 168 and may include chest compression information, rescuer positioning information, and/or other resuscitative care feedback. One or more of the chest compression assemblies 1328 and/or 1338 may further be configured to provide audio feedback and/or haptic feedback. The defibrillator may determine the feedback and control the chest compression assembly display. In an implementation, the chest compression assembly may include a processor and a memory and may determine the feedback and control the chest compression assembly display. In an implementation, the chest compression assembly may determine, store, receive, and/or transmit information to/from the defibrillator and/or another computing device. The information may include patient medical data, resuscitative care data, CPR parameters, timing information, location information, etc.

In an implementation, the electrode assembly 1320 and/or 1330 may include one or more LEDs. The LEDs may provide feedback for the rescuer. For example, the LEDs may blink, remain illuminated and/or change color to indicate a chest compression rate, depth, and/or release velocity, a rescuer position switch, a defibrillation timing, and/or other resuscitative care feedback.

The electrode assembly 1320 and electrode assembly 1330 are examples only and not limiting of the disclosure. Other electrode assembly configurations are compatible with the systems and methods described herein.

Figure 14:
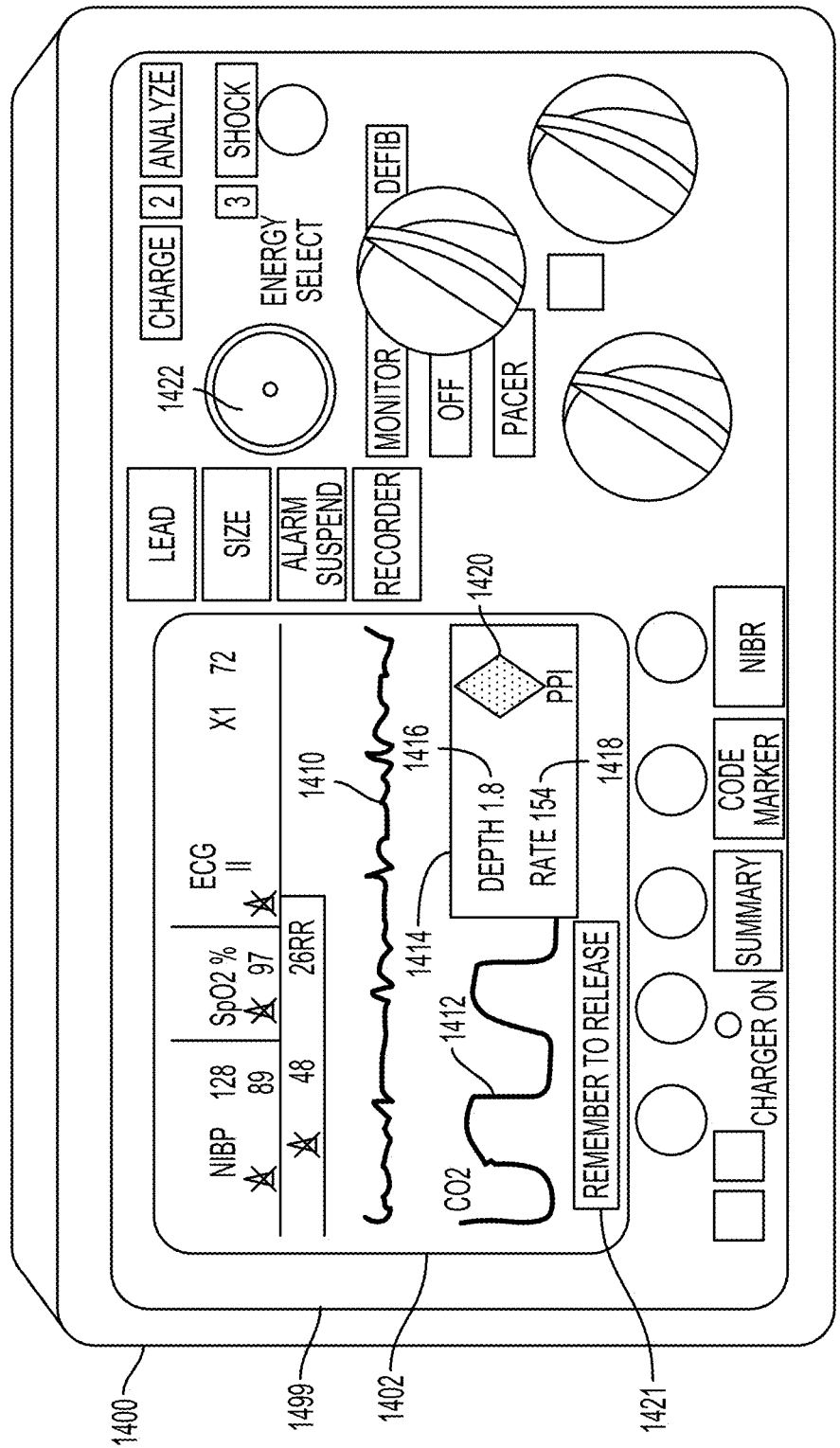
FIG. 14 is a schematic diagram of an example of a defibrillator configured to provide real-time rescuer feedback.

Referring to FIG. 14, a schematic diagram of an example of a defibrillator 1400 configured to provide real-time rescuer feedback is shown. The features shown in FIG. 14 are examples only, and not limiting of the disclosure, of information that can be displayed to the rescuer. In an implementation, the computing device 160 may be the defibrillator 1400. The defibrillator 1400 may include the components of the computing device 160 as described above (e.g., the processor 162, the memory 164, the communication interface 166, and the output device 168) and may be coupled to the motion sensor 118. The defibrillator 1400 may include a dashboard 1499. In an implementation, the defibrillator 1210 may include the dashboard 1499. The dashboard 1499 is an example of a defibrillator user interface and may include one or more input devices, output devices, and combination input/output devices.

The dashboard 1499 may provide information about patient status and CPR administration quality during the use of the defibrillator device. The dashboard 1499 may include a display area 1402. As shown in FIG. 14, during the administration of chest compressions and decompressions, the dashboard 1499 may display information about the chest compressions and decompressions, for example, the information displayed in box 1414. As illustrative examples, a filtered ECG waveform 1410 and a CO2 waveform 1412 are shown. Alternatively, or additionally, the dashboard 1499 may display an $SpO_2$ waveform.

During chest compressions and decompressions, the defibrillator processor (e.g., 162, 1262) may generate the filtered ECG waveform by gathering ECG data points and motion sensor readings and filtering motion-induced (e.g., CPR-induced) noise out of the ECG waveform. The filtered ECG waveform may reduce interruptions in CPR as compared to a non-filtered ECG waveform. The non-filtered ECG waveform may include artifacts from chest compressions and decompressions that may make it difficult for the rescuer to discern the presence of an organized heart rhythm unless compressions and decompressions are halted. Filtering out these artifacts may allow rescuers to accurately view the heart rhythm without stopping chest compressions and decompressions.

The defibrillator processor (e.g., 162, 1262) may control the dashboard 1499 to provide CPR parameters in box 1414 automatically in response to detecting chest compressions. For example, the CPR parameters may include the chest compression rate 1418 (e.g., number of compression cycles per minute) and the chest compression depth 1416 (e.g., depth of compressions in inches or millimeters). Displaying the measured rate and depth data, in addition to, or instead of, an indication of whether the values are within or outside of an acceptable range may enhance the value of the feedback for the rescuer. For example, if an acceptable range for chest compression depth is 25 to 60 mm, providing the rescuer with an indication that his/her compressions and decompressions are only 15 mm may allow the rescuer to determine how to correctly modify his/her administration of the chest compressions and decompressions (e.g., he or she can know how much to increase effort, and not merely that effort should be increased some unknown amount).

The defibrillator processor (e.g., 162, 1262) may also control the dashboard 1499 to provide a perfusion performance indicator (PPI) 1420. The PPI 1420 may be a geometric shape (e.g., a diamond, square, a rectangle, a circle, a triangle, or other polygon) with an amount of fill that is in the shape differing over time to provide feedback about one or more of the rate and depth of the chest compressions. When the rescuer performs manual CPR adequately (e.g., according to ACLS guidelines and/or at a rate of about 100 compressions and decompressions per minute (CPM) with the depth of each compression greater than 40 mm) the fill will cover the entire area of the geometric shape (e.g., the entire indicator may be filled). As the rate and/or depth decreases below acceptable limits, the fraction of the filled area of the geometric shape decreases. The PPI 1420 may provide a visual indication of the quality of the CPR. Further, the PPI 1420 may provide a target for the rescuer to keep the PPI 1420 completely filled.

As an example of a defibrillator dashboard layout, the filtered ECG waveform 1410 may be a full-length waveform that may fill the entire span of the display device, while the second waveform (e.g., the CO2 waveform 1412) may be a partial-length waveform that fills only a portion of the display. A portion of the display beside the second waveform provides the CPR information in box 1414. For example, the display may split the horizontal area for the second waveform in half, displaying waveform 1412 on left, and CPR information on the right in box 1414. However, the layout, configuration, and included information for the dashboard 1499 as described above are examples only and other layouts, configurations, and included information are within the scope of the disclosure.

As another feedback example, a reminder 1421 regarding "release" in performing chest compression is shown in FIG. 14. Specifically, a fatigued rescuer may lean forward on the chest of a patient and not sufficiently release pressure on the sternum of the patient at the top of each decompression stroke. This may reduce the perfusion and circulation accomplished by the chest compressions. The defibrillator processor (e.g., 162, 1262) may control the dashboard 1499 to provide the reminder 1421 when the defibrillator processor (e.g., 162, 1262) determines that the rescuer is not sufficiently releasing. For example, signals from the motion sensor 118 may exhibit an "end" to the compression cycle that is flat and thus indicates that the rescuer is maintaining pressure on the sternum to an unnecessary degree.

The defibrillator processor (e.g., 162, 1262) may control the dashboard 1499 to change the data provided to the rescuer based on the actions of the rescuer and/or based on the identified type of chest compressions. For example, the defibrillator processor (e.g., 162, 1262) may selectively provide or withhold displayed feedback (e.g., the defibrillator processor may withhold and/or modify the displayed feedback) as described above based on the identified type of chest compressions. A display area designated for withheld feedback (e.g., the box 1414 which is designated for depth and rate feedback) may be dark or otherwise non-illuminated and/or absent of displayed information.

The dashboard 1499 may provide spoken and/or tonal audible feedback and/or haptic feedback as an alternative or in addition to the examples of visual indications described above. As an example, the defibrillator 1210 may emit a sound through speaker 1422 in the form of a metronome to guide the rescuer in the proper rate of applying CPR compressions. The defibrillator may not provide the audible and/or haptic feedback based on the identified type of CPR compressions. For example, the defibrillator may silence the metronome and/or other audible feedback.

Figure 15A:
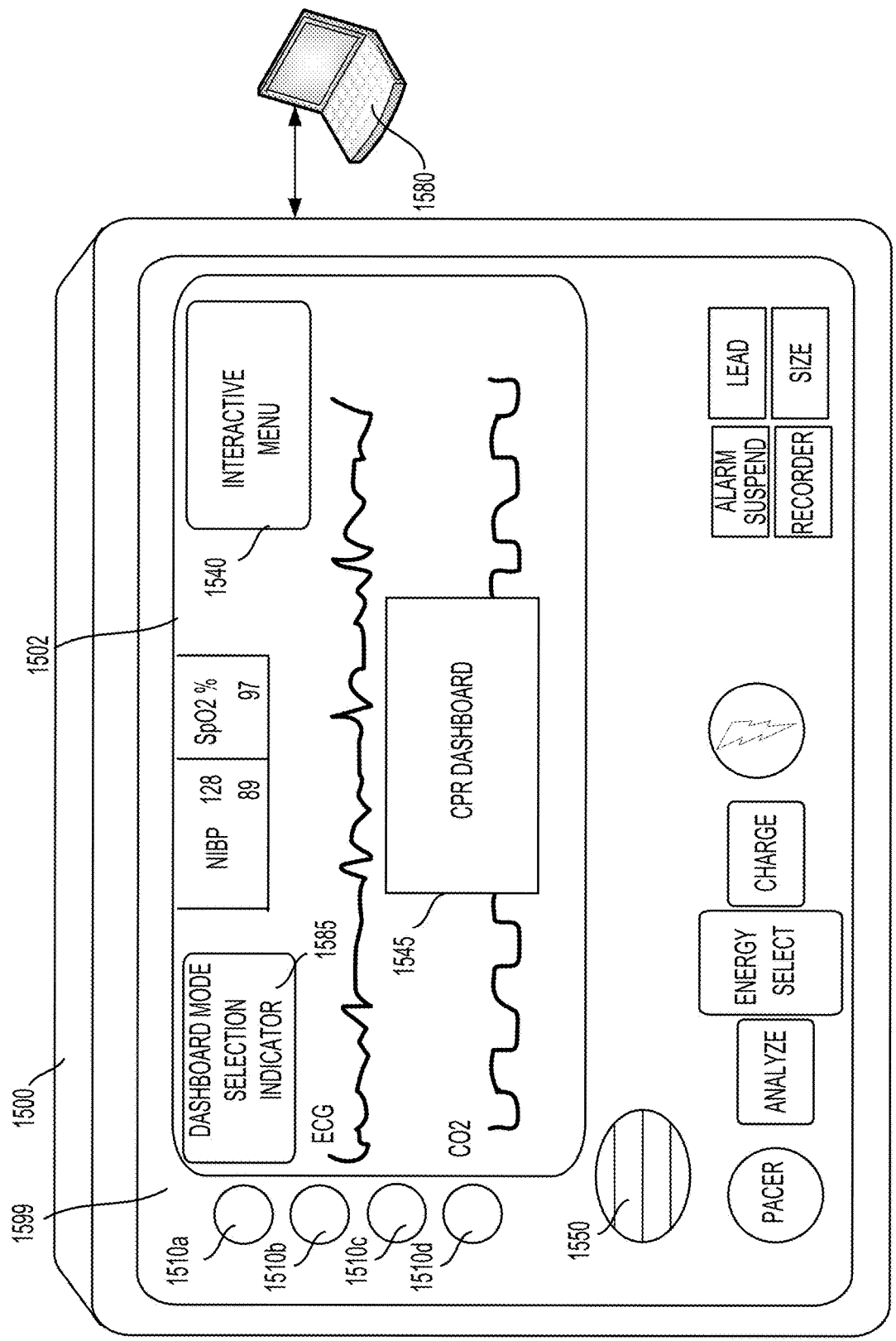
FIGS. 15A-15E are schematic diagrams of an example of a defibrillator that provides a dynamically configurable dashboard feedback based on a type of chest compressions.

Referring to FIG. 15A, an example of a defibrillator 1500 is shown that provides dynamically configurable dashboard feedback based on a type of chest compressions. In an implementation, the computing device 160 may be the defibrillator 1500. The defibrillator 1500 may include one or more of the above-described components of the defibrillator 1210 and/or 1400. As such, the defibrillator 1500 may be configured to interface with the components 118, 1220, 1240, 1250, 1270, 1289, 1290 in a manner substantially similar to the defibrillator 1210. Thus, the defibrillator 1500 may be configured to synchronize the delivery of chest compressions with the delivery of a defibrillation shock by the defibrillator 1500. Although shown as a defibrillator in FIG. 15 and referred to as a defibrillator herein, embodiments of the present disclosure may be implemented in a patient monitor that is not necessarily configured to deliver a defibrillation shock and/or other electrical stimulation treatments. Such a patient monitor may still provide monitoring and/or feedback for ECG and other physiological parameters and/or monitoring and/or feedback for resuscitative care parameters such as chest compression parameters.

The defibrillator 1500 may include a user interface 1599 (e.g., a dashboard). The user interface 1599 may be substantially as described above regarding the dashboard 1499. The user interface 1599 may include a display area 1502. In an implementation, in response to receiving signals from the motion sensor 118, the processor of the defibrillator 1500 (e.g., the processor 162) may determine that the signals from the motion sensor 118 are indicative of chest compressions. In response to this determination, the processor may automatically (e.g., without requiring and/or receiving user input indicative of the provision of chest compressions) control the user interface 1599 to display a CPR dashboard 1545. Additionally, a processor of the defibrillator 1500 (e.g., the processor 162) may execute control software and/or firmware (e.g., processor executable instructions stored on a non-transitory medium, such as the memory 164) configured to selectively control chest compression feedback provided by the CPR dashboard 1545 included in the user interface 1599. In the example of FIG. 15A, the CPR dashboard 1545 overlays physiological feedback. However, this arrangement of the CPR dashboard 1545 is an example only and not limiting of the disclosure. In an implementation, the user interface 1599 may display the CPR dashboard 1545 in another location on the user interface 1599 such that other information provided by the user interface 1599 remains unobstructed. One or more of the CPR dashboard 1545 and the display area 1502 may be a touchscreen and/or a pressure-sensitive touchscreen.

Selectively controlling the chest compression feedback may include operating the CPR dashboard 1545 in one or more feedback modes. Each of the feedback modes may correspond to a respective type of chest compressions. For example, a first feedback mode may correspond to a first type of chest compressions and a second feedback mode may correspond to a second type of chest compressions. In a particular feedback mode, the CPR dashboard 1545 may selectively control the feedback, for example, by suppressing at least a portion of the chest compression feedback based on the type of chest compressions. For example, in the first feedback mode, the CPR dashboard 1545 may provide and/or suppress certain types of feedback appropriate for the first type of chest compressions. In the second feedback mode, the CPR dashboard 1545 may provide and/or suppress certain types of feedback appropriate for the second type of chest compressions. The type of chest compressions corresponding to each mode may correspond to one of the types of chest compressions shown in Table 1.

The selective changes to the user interface provided by the CPR dashboard 1545 are pre-determined based on the type of chest compressions, as known by the defibrillator 1500. For example, the user of the defibrillator 1500 may actuate the dashboard mode selection switch 1510a and/or otherwise provide input that identifies the type of chest compressions. In response to this user input, the feedback provided by the CPR dashboard 1545 may change. However, in some instances, the CPR dashboard 1545 may not provide the user with the ability to select/deselect individual types of feedback. In other words, the control software of the defibrillator may be pre-configured to determine the individual feedback types that are provided or suppressed based on the identified type of chest compressions, where these individual feedback types may not be individually selected/deselected by the user. Thus, once the user provides input regarding the type of compressions, the control software may determine which feedback to provide or suppress without further user input.

Table 3 below provides an example summary of the rescuer feedback that may be selectively provided (e.g., provided or suppressed) based on the type of chest compressions. It should be understood that the information in this table is provided by way of example only and not limiting of the present disclosure. In various implementations, the control software may be configured to provide feedback indicated in Table 3 as suppressed and/or to suppress feedback indicated in Table 3 as provided. In various implementations, the CPR dashboard 1545 may provide and/or suppress any or a portion of the dashboard information. That is, depending on the particular mode that indicates the type of chest compressions being delivered to the patient, any suitable combination of feedback, such as those feedback listed in Table 3, or even no feedback at all, may be provided. Various modes may also be pre-configured by a user so that the types of feedback presented and suppressed are appropriately tailored to the mode.

TABLE 3

| TYPE OF CHEST COMPRESSIONS | DELIVERY SYSTEM EXAMPLE | PROVIDED FEEDBACK | SUPPRESSED FEEDBACK |
|---|---|---|---|
| manual chest compressions | hands of rescuer | CPR timer CPR idle timer compression depth compression rate chest release circulation metronome | |

TABLE 3-continued

| TYPE OF CHEST COMPRESSIONS | DELIVERY SYSTEM EXAMPLE | PROVIDED FEEDBACK | SUPPRESSED FEEDBACK |
|---|---|---|---|
| mechanically assisted manual ACD chest compressions | hand-held ACD device (NO NEUTRAL POINT DETECTION) | CPR timer CPR idle timer | compression depth compression rate chest release circulation metronome |
| mechanically assisted manual ACD chest compressions | hand-held ACD device (NEUTRAL POINT DETECTION) | CPR timer CPR idle timer compression depth compression rate chest release circulation metronome | |
| automated chest compressions | belt-based system | Optional: CPR timer CPR idle timer | compression depth compression rate chest release circulation metronome |
| automated chest compressions | piston-based system | Optional: CPR timer CPR idle timer | compression depth compression rate chest release circulation metronome |
| automated ACD chest compressions | piston-based ACD system (NO NEUTRAL POINT DETECTION) | Optional: CPR timer CPR idle timer | compression depth compression rate chest release circulation metronome |
| automated ACD chest compressions | piston-based ACD system (NEUTRAL POINT DETECTION) | Optional: CPR timer CPR idle timer | compression depth compression rate chest release circulation metronome |

As an example, the mechanically assisted manual ACD chest compressions might involve use (e.g., manual operation), by the rescuer, of a hand-held ACD device. As an example, the hand-held ACD device may be a ResQPUMP® ACD-CPR device from ZOLL® Medical Corp. and the user may provide the mechanically assisted manual ACD chest compressions with the ResQPUMP® ACD-CPR device. As discussed above in reference to Table 1, manual chest compressions refer to classic two-hand CPR (e.g., compressions according to Advanced Cardiac Life Support (ACLS) guidelines) where the compression parameters (e.g., compression rate, periodicity, compression depth, release velocity, and other compression waveform characteristics) are controlled by and subject to variability due to physical actions of the CPR provider (e.g., the rescuer). Mechanically assisted manual ACD chest compressions (e.g., delivered manually using an ACD device) refer to compressions delivered using devices that, though mechanical in nature, depend on the physical activity of the CPR provider to control the compression parameters. Automated chest compressions refer to chest compressions delivered by devices that are controlled by computerized control systems, electro-mechanical systems, or the like, such that the compression parameters are predetermined by the programming or design of the device, and are not subject to variability due to the physical actions of a CPR provider (other than providing input to the control system or adjusting set points for an electromechanical system, as allowed by the system). For example, the automated chest compressions may be belt-based compressions, piston-based compressions, or piston-based ACD compressions.

In an implementation, if the mechanically assisted manual ACD compression apparatus includes the motion sensor 118 and/or another accelerometer configured to detect chest motion, then the user interface 1599 may display (i.e., may provide and not suppress) the compression rate feedback (e.g., as described with regard to block 1130 of FIG. 11). Alternatively, if the mechanically assisted manual ACD compression apparatus does not include the motion sensor 118 and/or another accelerometer configured to detect the chest motion, then the user interface 1599 may suppress the compression rate feedback as indicated in Table 3.

The control software of the defibrillator 1500 may include configuration settings that determine whether or not the user interface 1599 provides the feedback indicated as "optional" in Table 3 . Further, the control software may include a pre-determined indication of neutral point detection capabilities and automatically adjust the provided feedback accordingly.

Figure 15B:
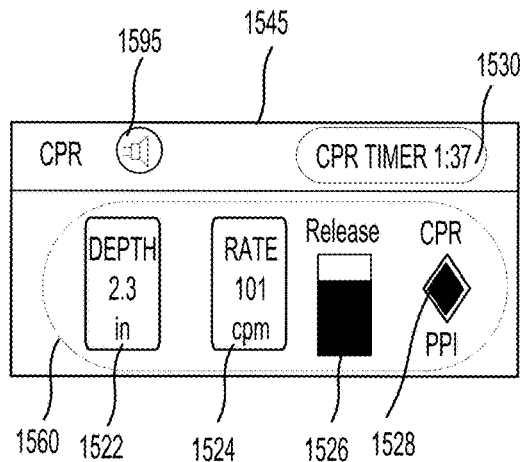
Figure 15C:
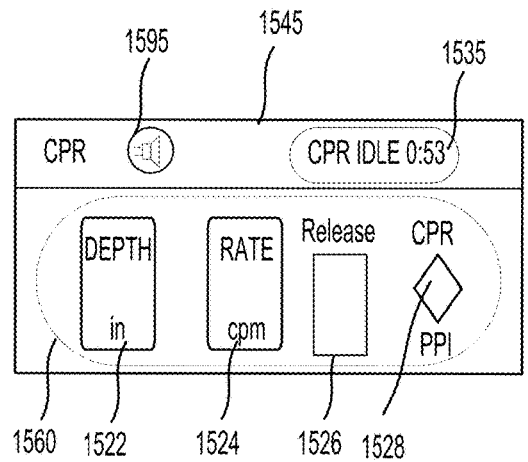

Referring to FIGS. 15B-15E, examples of the first feedback mode and the second feedback mode are shown. In the examples of FIGS. 15B and 15C, the first feedback mode corresponds to the manual chest compressions. FIG. 15B shows an example of this first feedback mode during active delivery of the manual chest compressions and FIG. 15C shows an example of this first feedback mode during an idle period during the manual chest compressions. During the active delivery of a series of chest compressions, the CPR timer 1530 may indicates a time remaining in the ongoing series of chest compressions, where the CPR time duration for the series of chest compressions may be pre-configured. The CPR idle timer 1535 may be a chest compression pause timer that indicates a duration of a pause in the active delivery of the chest compressions. These timers are discussed in more detail below.

The feedback may include two or more portions of feedback, e.g., first chest compression feedback and second chest compression feedback. As an example, the first chest compression feedback may include the CPR timer 1530 and the CPR idle timer 1535. The second chest compression feedback may include compression performance indicators 1560 such as, for example, the feedback indicators 1522, 1524, 1526, and/or 1528. The second chest compression feedback may further include a metronome (e.g., as represented by an audio indicator 1595 and/or 1596). As shown in these figures, in accordance with Table 3, the provided feedback for the manual chest compressions may include the first chest compression feedback (e.g., one or more of the CPR timer 1530 and the CPR idle timer 1535) and the second chest compression feedback (e.g., one or more of the compression depth (e.g., via compression depth indicator 1522), the compression rate (e.g., via the compression rate indicator 1524), chest release (e.g., via the chest release indicator 1526), the circulation (e.g., via the perfusion performance index (PPI) indicator 1528), and the metronome). For example, the feedback indicators for the first chest compression feedback and the second chest compression feedback may all be displayed.

Figure 15D:
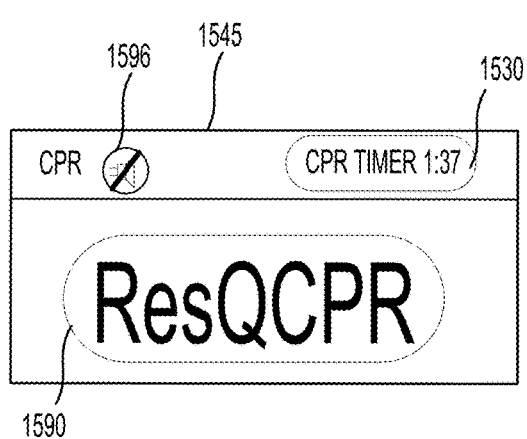
Figure 15E:
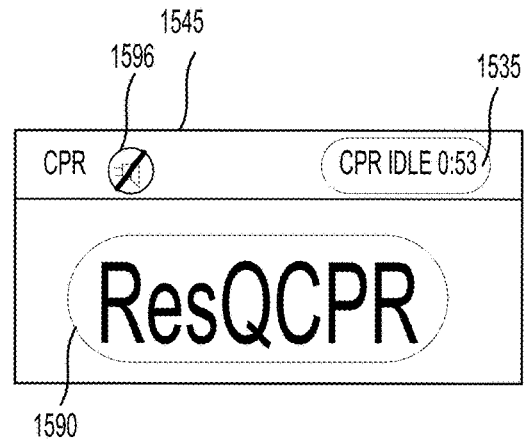

In the examples of FIGS. 15D and 15E, the second feedback mode corresponds to the mechanically assisted manual ACD chest compressions. In these examples, the first chest compression feedback (e.g., the CPR timer 1530 and the CPR idle timer 1535) is provided and the second chest compression feedback (e.g., the one or more of compression depth, compression rate, chest release, circulation feedback, and metronome) is suppressed. For example, the compression performance parameters 1560 (e.g., the feedback indicators 1522, 1524, 1526, and 1528) may not be displayed in the CPR dashboard 1545.

In the examples of FIGS. 15B-15E, one or the other of the CPR timer 1530 and the CPR idle timer 1535 are shown. However, these are examples only. In an implementation, both timers may appear. Further, the time may be represented by one or more of a numeric, text, and/or graphic indication.

In an implementation, the CPR dashboard 1545 replaces the compression performance parameters 1560 with a dashboard mode indicator 1590 when the second chest compression feedback is suppressed. In these examples, the dashboard mode indicator 1590 displays "ResQCPR" to indicate that the user interface 1599 is in the second feedback mode and that the second feedback mode corresponds to the mechanically assisted manual ACD chest compressions. Although shown in FIGS. 15D and 15E as replacing all of the feedback indicators 1522, 1524, 1526, and 1528, this is an example only and not limiting of the disclosure. In an implementation, the dashboard mode indicator 1590 may be located away from the feedback indicators 1522, 1524, 1526, and 1528 such that the dashboard mode indicator 1590 does not replace any of these indicators or replaces a portion of these indicators. If one or more indicators are visible to the user but the information provided by the one or more indicators is suppressed, then the indicator may display a numeric, textual, and/or graphical indication that the feedback corresponding to the indicator is suppressed.

In an implementation, the CPR dashboard 1545 may include the audio indicator 1595 and/or 1596. The audio indicator 1595 may represent an audible metronome and/or other enabled audio, as shown for example in FIGS. 15B and 15C. The audio indicator 1596 may represent an inaudible metronome (e.g., a suppressed metronome) and/or other disabled audio, as shown for example, in FIGS. 15D and 15E. In an implementation, the control software of the defibrillator 1500 and/or defibrillator hardware may provide a user and/or automatically controlled option to enable and disable audio.

The dashboard mode indicator 1590 may indicate that the user interface 1599 is in the second feedback mode and/or may indicate the type of chest compressions corresponding to the second feedback mode. For example, the dashboard mode indicator 1590 may display the name of the type of chest compressions, a graphical representation of the type of chest compressions, and/or another indication that the user interface 1599 is in the second feedback mode and/or another indication of the type of chest compressions being delivered. In an implementation, the defibrillator 1500 may provide an audible indication of the identified type of chest compressions, for example, via a speaker 1550. In an implementation, the user interface 1599 may not display the dashboard mode indicator 1590.

In the first feedback mode, which may be a default feedback mode, the dashboard mode indicator 1590 may display a type of chest compressions associated with the default mode. In an implementation, the dashboard mode indicator 1590 may display an automatically identified type of chest compressions.

Figure 16A:
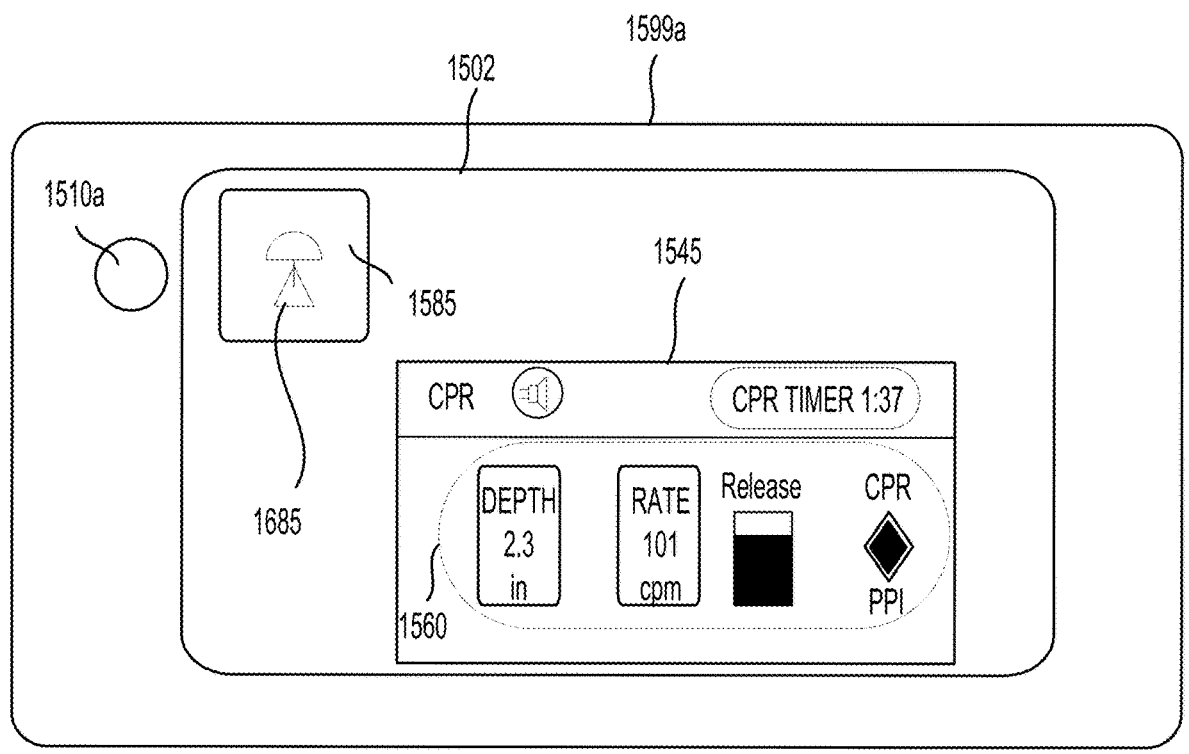
FIGS. 16A and 16B show schematic diagrams of a portion of the dashboard shown in FIG. 15A.
Figure 16B:
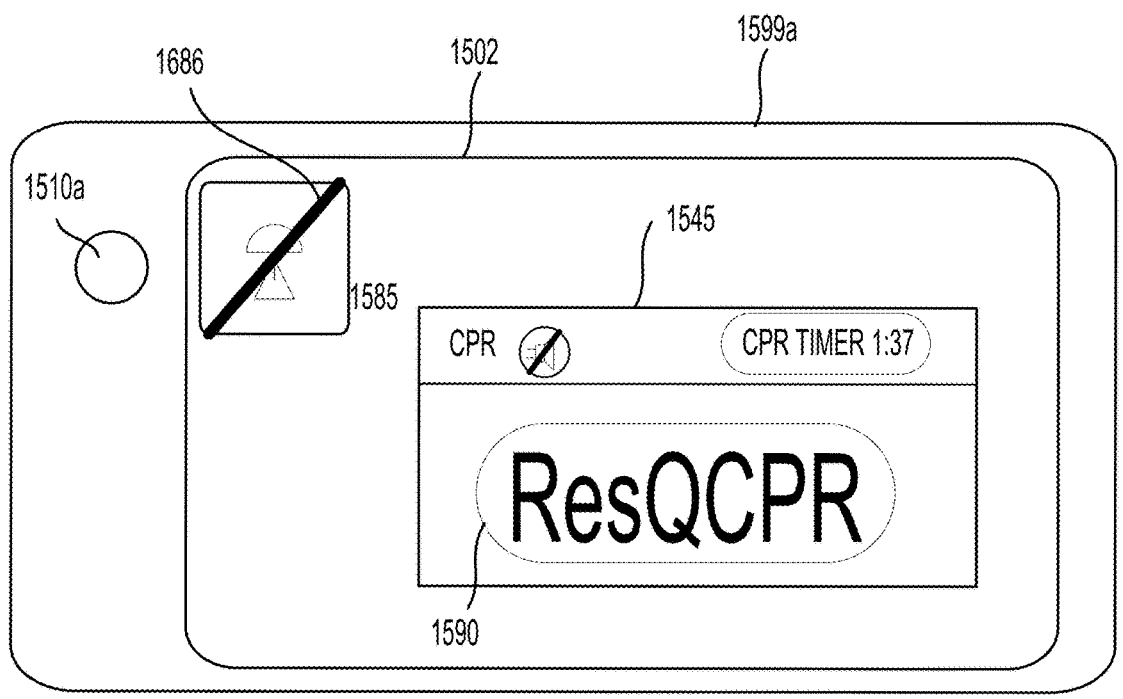

Referring to FIGS. 16A and 16B with further reference to FIG. 15A, in an implementation, the user interface 1599 may include a dashboard mode selection indicator 1585. For simplicity, FIGS. 16A and 16B show schematic diagrams of a portion 1599a of the user interface 1599. The portion 1599a includes the display area 1502, the CPR dashboard 1545, the dashboard mode selection indicator 1585, and the dashboard mode selection switch 1510a. In various implementations, the dashboard mode selection indicator 1585 may include text and/or text and graphic(s) to indicate the type of chest compressions that are being applied. In this example, the dashboard mode selection indicator 1585 includes a graphic 1685 indicative of a type of chest compressions (e.g., the hand-held ACD device used to administer the mechanically assisted manual ACD chest compressions).

The dashboard mode selection indicator 1585 may further correspond to a dashboard mode selection switch 1510a. The indicator 1585 may indicate, to the user, that activation of the switch 1510a will transition the user interface 1599 from the first feedback mode to the second feedback mode. The graphic on the dashboard mode selection indicator 1585 may represent the second feedback mode. In this example, the first feedback mode corresponds to the manual chest compressions and the second feedback mode corresponds to the mechanically assisted manual ACD chest compressions. Therefore, the dashboard mode selection switch 1510a is configured to transition the user interface 1599 from the manual compression feedback mode to the mechanically assisted manual ACD compression feedback mode (e.g., the ResQPUMP® mode).

Referring to FIG. 16B, in response to actuation of the dashboard mode selection switch 1510a, the dashboard mode selection indicator 1585 may change its appearance to indicate this actuation. For example, the dashboard mode selection indicator 1585 may display the line 1686 in response to actuation of the mode selection switch 1510a. This appearance of the dashboard mode selection indicator 1585 is an example only and not limiting of the disclosure. In an implementation, the indicator 1585 may include the line 1686 prior to activation of the switch 1510a (e.g., to indicate that the mode has not been selected) and may exclude the line 1686 in response to the activation of the switch 1510*a* (e.g., to indicate that the mode has been selected).

Although one dashboard mode selection switch 1510*a* is discussed above, in an implementation, the user interface 1599 may include one or more dashboard mode selection switches 1510*a*, 1510*b*, 1510*c*, and 1510*d*. The dashboard mode selection switches may include soft-keys, touch screen icons, mechanical switches (e.g., a button, toggle, dial, etc.), voice activated switches, pointer device controlled switches (e.g., a screen option activated by a click of a mouse and/or other pointing device), and/or combinations thereof. The switches may be configured for quick access by the user of the defibrillator 1500. In an implementation, multiple switches may correspond to respective types of chest compressions (e.g., switch 1510*a* may correspond to mechanically assisted manual ACD chest compressions, switch 1510*b* may correspond to automated chest compressions by a belt-based system, etc.). In an implementation, the dashboard mode selection switch may be a selectable option in a user menu.

In the examples of 15D and 15E, the dashboard mode indicator 1590 replaces the feedback indicators 1522, 1524, 1526, and 1528. This configuration is an example only and not limiting of the disclosure. In an implementation, the dashboard mode indicator 1590 be located on the user interface 1599 such that it does not replace the feedback indicators 1522, 1524, 1526, and 1528 or such that it replaces a portion of the feedback indicators 1522, 1524, 1526, and/or 1528. While one dashboard mode indicator 1590 is shown, this is an example only and the user interface 1599 may include multiple dashboard mode indicators at various locations.

In general, if the compression depth, compression rate, chest release, and/or circulation feedback are provided by the CPR dashboard 1545, then the respective feedback indicator (e.g., 1522, 1524, 1526, and/or 1528) may illuminate and/or otherwise be visible to the user of the defibrillator 1500. Conversely, if the compression depth, compression rate, chest release, and/or circulation feedback are suppressed by the user interface 1599, then at least a portion of the respective feedback indicator (e.g., 1522, 1524, 1526, and/or 1528) may not illuminate and/or otherwise not be visible to the user of the defibrillator 1500. For example, the numbers associated with the chest compression depth and/or the chest compression rate may not appear on the user interface 1599 when suppressed. As another example, the areas inside the feedback indicators 1526 and 1528 may remain fully filled or fully empty and may not change from compression to compression. As a further example, the display area corresponding of one or more of the feedback indicators 1522, 1524, 1526, and 1528 may appear blank (i.e., no displayed text and/or graphic). If the metronome is provided, then the beat is audible via the speaker 1550. If the metronome is suppressed, then the beat may be stopped (e.g., may be discontinued by the processor 162, 1262) and/or may not be audible via the speaker 1550. In some implementations, the defibrillator 1500 may be configured to provide one or more of the parameters shown in Table 3 as voice prompts (e.g., via the speaker 1550). If feedback for a particular parameter is "provided" then the voice prompts may provide this information in addition to the display on the CPR dashboard 1545 of the user interface 1599. If feedback for a particular parameter is "suppressed" then the voice prompts may be stopped (e.g., may be discontinued by the processor 162, 1262) and/or may not be audible.

In an implementation, the defibrillator 1500 may monitor and record chest compression parameter data indicated as "suppressed" in Table 3, however, the processor (e.g., 162, 1262) may record (e.g., store in memory 164, 1264) all or a portion of the suppressed data.. Thus "suppressed" may only refer to the defibrillator 1500 not providing this data at the user interface 1599 (e.g., the data is not displayed and/or otherwise provided to the user via the user interface 1599). In an implementation, the defibrillator 1500 may send this data to a computing device (e.g., 430*a*, 430*b*, 1580). In an implementation, the computing device may be a central server that may provide this data to one or more remote computing devices via a computer network and/or communications network connection. The computing device may receive and process this data for review and analysis (e.g., post-case and/or real-time).

In an implementation, the data collected, stored, and or transmitted by the defibrillator 1500 (e.g., motion sensor data, feedback data, physiological data, patient data, caregiver data, physician data, etc.) may include flags or labels that indicate the feedback mode of the user interface 1599 during collection of the data and/or flags or labels that indicate the type of chest compressions. For example, the data may include one or more labels corresponding to the types of chest compressions in Table 1 and/or the equipment used to deliver the compressions. The equipment may be referred to as a category (e.g., mechanically assisted manual ACD chest compressions), as an equipment trade name (e.g., ResQPUMP®) and/or as a feedback mode label (e.g., ResQCPR®). The data may also include flags indicating the start and/or stop of compressions corresponding to a particular mode of delivery. For example, a set of CPR data may be identified as "manual" and another set may be identified as "mechanically assisted manual ACD." These flags may enable the review and analysis procedures to sort, filter, analyze, and/or otherwise process data according to the feedback mode and/or the type of chest compressions.

In an implementation, the first feedback mode may be a default feedback mode and the second feedback mode may be a selected feedback mode. Control software for the defibrillator 1500 may include a feedback mode configuration setting. The manufacturer, distributor, and/or user of the defibrillator 1500 may set the feedback mode configuration setting to a default setting. The default setting may correspond to a pre-determined default type of chest compressions. The default feedback mode may be adjustable prior to initiation of a patient case but may not be adjustable during the course of a patient case. In the default feedback mode, the control software may control the user interface 1599 to provide and/or suppress feedback corresponding to the default type of chest compressions.

In the selected feedback mode, the feedback mode configuration setting may be a selected setting that corresponds to a selected type of chest compressions. The selected type of chest compressions is a type of chest compressions other than (i.e., different from) the default type of chest compressions. For example, in the selected feedback mode, the dashboard mode indicator 1590 may indicate the defibrillator 1500 is in "ResQCPR® mode" with text and/or graphical symbols or representations corresponding to use of the ResQPUMP®. In the "ResQCPR® mode," the user interface 1599 may provide a CPR timer and a CPR idle timer and may suppress feedback for compression depth, compression rate, chest release, and circulation, and a metronome. It can be appreciated that other combinations of feedback may be displayed in the "ResQCPR® mode," or other mode that indicates the type of chest compressions being delivered to the patient.

As another example, the default type of chest compressions may be manual chest compressions and the selected type of chest compressions may be one of mechanically assisted manual ACD chest compressions, automated chest compressions, and automated ACD chest compressions. As a further example, the default setting may correspond to the automated chest compressions and the specialized setting may correspond to the mechanically assisted manual ACD chest compressions. In general, the default setting may correspond to any one of the types of chest compressions listed in Table 1. The selected setting may correspond to any other one of the types of chest compressions listed in Table 1 that is different from the type of chest compressions that correspond to the default setting. In an implementation, the CPR dashboard 1545 may support one or more selected types of chest compressions. For example, in addition to the second feedback mode, the control software may be configured to control the CPR dashboard 1545 according to a third feedback mode, a fourth feedback mode, etc.

The user interface 1599 may be configured to operate in the default feedback mode at power on and/or at a start of a patient case are opened and/or attached to a patient and/or when a resuscitation protocol sequence is started. The user interface 1599 may operate in the default feedback mode in the absence of user input indicative of a type of chest compressions that does not correspond to the default feedback mode. For example, if the default feedback mode corresponds to manual compressions, then user input to the user interface 1599 (e.g., actuation of the switch 1510a or other manner of user input selection) indicative of the type of compressions being a type other than manual compressions may trigger the user interface 1599 to transition to the selected feedback mode (e.g., the non-default feedback mode).

Actuation of one or more of the dashboard mode selection switches 1510a-1510d may change the feedback mode configuration setting from the default setting to the selected setting. Further, various sequences of switch actuations may implement various sequences of feedback mode configuration settings. As a first example, a first actuation of the dashboard mode selection switch 1510a may change the configuration setting from the default setting to the selected setting. A second actuation of the same dashboard mode selection switch may change the configuration setting from the selected setting back to the default setting. As a second example, a first switch (e.g., 1510a) may change the configuration setting from the default setting to the selected setting and a second switch (e.g., 1510b) may change the configuration setting from the selected setting to the default setting. As a third example, a first switch (e.g., 1510a) may change the configuration setting from the default setting to a first selected setting (e.g., from manual compressions to mechanically assisted manual ACD compressions) and a second switch (e.g., 1510b) may change the configuration setting from the default setting to a second selected setting (e.g., from manual compressions to automated belt-based compressions). These examples are not limiting of the disclosure as other combinations and sequences for the one or more switches are possible and within the scope of the disclosure.

In an implementation, the control software may include a mode selection configuration setting that enables or disables the dashboard mode selection switch. For example, the user may change the mode selection configuration setting via the interactive menu 1540 and/or via changes to the control software that may be downloaded to and/or otherwise installed on the defibrillator 1500.

As described above with regard to FIGS. 5-10, in an implementation, the defibrillator 1500 may be configured to automatically identify the type of chest compressions based on a chest motion waveform. In such an implementation, the control software may adjust the feedback mode configuration setting to correspond to the automatically identified type of chest compressions. In the default mode and/or in the selected mode, the control software may tailor the feedback provided to the rescuer via the CPR dashboard 1545, based on the automatically identified type of chest compressions. In an implementation, the first feedback mode and the second feedback mode may both correspond to selected feedback modes based on the automatically identified type of chest compressions. In an implementation, the control software may include an automatic identification configuration setting. The automatic identification configuration setting may determine whether the control software automatically identifies the type of chest compressions or bypasses the automatic identification of the type of chest compressions. If the control software bypasses the automatic identification of the type of chest compressions, then the control software may operate the user interface 1599 according to the default feedback mode and the selected feedback mode described above. In an implementation, actuation of the dashboard mode selection switch 1510a may change the automatic identification configuration setting and cause the control software to bypass automatic identification of the type of chest compressions.

In an implementation, the defibrillator 1500 may be configured to communicate with a computing device 1580. The computing device 1580 may be a mobile device, a cellular communications device, a tablet, a laptop, a personal computer, a server, etc. For example, the user may change the configuration setting for the type of chest compressions via input to the computing device 1580.

In an implementation, when a patient case is initiated, the feedback mode configuration setting may initialize at the default setting. If the feedback mode configuration setting changes the selected feedback mode for a first case, then when a second case begins, the configuration setting may automatically revert back to the default setting. The control software may recognize and/or identify initiation of the patient case based on one or more events. For example, when the caregiver activates the defibrillator 1500 for a case, the control software may capture case identification information (e.g., patient information, caregiver information, time stamp, etc.). The caregiver may power on the defibrillator 1500 to activate the defibrillator. The capture of the identification information and/or the power on/off event may indicate the start of the patient case. As another example, the caregiver may arrive at a patient and attach one or more of the motion sensor 118 and the electrode pads (e.g., 1324, 1326, 1334, and 1336) to the patient and begin CPR. In response, the defibrillator 1500 may activate and/or initiate the user interface 1599 and initiate a case.

As shown in FIGS. 15B and 15C, the CPR dashboard 1545 may include one or more of the compression depth indicator 1522, the compression rate indicator 1524, the chest release indicator 1526, and the circulation indicator 1528 (e.g., a perfusion performance indicator (PPI)). The compression depth indicator 1522 may indicate a chest compression depth and may indicate this depth on a compression-by-compression basis (i.e., change the displayed value of the chest compression depth on a compression-by-compression basis). The compression rate indicator 1524 may indicate a rate of chest compressions in compressions per minute. After two or more compressions, the compression rate indicator 1524 may update the displayed rate on a compression-by-compression basis.

The chest release indicator 1526 and/or the circulation indicator 1528 may include graphics for which a colored area changes size within a frame to indicate a quality of chest release and/or circulation. For example, if the caregiver fully releases the chest of the patient at the end of a chest decompression during a compression/decompression cycle of a single chest compression, then the release indicator 1526 may fill completely. In the example of FIG. 15B, the indicator 1526 may be completely filled as black with a full release. When the indicator 1526 is partially filled (e.g., as shown in FIG. 15B), then the caregiver has not fully released the chest of the patient. The fraction of the indicator 1526 that is full may be based on a chest compression parameter indicative of chest release (e.g., release velocity, force, etc.). The indicator 1526 may change appearance on a compression-by-compression basis to indicate a quality of chest release for each compression/decompression cycle.

The circulation indicator 1528 may indicate an estimated and/or calculated hemodynamic response to chest compressions. The indicator 1528 may change appearance on a compression-by-compression basis to indicate blood perfusion caused by each chest compression. For example, a chest compression rate and a chest compression depth that both fall within recommended guidelines for CPR may indicate a satisfactory hemodynamic response (i.e., satisfactory blood perfusion). Therefore, if both the chest compression depth and the chest compression rate are within the recommended guidelines, then the circulation indicator 1528 in the example of FIG. 15B may be completely filled as black, or any other suitable color and/or fill pattern. This may indicate sufficient chest compression induced circulation. When the indicator 1528 is partially filled (e.g., as shown in FIG. 15B), then one or both of the chest compression depth and chest compression rate are not within the recommended guidelines. The indicator 1528 may change appearance on a compression-by-compression basis to indicate the compliance of the chest compression depth and rate with the guidelines on a compression/decompression cycle. As another example, the estimated hemodynamic response may be based on clinical trials indicative of the blood circulation response to chest compressions for particular chest compression parameters and/or particular patient parameters. In an implementation, the defibrillator 1500 may also provide an audible metronome (e.g., via the speaker 1550) that may provide a beat indicative of a desired compression timing.

FIG. 15B is an example of the CPR dashboard during on-going chest compressions as indicated by the CPR timer 1530. In an implementation, the defibrillator 1500 may analyze the signals from the motion sensor 118 to automatically detect and identify an occurrence of and an absence of chest compressions. For example, the defibrillator 1500 may calculate the chest displacement during compressions by filtering and converting the motion sensor signal into a distance measurement (e.g., the defibrillator 1500 may convert an acceleration signal measurement (cm/s$^2$ or in/s$^2$) into velocity (cm/s or in/s) and then into distance (cm or in)). The defibrillator 1500 may determine the depth of compression from a peek-to-peek amplitude of a displacement waveform determined from the motion sensor signal.

FIG. 15C is an example of the CPR dashboard 1545 during an idle period. During the idle period, the idle timer 1535 indicates an elapsed time since the most recently detected chest compression. As no chest compressions are detected during the idle period, values for the compression depth and rate are not indicated. However, the feedback fields (i.e., the feedback indicators 1522 and 1524) may still be provided by the CPR dashboard 1545. In an implementation, a "0" or a non-numeric placeholder may indicate the lack of a measured depth and rate. The feedback fields 1526 and 1528 similarly may not indicate chest compression performance metrics during the idle period.

The CPR timer 1530 may be a chest compression timer, such as a countdown timer that indicates a time remaining in an ongoing series of chest compressions. The CPR timer 1530 may decrement the time from a pre-determined time interval until it reaches zero. For example, the control software and/or the user may set the pre-determined time interval to number of minutes over which CPR compression should be administered to the patient. This pre-determined time interval may be, for example, 1 minute, 2 minutes, 5 minutes, or another number of minutes as determined by a CPR protocol and/or resuscitation authority or administrator. The CPR idle timer 1535 may be a chest compression pause timer that indicates a duration of a pause in the administration of chest compressions. For example, the CPR idle timer 1535 may indicate a length of time during a case over which the patient has not received chest compressions (e.g., a length of time since a last detected chest compression). When a compression is detected, e.g., indicating a start of a series of chest compressions and/or a resumption of a series of chest compressions, the idle timer 1535 may not illuminate and/or otherwise may not be visible to the user of the defibrillator 1500.

In order to determine the CPR timer 1530 and the CPR idle timer 1535, the control software (e.g., processor-executable instructions that generate the user interface 1599) may include instructions that implement an algorithm to automatically identify the chest compression periods and the idle periods. An example of this algorithm may implement the following procedures. The algorithm may identify a series of chest compressions corresponding to a chest compression period based on signals from the motion sensor 118. The algorithm may distinguish between signals that correspond to CPR chest compressions, as opposed to spurious signals that do not correspond to CPR chest compressions (e.g., distinguish between compressions and motion related artifacts). For example, a spurious signal may correspond to movement of the motion sensor 118 while the rescuer is putting the motion sensor 118 in place on the patient. The spurious signal may resemble a signal generated during a chest compression but in fact may be due to a singular transient movement of the motion sensor 118 rather than an intentionally performed CPR chest compression. The algorithm may prevent the signal generated from this singular transient movement from being incorrectly identified as a signal corresponding to a first chest compression in a series of CPR chest compressions.

The series of CPR chest compressions may be identified as a group of a minimum number of compressions occurring at a minimum rate or a rate range and corresponding to a minimum depth and or a depth range and/or at a combination of a detected rate and range (e.g., compressions at >2.54 cm that occur at a particular rate). More than one compression is needed in order to establish a rate. Further, the algorithm may analyze two or more features of the motion sensor signal to improve the accuracy and sensitivity of the identification of chest compressions compared with a single factor analysis. For example, the minimum number of compressions may be 3-6 compressions, the minimum rate may be 60 compressions per minute and the minimum compression depth may be 0.75 inches (1.9 cm). In other words, the series may be identified for an occurrence of at least three compressions with a compression rate of greater than or equal to 60 cpm and a compression depth of greater than or equal to 0.75 inches (1.9 cm). Thus the chest compression period may include at least three compressions (e.g., the number of compressions in the automatically identified CPR period is greater than or equal to three). The values of three compressions, 60 cpm, and 0.75 inches (1.9 cm) are examples only and not limiting of the disclosure. Once a series of a sequence of CPR chest compressions is identified, the algorithm may initiate the CPR timer 1530. The algorithm may initiate the CPR timer 1530 such that the timer includes a set time interval before the time of the first compression of the series (e.g., 1 millisecond prior to the time of the first compression of the identified series). The first compression in the identified series is the first of at a set of at least three compressions at a particular rate and depth. The CPR timer 1530 indicates a remaining time in the sequence of CPR chest compressions.

As a further example of the algorithm procedures, the algorithm may identify the idle periods. The idle periods may be identified based on an absence of identified CPR chest compressions for a particular minimum time period. For example, the algorithm may determine that CPR is paused (e.g., identify the idle period) if the motion detected by the motion sensor 118 does not meet a 2.54 cm depth at a minimum required rate. The particular minimum time period may be a fixed value set by the control software. The idle period may correspond to a 1-9 second time period without chest compressions. The algorithm may identify a prolonged pause (e.g., 10-15 seconds) as stopped chest compressions (e.g., a cessation of chest compression delivery for at least 10-15 seconds). For paused chest compressions, the algorithm may identify a first chest compression after the pause as resumed chest compressions (e.g., as opposed to spurious motion or a start of chest compressions) without repeating the algorithmic steps used to identify the start of chest compressions. For stopped chest compressions, the algorithm may repeat the algorithmic steps used to identify the start of chest compressions. In an implementation, the start of chest compressions may trigger the CPR timer 1530 to decrement the time and initiate the CPR timer 1530 at the predetermined chest compression time interval. However, resumed chest compressions may trigger the CPR timer 1530 to continue the decrement of time using the remaining time interval before the pause (e.g., overlook the 1-10 second gap associated with the pause) or using the remaining time interval including the pause. Alternatively, the control software may provide a default value for this time period and the default value may be user-configurable via a dashboard editing tool. In an example implementation, the particular minimum time period may be two seconds. In this example, if a time interval between identified CPR chest compressions is greater than or equal to two seconds, then this time interval is determined to be an idle period. The identified chest compressions are those compressions in the series of compressions determined to be CPR chest compressions as described above.

Figure 17:
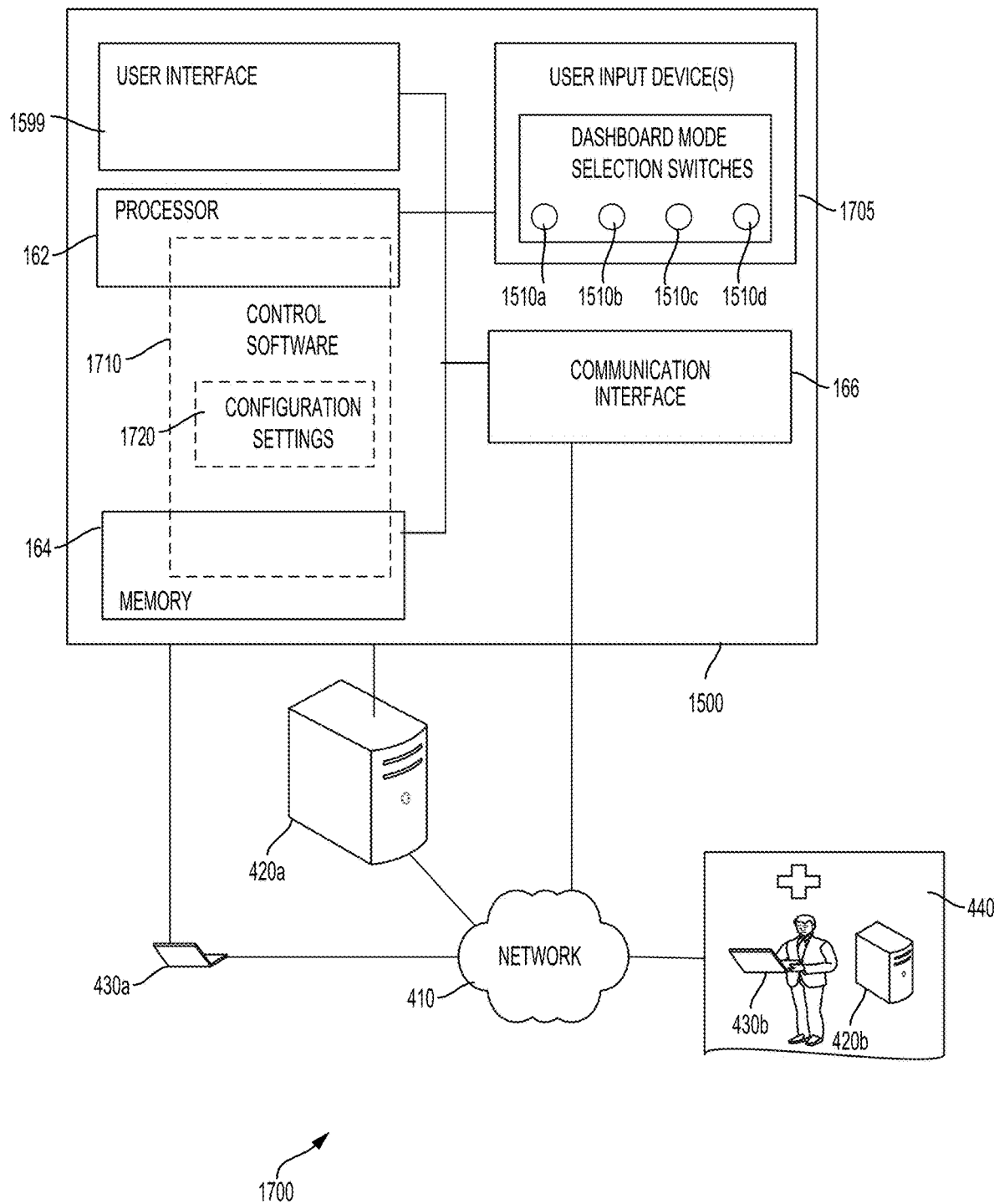
FIG. 17 shows an example of system that enables implementation of changes to configuration settings of control software.

FIG. 17 shows an example of a system 1700 that enables one or more of a manufacturer, distributor, medical supervisor, caregiver, etc. to implement changes to the configuration settings of the control software. The control software 1710 includes instructions stored on a non-transitory storage medium (e.g., the memory 164) that are processor-executable (e.g., by the processor 162). The control software includes configuration settings 1720 for the defibrillator 1500. The configuration settings 1720 include, but are not limited to, one or more of the automatic identification configuration setting, the mode selection configuration setting, and the feedback mode configuration setting discussed above. The defibrillator 1500 may include the user interface 1599 which may be an input/output device (e.g., a touch screen). The defibrillator may further include one or more input devices 1705, for example, one or more of the keyboard, mouse, joystick, trackball, or other pointing device, microphone, camera, etc. as well as one or more dashboard mode selection switches 1510a-1510d. In an implementation, the processor 162 may receive configuration setting selections via the user interface 1599 and/or via the one or more input devices 1705. In an implementation, the user interface 1599 may include the interactive menu 1540 and the processor 162 may receive configuration setting selections via the interactive menu 1540. Additionally or alternatively, the processor 162 may receive configuration setting selections via the communications interface 166. The communications interface may transmit and/or receive information from and/or to one or more computing devices external to the defibrillator 1500 via the network 410. The information may include information stored in the memory 164 of the defibrillator 1500 and may include the configuration settings 1720. Additionally or alternatively, the defibrillator 1500 may establish a wired communicative coupling with one or more of the external computing devices (e.g., the server 420a and/or the computing device 430a) The network 410 may be, for example, but not limited to, a local area network, a cellular network, and/or a computer network (e.g., an Internet Protocol network). The communications interface 166 may provide Wi-Fi, Bluetooth®, satellite, radio, ZigBee®, and/or cellular communications capabilities. The one or more external computing devices may include a server 420a and/or another computing device 430a (e.g., a personal computer, a laptop computer, a mobile device, a hand-held device, a wireless device, a tablet, a medical device, a defibrillator, a patient monitor, a wearable device (e.g., a wrist-worn device, a head-worn device, etc.), or combinations thereof. The server 420a may be a cloud server or central facility server. The one or more external computing devices may additionally and/or alternatively include a server 420b and/or a computing device 430b associated with a medical provider 440 (e.g., a hospital, a physician's office, a medical records office, an emergency services office, an emergency services vehicle, a dispatch center, etc.). Further, one or more of the external computing devices may be associated with a manufacturer, distributor, and/or other service provider for the defibrillator 1500. In an implementation, the defibrillator 1500 may receive new and/or updated control software 1710 from one or more of the external computing devices. The new and/or updated control software 1710 may include configuration setting selections and/or updates/changes to the configuration setting selections.

Figure 18:
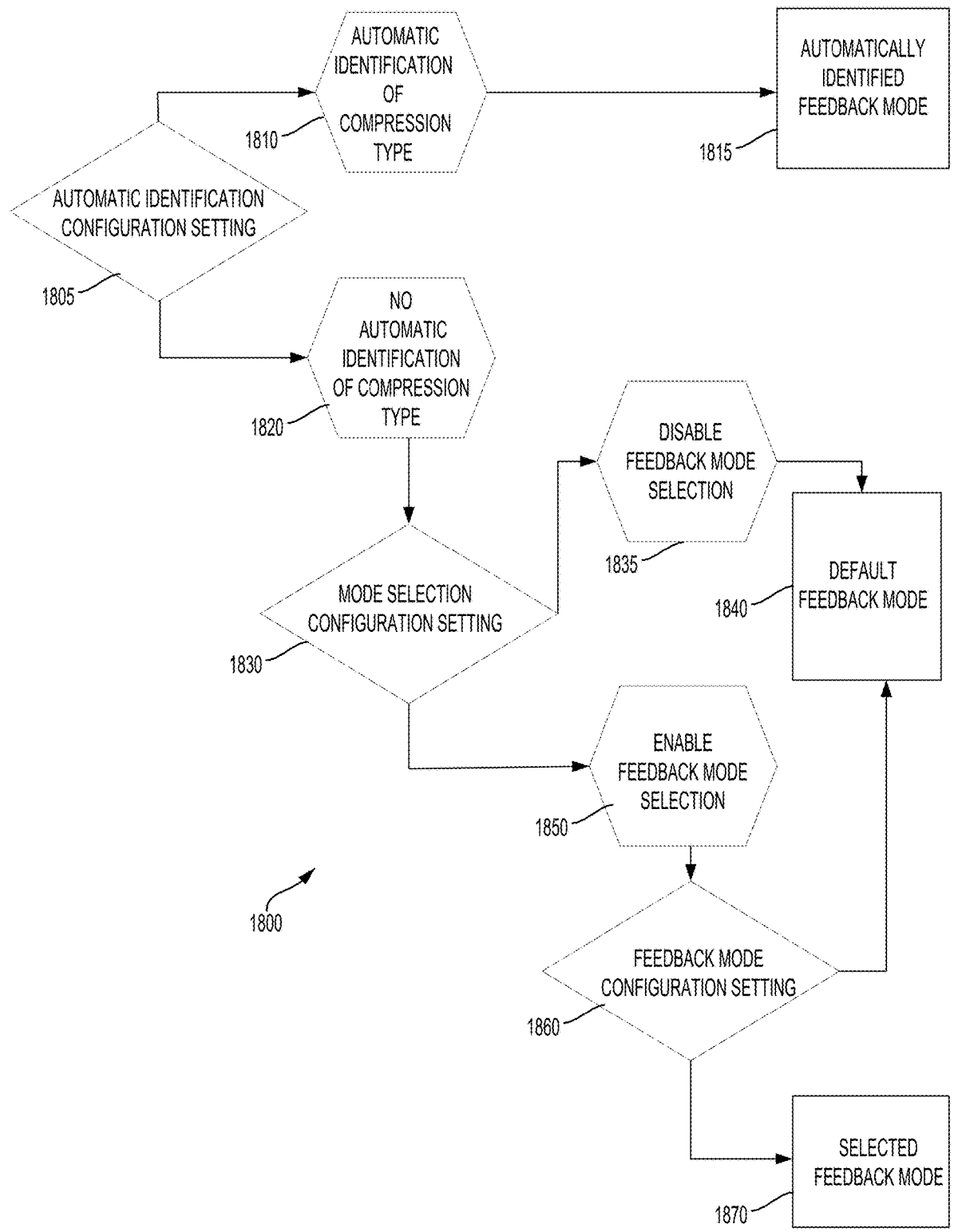
FIG. 18 shows an example of a process flow for implementing configuration setting selections.

Referring to FIG. 18, an example of a process flow 1800 for implementing the configuration setting selections is shown. The process flow 1800 includes three configuration settings, the automatic identification configuration setting 1805, the mode selection configuration setting 1830, and the feedback mode configuration setting 1860. These three settings are examples only and the control software 1710 (and/or firmware) for the defibrillator 1500 may include one or more of these settings and may include additional configuration settings. Further, the process flow 1800 an example only and not limiting. The process flow 1800 may be altered, e.g., by having stages added, removed, rearranged, combined, and/or performed concurrently.

The automatic identification configuration setting 1805 may indicate whether or not the control software 1710 includes the capability to automatically identify the type of chest compressions. Alternatively, control software 1710 may include the capability to automatically identify the type of chest compressions and the automatic identification configuration setting 1805 may indicate whether or not the control software 1710 will implement or bypass this capability. With either option, the configuration setting 1805 may indicate implementation of automatic identification of compression type 1810 or may indicate that the control software will not implement the automatic identification of compression type 1820. For automatic identification of compression type 1810, the user interface 1599 may operate in an automatically identified feedback mode 1815. In the mode 1815, the user interface 1599 may selectively provide feedback based on the type of chest compression automatically identified by the control software 1710 (e.g., as described with regard to FIGS. 5-10).

The mode selection configuration setting 1830 may determine whether or not the control software 1710 will accept user input with regard to the type of chest compressions. For example, the mode selection configuration setting 1830 may determine whether or not the one or more dashboard mode selection switches 1510*a*-1510*d* are enabled by the control software 1710. If the mode selection configuration setting is set to disable feedback mode selection 1835 (e.g., capture of user input with regard to the type of chest compressions is disabled) then the user interface 1599 may operate in the default feedback mode 1840. The user interface 1599 may also operate in the default feedback mode 1840 if the feedback mode selection is disabled and there is no automatic identification of compression type. If the mode selection configuration setting is set to enable feedback mode selection 1850 (e.g., capture of user input with regard to the type of chest compressions is enabled), then the status of the user interface 1599 may depend on the feedback mode configuration setting 1860.

The feedback mode configuration setting 1860 indicates the feedback mode selected via the user input to the defibrillator 1500. For example, in the absence of the user input, the feedback mode configuration setting 1860 may be the default setting which causes the user interface 1599 to operate in the default feedback mode 1840. For example, this scenario may occur if the user does not actuate any of the dashboard mode selection switches 1510*a*-1510*d*. In the presence of user input, the feedback mode configuration setting 1860 may be the selected setting which causes the user interface 1599 to operate in the selected feedback mode 1870. For example, this scenario may occur if the user actuates one or more of the dashboard mode selection switches 1510*a*-1510*d*. In various implementations, the user may change the feedback mode configuration setting 1860 via input to the interactive menu 1540 and/or input to the defibrillator 1500 via the one or more external computing devices 420*a*, 420*b*, 430*a*, and/or 430*b*.

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device.

A computer program is a set of instructions that can be used, directly or indirectly, in a computer to perform some activity or bring about some result. A computer program can be written in any form of programming language, including compiled or interpreted languages, and it can be deployed in any form, including as a stand-alone program or as a module, component, subroutine, or other unit suitable for use in a computing environment. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks.

The computing device 160 described herein may include, or be operatively coupled to communicate with, one or more mass storage devices for storing data files; such devices include magnetic disks, such as internal hard disks and removable disks; magneto-optical disks; and optical disks.

The terms "machine-readable medium," "computer-readable medium," and "processor-readable medium" as used herein, refer to any medium that participates in providing data that causes a machine to operate in a specific fashion. Using a computer system, various processor-readable media (e.g., a computer program product) might be involved in providing instructions/code to processor(s) for execution and/or might be used to store and/or carry such instructions/code (e.g., as signals).

In many implementations, a processor-readable medium is a physical and/or tangible storage medium. Such a medium may take many forms, including but not limited to, non-volatile media and volatile media. Non-volatile media include, for example, optical and/or magnetic disks. Volatile media include, without limitation, dynamic memory.

Common forms of physical and/or tangible processor-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, EPROM, a FLASH-EPROM, any other memory chip or cartridge, a carrier wave as described hereinafter, or any other medium from which a computer can read instructions and/or code.

Various forms of processor-readable media may be involved in carrying one or more sequences of one or more instructions to one or more processors for execution. Merely by way of example, the instructions may initially be carried on a flash device, a device including persistent memory, and/or a magnetic disk and/or optical disc of a remote computer. A remote computer might load the instructions into its dynamic memory and send the instructions as signals over a transmission medium to be received and/or executed by a computer system.

The computing device 160 may be part of a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet. The computer system can include clients and servers. A client and server are generally remote from each other and typically interact through a network, such as the described one. The relationship of client and server arises by virtue of computer programs running on the respective computers and having a client-server relationship to each other.

Substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

Information and signals may be represented using any of a variety of different technologies and techniques. For example, data, instructions, commands, information, signals, and symbols that may be referenced throughout the above description may be represented by voltages, currents, electromagnetic waves, magnetic fields or particles, optical fields or particles, or any combination thereof.

The methods, systems, and devices discussed above are examples. Various alternative configurations may omit, substitute, or add various procedures or components as appropriate. Configurations may be described as a process which is depicted as a flow diagram or block diagram. Although each may describe the operations as a sequential process, many of the operations can be performed in parallel or concurrently. In addition, the order of the operations may be rearranged. A process may have additional stages not included in the figure. Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the scope of the disclosure.

Also, configurations may be described as a process which is depicted as a flow diagram or block diagram. Although each may describe the operations as a sequential process, many of the operations can be performed in parallel or concurrently. In addition, the order of the operations may be rearranged. A process may have additional stages or functions not included in the figure. Furthermore, examples of the methods may be implemented by hardware, software, firmware, middleware, microcode, hardware description languages, or any combination thereof. When implemented in software, firmware, middleware, or microcode, the program code or code segments to perform the tasks may be stored in a non-transitory processor-readable medium such as a storage medium. Processors may perform the described tasks.

Components, functional or otherwise, shown in the figures and/or discussed herein as being connected or communicating with each other are communicatively coupled. That is, they may be directly or indirectly connected to enable communication between them.

As used herein, including in the claims, "and" as used in a list of items prefaced by "at least one of" indicates a disjunctive list such that, for example, a list of "at least one of A, B, and C" means A or B or C or AB or AC or BC or ABC (i.e., A and B and C), or combinations with more than one feature (e.g., AA, AAB, ABBC, etc.). As used herein, including in the claims, unless otherwise stated, a statement that a function or operation is "based on" an item or condition means that the function or operation is based on the stated item or condition and may be based on one or more items and/or conditions in addition to the stated item or condition.

Having described several example configurations, various modifications, alternative constructions, and equivalents may be used without departing from the disclosure. For example, the above elements may be components of a larger system, wherein other rules may take precedence over or otherwise modify the application of the invention. Also, a number of operations may be undertaken before, during, or after the above elements are considered. Also, technology evolves and, thus, many of the elements are examples and do not bound the scope of the disclosure or claims. Accordingly, the above description does not bound the scope of the claims. Further, more than one invention may be disclosed.

Other embodiments are within the scope of the invention. For example, due to the nature of software, functions described above can be implemented using software, hardware, firmware, hardwiring, or combinations of any of these. Features implementing functions may also be physically located at various locations, including being distributed such that portions of functions are implemented at different physical locations.

What is claimed is:

1. A system for assisting a rescuer in providing resuscitative treatment to a victim of a cardiac event, the system comprising:
    at least one motion sensor comprising an accelerometer and configured to generate acceleration signals that are indicative of motion of the chest of the victim during an administration of chest compressions to the victim;
    a patient monitor/defibrillator comprising:
        a user interface comprising:
            at least one dashboard mode selection switch wherein an actuation of the at least one dashboard mode selection switch identifies a type of administered chest compressions, the type comprising mechanically assisted active compression-decompression (ACD) chest compressions delivered via manual operation of an ACD device; and
            at least one output device comprising a display configured to provide a CPR dashboard configured to display chest compression parameters; and
        a processor, a memory, and associated circuitry, the processor communicatively coupled to the at least one motion sensor, the at least one dashboard mode selection switch, and the at least one output device, and configured to:
            receive the acceleration signals from the at least one motion sensor,
            process the acceleration signals received from the at least one motion sensor,
            calculate chest compression feedback parameters from the processed acceleration signals, the calculated chest compression feedback parameters comprising chest compression depth and chest compression rate,
wherein the chest compression parameters include the calculated chest
compression feedback parameters, and,
in response to the actuation of the at least one dashboard mode selection switch, control the at least one output device to change an appearance of the CPR dashboard such that the CPR dashboard suppresses a display of at least a portion of the calculated chest compression feedback parameters based at least in part on the type of administered chest compressions identified by the actuation of the at least one dashboard mode selection switch.

2. The system of claim 1, wherein the at least one output device comprises a speaker and the CPR dashboard is configured to audibly provide at least a portion of the chest compression parameters via the speaker and wherein the processor is configured to control the at least one output device to suppress at least a portion of the audibly provided chest compression parameters based at least in part on the identified type of the administered chest compressions.

3. The system of claim 1 wherein the chest compression parameters comprise at least one of a chest compression timer that indicates a time remaining in an ongoing series of chest compressions and a chest compression pause timer that indicates a duration of a pause in an active delivery of chest compressions.

4. The system of claim 3 wherein the at least one output device is configured to provide the chest compression timer and the chest compression pause timer based on the acceleration signals.

5. The system of claim 1 wherein the chest compression parameters comprise one or more of a chest release indicator and a perfusion indicator.

6. The system of claim 5 wherein the processor is configured to control the at least one output device to suppress a display of at least one of the chest release indicator and the perfusion indicator based at least in part on the identification of the type of administered chest compressions by the actuation of the at least one dashboard mode selection switch.

7. The system of claim 1 wherein the processor is configured to control the at least one output device to provide the chest compression parameters at the CPR dashboard in a default output mode in an absence of the actuation of the at least one dashboard mode selection switch.

8. The system of claim 7 wherein the default output mode corresponds to manual chest compressions.

9. The system of claim 7 wherein the processor is configured to transition the at least one output device from the default output mode to a selected output mode in response to the actuation of the at least one dashboard mode selection switch.

10. The system of claim 9 wherein, in the selected output mode, the at least one output device is configured to suppress an output of at least a portion of chest compression parameters provided in the default output mode.

11. The system of claim 9 wherein, in the selected output mode, the at least one output device is configured to provide an indication of the identified type of administered chest compressions associated with the selected output mode.

12. The system of claim 7 wherein the processor is configured to operate the at least one output device in the default output mode upon initiation of a patient case.

13. The system of claim 1 wherein the at least one dashboard mode selection switch comprises one or more soft-keys.

14. The system of claim 1 wherein the at least one output device comprises a speaker.

15. The system of claim 1 wherein the processor is configured to store, in the memory, the calculated chest compression feedback parameters with data that indicates the identified type of administered chest compressions.

16. The system of claim 1, comprising a defibrillation electrode assembly configured to couple to the patient monitor/defibrillator, wherein the at least one motion sensor is disposed in the defibrillation electrode assembly.

17. The system of claim 14, wherein the processor is configured to control the speaker to silence a metronome based at least in part on the identified type of administered chest compressions indicated by the actuation of the at least one dashboard mode selection switch.

18. The system of claim 1, wherein the processor is configured to:
process the acceleration signals received from the at least one motion sensor to automatically identify the type of administered chest compressions as automated chest compressions from a belt-based system, and
control the at least one output device to change the appearance of the CPR dashboard such that the CPR dashboard suppresses a display of at least one of the chest compression depth and the chest compression rate based at least in part on the type of administered chest compressions indicated by the automatic identification.

19. The system of claim 18, wherein the at least one output device is configured to change the appearance of the CPR dashboard to:
suppress the display of the chest compression depth, and the chest compression rate, and suppress a display of a chest release indicator and a perfusion indicator, in response to the automatic identification of the automated chest compressions from the belt-based system.

20. The system of claim 19, wherein the at least one output device is configured to replace the display of the chest compression depth, the chest compression rate, the chest release indicator, and the perfusion indicator with an indication of the type of administered chest compressions as the automated chest compressions from the belt-based system.

21. The system of claim 1, wherein the appearance of the CPR dashboard changes from (a) providing at least one of a chest compression timer and a chest compression pause timer and providing at least one of the chest compression depth, the chest compression rate, a chest release indicator, and a perfusion indicator to (b) providing the at least one of the chest compression timer and the chest compression pause timer without providing any of the chest compression depth, the chest compression rate, the chest release indicator, and the perfusion indicator, based at least in part on the identified type of administered chest compressions by the actuation of the at least one dashboard mode selection switch.

22. The system of claim 1, wherein in response to the actuation of the at least on dashboard mode selection switch, the processor is configured to control the at least one output device to change the appearance of the CPR dashboard to provide an indication that the type of administered chest compressions is the mechanically assisted ACD chest compressions.

23. The system of claim 18, wherein the at least one output device is configured to provide an indication that the type of administered chest compressions is the automated chest compressions.

24. The system of claim 18, wherein the at least one output device comprises a speaker and the CPR dashboard is configured to audibly provide at least a portion of the chest compression parameters via the speaker and wherein the processor is configured to control the at least one output device to suppress at least a portion of the audibly provided chest compression parameters based at least in part on the type of administered chest compressions indicated by the automatic identification.

\* \* \* \* \*

UNITED STATES PATENT AND TRADEMARK OFFICE
CERTIFICATE OF CORRECTION

| | |
|---|---|
| PATENT NO. | : 11,311,457 B2 |
| APPLICATION NO. | : 15/911600 |
| DATED | : April 26, 2022 |
| INVENTOR(S) | : Tan et al. |

It is certified that error appears in the above-identified patent and that said Letters Patent is hereby corrected as shown below:

In the Specification

Column 38, Line 18, delete "and or", insert -- and/or --
Column 42, Line 58, delete "and or", insert -- and/or --

In the Claims

Claim 21, Column 50, Line 51, delete "depth ,", insert -- depth, --
Claim 21, Column 50, Line 55, delete "depth ,", insert -- depth, --
Claim 22, Column 50, Line 62, delete "on", insert -- one --

Signed and Sealed this
Nineteenth Day of July, 2022

*Katherine Kelly Vidal*

Katherine Kelly Vidal
*Director of the United States Patent and Trademark Office*